US007078515B2

(12) United States Patent
Wallace et al.

(10) Patent No.: US 7,078,515 B2
(45) Date of Patent: Jul. 18, 2006

(54) SODIUM-CHANNEL ALPHA1-SUBUNIT AND THEIR POLYPEPTIDES AND THEIR TREATMENT OF GENERALIZED EPILEPSY WITH FEBRILE SEIZURES PLUS

(75) Inventors: Robyn Heather Wallace, Memphis, TN (US); John Charles Mulley, Firle (AU); Samuel Frank Berkovic, Caulfield North (AU)

(73) Assignee: Bionomics Limited, Thebarton (AU)

( * ) Notice: Subject to any disclaimer, the term of this patent is extended or adjusted under 35 U.S.C. 154(b) by 70 days.

(21) Appl. No.: 10/451,126

(22) PCT Filed: Dec. 20, 2001

(86) PCT No.: PCT/AU01/01648

§ 371 (c)(1),
(2), (4) Date: Oct. 8, 2003

(87) PCT Pub. No.: WO02/50096

PCT Pub. Date: Jun. 27, 2002

(65) Prior Publication Data

US 2004/0110706 A1    Jun. 10, 2004

(30) Foreign Application Priority Data

Dec. 20, 2000  (AU) .................................. PR 2203

(51) Int. Cl.
*C07H 21/00* (2006.01)
*C07H 14/00* (2006.01)
*C12N 15/11* (2006.01)
*C12N 15/12* (2006.01)
*C12N 15/63* (2006.01)
*C12N 15/70* (2006.01)
*C12N 15/79* (2006.01)

(52) U.S. Cl. .................. 536/23.5; 530/350; 435/320.1; 435/69.1; 435/252.1; 435/325

(58) Field of Classification Search .................... 435/6, 435/320.1, 252.3, 254.2, 325; 530/350; 536/23.5
See application file for complete search history.

(56) References Cited

U.S. PATENT DOCUMENTS

2003/0157525 A1 * 8/2003 Mintier et al.
2004/0214195 A1 * 10/2004 Rouleau
2004/0229257 A1   11/2004 Petrou et al.

FOREIGN PATENT DOCUMENTS

AU    2001 18465 A1   11/2000

OTHER PUBLICATIONS

Lerche H, Jurkat-Rott K, Lehmann-Horn F. 2001. Ion channels and epilepsy.Am J Med Genet. 106(2):146-59.*
Lason W. 2001. Neurochemical and pharmacological aspects of cocaine-induced seizures. Polish Journal of Pharmacology 53:57-60.*
Mazumder et al. 2004. Translations control by the 3'-UTR: the ends specify the means. Trends in Biochemical Sciences 28:91-98.*
Moran, O. et al. 2001. Biochem Biophys Res Comm 282:55-59/.*
Geysen H.M. et al. 1988. Cognitive features of continuous antigenic determinants. Journal of Molecular Recognition 1:32-41.*
Baulac et al., *A Second Locus for Familial Generalized Epilepsy with Febrile Seizures Plus Maps to Chromosome 2q21-q33*, Am. J. Hum. Genet. 65:1078-1085 (1999).
Escayg et al., *Mutations of SCN1A, encoding a neuronal sodium channel, in two families with GEFS+2*, Nature Genetics 24:343-345 (Apr. 2000).
Lopes-Cendes et al., *A New Locus for Generalized Epilepsy with Febrile Seizures Plus Maps to Chromosome 2*, Am. J. Hum. Genet. 66:698-701 (2000).
Moulard et al., *Identification of a New Locus for Generalized Epilepsy with Febrile Seizures Plus (GEFS+) on Chromosome 2q24-q33*, Am. J. Hum. Genet. 65:1396-1400 (1999).
Peiffer et al., *A Locus for Febrile Seizures (FEB3) Maps to Chromosome 2q23-24*, Annals of Neurology 46(4):671-678 (Oct. 1999).
Plummer et al., *Exon Organization, Coding Sequence, Physical Mapping, and Polymorphic Intragenic Markers for the Human Neuronal Sodium Channel Gene SCN8A*, Genomics 54:287-296 (1998).
Plummer et al., *Evolution and Diversity of Mammalian Sodium Channel Genes*, Genomics 57:323-331 (1999).
Scheffer et al., *Generlized epilepsy with febrile seizures plus A genetic disorder with heterogeneous clinical phenotypes*, Brain 120:479-490 (1997).
Scheffer et al., *Locus for Febrile Seizures*, Annals of Neurology 47(6):840-841 (Jun. 2000).
Singh et al., *Generlized Epilepsy with Febrile Seizures Plus: A Common Childhood-Onset Genetic Epilepsy Syndrome*, Annals of Neurology 45(1):75-81 (Jan. 1999).

(Continued)

Primary Examiner—Janet L. Andres
Assistant Examiner—Daniel E. Kolker
(74) Attorney, Agent, or Firm—Jenkins, Wilson & Taylor, P.A.

(57) ABSTRACT

The mutations D188V, V1353L, I1656M in the neuronal gene sodium-channel alpha1-subunit, SCN1A, are disclosed. The methods of using their associated polypeptides for treating sodium channel dysfunction disorders including generalized epilepsy are also disclosed.

20 Claims, 5 Drawing Sheets

OTHER PUBLICATIONS

Wallace et al., *Febrile seizures and generalized epilepsy associated with a mutation in the Na⁺-channel β1 subunit gene SCN1B, Nature Genetics* 19:366-370 (Aug. 1998).

Alekov et al., "A sodium channel mutation causing epilepsy in man exhibits subtle defects in fast inactivation and activation *in vitro,*" *Journal of Physiology*, 529(3):533-539 (2000).

Wallace et al., "Neuronal Sodium-Channel α1-Subunit Mutations in Generalized Epilepsy with Febrile Seizures Plus," *Am. J. Hum. Genet.*, 68:859-865 (2001).

Escayg et al., *A Novel SCN1A Mutation Associated with Generalized Epilepsy with Febrile Seizures Plus- and Prevelance of Variants in Patients with Epilepsy, Am. J. of Hum. Genet.* 68:866-873 (2001).

* cited by examiner

| | febrile seizures (FS) | X | D188V |
|---|---|---|---|
| | febrile seizures plus (FS+) | Y | V1353L |
| | FS+, extended phenotype | Z | I1656M |
| | Unclassified | 0 | no mutation |
| | Partial epilepsy | | |
| | Juvenile myoclonic epilepsy | | |

Figure 3 i) D188V

| | | | | | | | | | | |
|---|---|---|---|---|---|---|---|---|---|---|
| SCN1A | F | T | F | L | R | D | P | W | N | W | L |
| RAT SCN1A | - | - | - | - | - | - | - | - | - | - | - |
| SCN2A | - | - | - | - | - | - | - | - | - | - | - |
| SCN3A | - | - | - | - | - | - | - | - | - | - | - |
| SCN4A | - | - | - | - | - | - | - | - | - | - | - |
| SCN5A | - | - | - | - | - | - | - | - | - | - | - |
| SCN6A | - | S | - | - | G | - | - | - | - | - | - |
| SCN8A | - | - | - | - | - | - | - | - | - | - | - |
| SCN9A | - | - | - | - | - | - | - | - | - | - | - |
| SCN10A | - | - | Y | - | - | - | - | - | - | - | - |
| SCN11A | - | S | - | - | - | - | - | - | - | - | - |
| SCN12A | - | S | - | - | - | - | - | - | - | - | - |
| EL. EEL | - | - | - | - | - | - | - | - | - | - | - |
| DROS | - | - | Y | - | - | - | A | - | - | - | - |
| SQUID | - | - | Y | - | - | - | A | - | - | - | - |
| FLATWORM | - | - | Y | - | - | S | I | - | - | - | - |
| JELLYFISH | Y | S | Y | - | - | N | S | - | - | - | - | ii) V1353L

| | | | | | | | | | | |
|---|---|---|---|---|---|---|---|---|---|---|
| SCN1A | M | N | V | L | L | V | C | L | I | F | W |
| RAT SCN1A | - | - | - | - | - | - | - | - | - | - | - |
| SCN2A | - | - | - | - | - | - | - | - | - | - | - |
| SCN3A | - | - | - | - | - | - | - | - | - | - | - |
| SCN4A | - | - | - | - | - | - | - | - | - | - | - |
| SCN5A | - | - | - | - | - | - | - | - | - | - | - |
| SCN6A | L | - | - | F | - | - | - | - | M | I | - |
| SCN8A | - | - | - | - | - | - | - | - | - | - | - |
| SCN9A | - | - | - | - | - | - | - | - | - | - | - |
| SCN10A | - | - | - | - | - | - | - | - | - | - | - |
| SCN11A | L | - | - | - | - | - | - | - | - | - | - |
| SCN12A | L | - | - | - | - | - | - | - | - | - | - |
| EL. EEL | - | - | - | - | - | - | - | - | - | - | - |
| DROS | F | - | - | - | - | - | - | - | - | - | - |
| SQUID | F | - | - | - | - | - | - | - | V | - | - |
| FLATWORM | F | - | - | M | V | - | - | - | V | - | - |
| JELLYFISH | A | - | - | - | - | - | - | G | V | - | - | iii) I1656M

| | | | | | | | | | | |
|---|---|---|---|---|---|---|---|---|---|---|
| SCN1A | K | G | A | K | G | I | R | T | L | L | F |
| RAT SCN1A | - | - | - | - | - | - | - | - | - | - | - |
| SCN2A | - | - | - | - | - | - | - | - | - | - | - |
| SCN3A | - | - | - | - | - | - | - | - | - | - | - |
| SCN4A | R | - | - | - | - | - | - | - | - | - | - |
| SCN5A | R | - | - | - | - | - | - | - | - | - | - |
| SCN6A | - | - | P | - | V | F | H | N | - | M | L |
| SCN8A | - | - | - | - | - | - | - | - | - | - | - |
| SCN9A | - | - | - | - | - | - | - | - | - | - | - |
| SCN10A | R | A | - | - | - | - | - | - | - | - | - |
| SCN11A | R | A | - | - | - | - | - | - | - | - | - |
| SCN12A | R | A | - | - | - | - | - | - | - | - | - |
| EL. EEL | - | - | - | - | - | - | - | - | - | - | - |
| DROS | - | - | - | - | - | - | - | - | - | - | - |
| SQUID | - | S | - | - | - | - | - | - | - | - | - |
| FLATWORM | - | S | - | R | - | - | - | - | - | - | - |
| JELLYFISH | D | - | - | - | - | - | - | Q | - | - | - |

SEQUENCE LISTING

<160> NUMBER OF SEQ ID NOS: 89

<210> SEQ ID NO 1
<211> LENGTH: 8381
<212> TYPE: DNA
<213> ORGANISM: Homo sapiens
<220> FEATURE:
<221> NAME/KEY: CDS
<222> LOCATION: (267)..(6296)

<400> SEQUENCE: 1

```
atactgcaga ggtctctggt gcatgtgtgt atgtgtgcgt ttgtgtgtgt ttgtgtgtct      60
gtgtgttctg ccccagtgag actgcagccc ttgtaaatac tttgacacct tttgcaagaa     120
ggaatctgaa caattgcaac tgaaggcaca ttgttatcat ctcgtctttg ggtgatgctg     180
ttcctcactg cagatggata attttccttt taatcaggaa tttcatatgc agaataaatg     240
gtaattaaaa tgtgcaggat gacaag atg gag caa aca gtg ctt gta cca cca     293
                             Met Glu Gln Thr Val Leu Val Pro Pro
                               1               5 gga cct gac agc ttc aac ttc ttc acc aga gaa tct ctt gcg gct att     341
Gly Pro Asp Ser Phe Asn Phe Phe Thr Arg Glu Ser Leu Ala Ala Ile
 10              15                  20                  25 gaa aga cgc att gca gaa gaa aag gca aag aat ccc aaa cca gac aaa     389
Glu Arg Arg Ile Ala Glu Glu Lys Ala Lys Asn Pro Lys Pro Asp Lys
             30                  35                  40 aaa gat gac gac gaa aat ggc cca aag cca aat agt gac ttg gaa gct     437
Lys Asp Asp Asp Glu Asn Gly Pro Lys Pro Asn Ser Asp Leu Glu Ala
         45                  50                  55 gga aag aac ctt cca ttt att tat gga gac att cct cca gag atg gtg     485
Gly Lys Asn Leu Pro Phe Ile Tyr Gly Asp Ile Pro Pro Glu Met Val
     60                  65                  70 tca gag ccc ctg gag gac ctg gac ccc tac tat atc aat aag aaa act     533
Ser Glu Pro Leu Glu Asp Leu Asp Pro Tyr Tyr Ile Asn Lys Lys Thr
 75                  80                  85 ttt ata gta ttg aat aaa ttg aag gcc atc ttc cgg ttc agt gcc acc     581
Phe Ile Val Leu Asn Lys Leu Lys Ala Ile Phe Arg Phe Ser Ala Thr
 90                  95                 100                 105 tct gcc ctg tac att tta act ccc ttc aat cct ctt agg aaa ata gct     629
Ser Ala Leu Tyr Ile Leu Thr Pro Phe Asn Pro Leu Arg Lys Ile Ala
                110                 115                 120 att aag att ttg gta cat tca tta ttc agc atg cta att atg tgc act     677
Ile Lys Ile Leu Val His Ser Leu Phe Ser Met Leu Ile Met Cys Thr
            125                 130                 135 att ttg aca aac tgt gtg ttt atg aca atg agt aac cct cct gat tgg     725
Ile Leu Thr Asn Cys Val Phe Met Thr Met Ser Asn Pro Pro Asp Trp
        140                 145                 150
```

-continued

| | | |
|---|---|---|
| aca aag aat gta gaa tac acc ttc aca gga ata tat act ttt gaa tca<br>Thr Lys Asn Val Glu Tyr Thr Phe Thr Gly Ile Tyr Thr Phe Glu Ser<br>155 160 165 | 773 |
| ctt ata aaa att att gca agg gga ttc tgt tta gaa gat ttt act ttc<br>Leu Ile Lys Ile Ile Ala Arg Gly Phe Cys Leu Glu Asp Phe Thr Phe<br>170 175 180 185 | 821 |
| ctt cgg gtt cca tgg aac tgg ctc gat ttc act gtc att aca ttt gcg<br>Leu Arg Val Pro Trp Asn Trp Leu Asp Phe Thr Val Ile Thr Phe Ala<br>190 195 200 | 869 |
| tac gtc aca gag ttt gtg gac ctg ggc aat gtc tcg gca ttg aga aca<br>Tyr Val Thr Glu Phe Val Asp Leu Gly Asn Val Ser Ala Leu Arg Thr<br>205 210 215 | 917 |
| ttc aga gtt ctc cga gca ttg aag acg att tca gtc att cca ggc ctg<br>Phe Arg Val Leu Arg Ala Leu Lys Thr Ile Ser Val Ile Pro Gly Leu<br>220 225 230 | 965 |
| aaa acc att gtg gga gcc ctg atc cag tct gtg aag aag ctc tca gat<br>Lys Thr Ile Val Gly Ala Leu Ile Gln Ser Val Lys Lys Leu Ser Asp<br>235 240 245 | 1013 |
| gta atg atc ctg act gtg ttc tgt ctg agc gta ttt gct cta att ggg<br>Val Met Ile Leu Thr Val Phe Cys Leu Ser Val Phe Ala Leu Ile Gly<br>250 255 260 265 | 1061 |
| ctg cag ctg ttc atg ggc aac ctg agg aat aaa tgt ata caa tgg cct<br>Leu Gln Leu Phe Met Gly Asn Leu Arg Asn Lys Cys Ile Gln Trp Pro<br>270 275 280 | 1109 |
| ccc acc aat gct tcc ttg gag gaa cat agt ata gaa aag aat ata act<br>Pro Thr Asn Ala Ser Leu Glu Glu His Ser Ile Glu Lys Asn Ile Thr<br>285 290 295 | 1157 |
| gtg aat tat aat ggt aca ctt ata aat gaa act gtc ttt gag ttt gac<br>Val Asn Tyr Asn Gly Thr Leu Ile Asn Glu Thr Val Phe Glu Phe Asp<br>300 305 310 | 1205 |
| tgg aag tca tat att caa gat tca aga tat cat tat ttc ctg gag ggt<br>Trp Lys Ser Tyr Ile Gln Asp Ser Arg Tyr His Tyr Phe Leu Glu Gly<br>315 320 325 | 1253 |
| ttt tta gat gca cta cta tgt gga aat agc tct gat gca ggc caa tgt<br>Phe Leu Asp Ala Leu Leu Cys Gly Asn Ser Ser Asp Ala Gly Gln Cys<br>330 335 340 345 | 1301 |
| cca gag gga tat atg tgt gtg aaa gct ggt aga aat ccc aat tat ggc<br>Pro Glu Gly Tyr Met Cys Val Lys Ala Gly Arg Asn Pro Asn Tyr Gly<br>350 355 360 | 1349 |
| tac aca agc ttt gat acc ttc agt tgg gct ttt ttg tcc ttg ttt cga<br>Tyr Thr Ser Phe Asp Thr Phe Ser Trp Ala Phe Leu Ser Leu Phe Arg<br>365 370 375 | 1397 |
| cta atg act cag gac ttc tgg gaa aat ctt tat caa ctg aca tta cgt<br>Leu Met Thr Gln Asp Phe Trp Glu Asn Leu Tyr Gln Leu Thr Leu Arg<br>380 385 390 | 1445 |
| gct gct ggg aaa acg tac atg ata ttt ttt gta ttg gtc att ttc ttg<br>Ala Ala Gly Lys Thr Tyr Met Ile Phe Phe Val Leu Val Ile Phe Leu<br>395 400 405 | 1493 |
| ggc tca ttc tac cta ata aat ttg atc ctg gct gtg gtg gcc atg gcc<br>Gly Ser Phe Tyr Leu Ile Asn Leu Ile Leu Ala Val Val Ala Met Ala<br>410 415 420 425 | 1541 |
| tac gag gaa cag aat cag gcc acc ttg gaa gaa gca gaa cag aaa gag<br>Tyr Glu Glu Gln Asn Gln Ala Thr Leu Glu Glu Ala Glu Gln Lys Glu<br>430 435 440 | 1589 |
| gcc gaa ttt cag cag atg att gaa cag ctt aaa aag caa cag gag gca<br>Ala Glu Phe Gln Gln Met Ile Glu Gln Leu Lys Lys Gln Gln Glu Ala<br>445 450 455 | 1637 |
| gct cag cag gca gca acg gca act gcc tca gaa cat tcc aga gag ccc<br>Ala Gln Gln Ala Ala Thr Ala Thr Ala Ser Glu His Ser Arg Glu Pro<br>460 465 470 | 1685 |

```
agt gca gca ggc agg ctc tca gac agc tca tct gaa gcc tct aag ttg     1733
Ser Ala Ala Gly Arg Leu Ser Asp Ser Ser Ser Glu Ala Ser Lys Leu
475                 480                 485 agt tcc aag agt gct aag gaa aga aga aat cgg agg aag aaa aga aaa     1781
Ser Ser Lys Ser Ala Lys Glu Arg Arg Asn Arg Arg Lys Lys Arg Lys
490                 495                 500                 505 cag aaa gag cag tct ggt ggg gaa gag aaa gat gag gat gaa ttc caa     1829
Gln Lys Glu Gln Ser Gly Gly Glu Glu Lys Asp Glu Asp Glu Phe Gln
                510                 515                 520 aaa tct gaa tct gag gac agc atc agg agg aaa ggt ttt cgc ttc tcc     1877
Lys Ser Glu Ser Glu Asp Ser Ile Arg Arg Lys Gly Phe Arg Phe Ser
525                 530                 535 att gaa ggg aac cga ttg aca tat gaa aag agg tac tcc tcc cca cac     1925
Ile Glu Gly Asn Arg Leu Thr Tyr Glu Lys Arg Tyr Ser Ser Pro His
        540                 545                 550 cag tct ttg ttg agc atc cgt ggc tcc cta ttt tca cca agg cga aat     1973
Gln Ser Leu Leu Ser Ile Arg Gly Ser Leu Phe Ser Pro Arg Arg Asn
555                 560                 565 agc aga aca agc ctt ttc agc ttt aga ggg cga gca aag gat gtg gga     2021
Ser Arg Thr Ser Leu Phe Ser Phe Arg Gly Arg Ala Lys Asp Val Gly
570                 575                 580                 585 tct gag aac gac ttc gca gat gat gag cac agc acc ttt gag gat aac     2069
Ser Glu Asn Asp Phe Ala Asp Asp Glu His Ser Thr Phe Glu Asp Asn
                590                 595                 600 gag agc cgt aga gat tcc ttg ttt gtg ccc cga cga cac gga gag aga     2117
Glu Ser Arg Arg Asp Ser Leu Phe Val Pro Arg Arg His Gly Glu Arg
        605                 610                 615 cgc aac agc aac ctg agt cag acc agt agg tca tcc cgg atg ctg gca     2165
Arg Asn Ser Asn Leu Ser Gln Thr Ser Arg Ser Ser Arg Met Leu Ala
620                 625                 630 gtg ttt cca gcg aat ggg aag atg cac agc act gtg gat tgc aat ggt     2213
Val Phe Pro Ala Asn Gly Lys Met His Ser Thr Val Asp Cys Asn Gly
635                 640                 645 gtg gtt tcc ttg gtt ggt gga cct tca gtt cct aca tcg cct gtt gga     2261
Val Val Ser Leu Val Gly Gly Pro Ser Val Pro Thr Ser Pro Val Gly
650                 655                 660                 665 cag ctt ctg cca gag gtg ata ata gat aag cca gct act gat gac aat     2309
Gln Leu Leu Pro Glu Val Ile Ile Asp Lys Pro Ala Thr Asp Asp Asn
                670                 675                 680 gga aca acc act gaa act gaa atg aga aag aga agg tca agt tct ttc     2357
Gly Thr Thr Thr Glu Thr Glu Met Arg Lys Arg Arg Ser Ser Ser Phe
        685                 690                 695 cac gtt tcc atg gac ttt cta gaa gat cct tcc caa agg caa cga gca     2405
His Val Ser Met Asp Phe Leu Glu Asp Pro Ser Gln Arg Gln Arg Ala
            700                 705                 710 atg agt ata gcc agc att cta aca aat aca gta gaa gaa ctt gaa gaa     2453
Met Ser Ile Ala Ser Ile Leu Thr Asn Thr Val Glu Glu Leu Glu Glu
715                 720                 725 tcc agg cag aaa tgc cca ccc tgt tgg tat aaa ttt tcc aac ata ttc     2501
Ser Arg Gln Lys Cys Pro Pro Cys Trp Tyr Lys Phe Ser Asn Ile Phe
730                 735                 740                 745 tta atc tgg gac tgt tct cca tat tgg tta aaa gtg aaa cat gtt gtc     2549
Leu Ile Trp Asp Cys Ser Pro Tyr Trp Leu Lys Val Lys His Val Val
                750                 755                 760 aac ctg gtt gtg atg gac cca ttt gtt gac ctg gcc atc acc atc tgt     2597
Asn Leu Val Val Met Asp Pro Phe Val Asp Leu Ala Ile Thr Ile Cys
        765                 770                 775 att gtc tta aat act ctt ttc atg gcc atg gag cac tat cca atg acg     2645
Ile Val Leu Asn Thr Leu Phe Met Ala Met Glu His Tyr Pro Met Thr
780                 785                 790
```

```
gac cat ttc aat aat gtg ctt aca gta gga aac ttg gtt ttc act ggg    2693
Asp His Phe Asn Asn Val Leu Thr Val Gly Asn Leu Val Phe Thr Gly
        795                 800                 805 atc ttt aca gca gaa atg ttt ctg aaa att att gcc atg gat cct tac    2741
Ile Phe Thr Ala Glu Met Phe Leu Lys Ile Ile Ala Met Asp Pro Tyr
810                 815                 820                 825 tat tat ttc caa gaa ggc tgg aat atc ttt gac ggt ttt att gtg acg    2789
Tyr Tyr Phe Gln Glu Gly Trp Asn Ile Phe Asp Gly Phe Ile Val Thr
                830                 835                 840 ctt agc ctg gta gaa ctt gga ctc gcc aat gtg gaa gga tta tct gtt    2837
Leu Ser Leu Val Glu Leu Gly Leu Ala Asn Val Glu Gly Leu Ser Val
            845                 850                 855 ctc cgt tca ttt cga ttg ctg cga gtt ttc aag ttg gca aaa tct tgg    2885
Leu Arg Ser Phe Arg Leu Leu Arg Val Phe Lys Leu Ala Lys Ser Trp
        860                 865                 870 cca acg tta aat atg cta ata aag atc atc ggc aat tcc gtg ggg gct    2933
Pro Thr Leu Asn Met Leu Ile Lys Ile Ile Gly Asn Ser Val Gly Ala
875                 880                 885 ctg gga aat tta acc ctc gtc ttg gcc atc atc gtc ttc att ttt gcc    2981
Leu Gly Asn Leu Thr Leu Val Leu Ala Ile Ile Val Phe Ile Phe Ala
890                 895                 900                 905 gtg gtc ggc atg cag ctc ttt ggt aaa agc tac aaa gat tgt gtc tgc    3029
Val Val Gly Met Gln Leu Phe Gly Lys Ser Tyr Lys Asp Cys Val Cys
            910                 915                 920 aag atc gcc agt gat tgt caa ctc cca cgc tgg cac atg aat gac ttc    3077
Lys Ile Ala Ser Asp Cys Gln Leu Pro Arg Trp His Met Asn Asp Phe
        925                 930                 935 ttc cac tcc ttc ctg att gtg ttc cgc gtg ctg tgt ggg gag tgg ata    3125
Phe His Ser Phe Leu Ile Val Phe Arg Val Leu Cys Gly Glu Trp Ile
    940                 945                 950 gag acc atg tgg gac tgt atg gag gtt gct ggt caa gcc atg tgc ctt    3173
Glu Thr Met Trp Asp Cys Met Glu Val Ala Gly Gln Ala Met Cys Leu
955                 960                 965 act gtc ttc atg atg gtc atg gtg att gga aac cta gtg gtc ctg aat    3221
Thr Val Phe Met Met Val Met Val Ile Gly Asn Leu Val Val Leu Asn
970                 975                 980                 985 ctc ttt ctg gcc ttg ctt ctg agc tca ttt agt gca gac aac ctt  gca   3269
Leu Phe Leu Ala Leu Leu Leu Ser Ser Phe Ser Ala Asp Asn Leu  Ala
                990                 995                 1000 gcc act gat gat  gat aat gaa atg aat  aat ctc caa att gct  gtg    3314
Ala Thr Asp Asp  Asp Asn Glu Met Asn  Asn Leu Gln Ile Ala  Val
        1005                 1010                1015 gat agg atg cac  aaa gga gta gct tat  gtg aaa aga aaa ata  tat    3359
Asp Arg Met His  Lys Gly Val Ala Tyr  Val Lys Arg Lys Ile  Tyr
        1020                 1025                1030 gaa ttt att caa  cag tcc ttc att agg  aaa caa aag att tta  gat    3404
Glu Phe Ile Gln  Gln Ser Phe Ile Arg  Lys Gln Lys Ile Leu  Asp
        1035                 1040                1045 gaa att aaa cca  ctt gat gat cta aac  aac aag aaa gac agt  tgt    3449
Glu Ile Lys Pro  Leu Asp Asp Leu Asn  Asn Lys Lys Asp Ser  Cys
        1050                 1055                1060 atg tcc aat cat  aca aca gaa att ggg  aaa gat ctt gac tat  ctt    3494
Met Ser Asn His  Thr Thr Glu Ile Gly  Lys Asp Leu Asp Tyr  Leu
        1065                 1070                1075 aaa gat gta aat  gga act aca agt ggt  ata gga act ggc agc  agt    3539
Lys Asp Val Asn  Gly Thr Thr Ser Gly  Ile Gly Thr Gly Ser  Ser
        1080                 1085                1090 gtt gaa aaa tac  att att gat gaa agt  gat tac atg tca ttc  ata    3584
Val Glu Lys Tyr  Ile Ile Asp Glu Ser  Asp Tyr Met Ser Phe  Ile
        1095                 1100                1105
```

-continued

| | | |
|---|---|---|
| aac aac ccc agt ctt act gtg act gta cca att gct gta gga gaa<br>Asn Asn Pro Ser Leu Thr Val Thr Val Pro Ile Ala Val Gly Glu<br>1110                 1115                1120 | 3629 |
| tct gac ttt gaa aat tta aac acg gaa gac ttt agt agt gaa tcg<br>Ser Asp Phe Glu Asn Leu Asn Thr Glu Asp Phe Ser Ser Glu Ser<br>1125               1130              1135 | 3674 |
| gat ctg gaa gaa agc aaa gag aaa ctg aat gaa agc agt agc tca<br>Asp Leu Glu Glu Ser Lys Glu Lys Leu Asn Glu Ser Ser Ser Ser<br>1140              1145              1150 | 3719 |
| tca gaa ggt agc act gtg gac atc ggc gca cct gta gaa gaa cag<br>Ser Glu Gly Ser Thr Val Asp Ile Gly Ala Pro Val Glu Glu Gln<br>1155              1160              1165 | 3764 |
| ccc gta gtg gaa cct gaa gaa act ctt gaa cca gaa gct tgt ttc<br>Pro Val Val Glu Pro Glu Glu Thr Leu Glu Pro Glu Ala Cys Phe<br>1170              1175              1180 | 3809 |
| act gaa ggc tgt gta caa aga ttc aag tgt tgt caa atc aat gtg<br>Thr Glu Gly Cys Val Gln Arg Phe Lys Cys Cys Gln Ile Asn Val<br>1185              1190              1195 | 3854 |
| gaa gaa ggc aga gga aaa caa tgg tgg aac ctg aga agg acg tgt<br>Glu Glu Gly Arg Gly Lys Gln Trp Trp Asn Leu Arg Arg Thr Cys<br>1200              1205              1210 | 3899 |
| ttc cga ata gtt gaa cat aac tgg ttt gag acc ttc att gtt ttc<br>Phe Arg Ile Val Glu His Asn Trp Phe Glu Thr Phe Ile Val Phe<br>1215              1220              1225 | 3944 |
| atg att ctc ctt agt agt ggt gct ctg gca ttt gaa gat ata tat<br>Met Ile Leu Leu Ser Ser Gly Ala Leu Ala Phe Glu Asp Ile Tyr<br>1230              1235              1240 | 3989 |
| att gat cag cga aag acg att aag acg atg ttg gaa tat gct gac<br>Ile Asp Gln Arg Lys Thr Ile Lys Thr Met Leu Glu Tyr Ala Asp<br>1245              1250              1255 | 4034 |
| aag gtt ttc act tac att ttc att ctg gaa atg ctt cta aaa tgg<br>Lys Val Phe Thr Tyr Ile Phe Ile Leu Glu Met Leu Leu Lys Trp<br>1260              1265              1270 | 4079 |
| gtg gca tat ggc tat caa aca tat ttc acc aat gcc tgg tgt tgg<br>Val Ala Tyr Gly Tyr Gln Thr Tyr Phe Thr Asn Ala Trp Cys Trp<br>1275              1280              1285 | 4124 |
| ctg gac ttc tta att gtt gat gtt tca ttg gtc agt tta aca gca<br>Leu Asp Phe Leu Ile Val Asp Val Ser Leu Val Ser Leu Thr Ala<br>1290              1295              1300 | 4169 |
| aat gcc ttg ggt tac tca gaa ctt gga gcc atc aaa tct ctc agg<br>Asn Ala Leu Gly Tyr Ser Glu Leu Gly Ala Ile Lys Ser Leu Arg<br>1305              1310              1315 | 4214 |
| aca cta aga gct ctg aga cct cta aga gcc tta tct cga ttt gaa<br>Thr Leu Arg Ala Leu Arg Pro Leu Arg Ala Leu Ser Arg Phe Glu<br>1320              1325              1330 | 4259 |
| ggg atg agg gtg gtt gtg aat gcc ctt tta gga gca att cca tcc<br>Gly Met Arg Val Val Val Asn Ala Leu Leu Gly Ala Ile Pro Ser<br>1335              1340              1345 | 4304 |
| atc atg aat gtg ctt ctg gtt tgt ctt ata ttc tgg cta att ttc<br>Ile Met Asn Val Leu Leu Val Cys Leu Ile Phe Trp Leu Ile Phe<br>1350              1355              1360 | 4349 |
| agc atc atg ggc gta aat ttg ttt gct ggc aaa ttc tac cac tgt<br>Ser Ile Met Gly Val Asn Leu Phe Ala Gly Lys Phe Tyr His Cys<br>1365              1370              1375 | 4394 |
| att aac acc aca act ggt gac agg ttt gac atc gaa gac gtg aat<br>Ile Asn Thr Thr Thr Gly Asp Arg Phe Asp Ile Glu Asp Val Asn<br>1380              1385              1390 | 4439 |
| aat cat act gat tgc cta aaa cta ata gaa aga aat gag act gct<br>Asn His Thr Asp Cys Leu Lys Leu Ile Glu Arg Asn Glu Thr Ala<br>1395              1400              1405 | 4484 |

```
cga tgg aaa aat gtg aaa gta aac ttt gat aat gta gga ttt ggg         4529
Arg Trp Lys Asn Val Lys Val Asn Phe Asp Asn Val Gly Phe Gly
        1410            1415                1420 tat ctc tct ttg ctt caa gtt gcc aca ttc aaa gga tgg atg gat         4574
Tyr Leu Ser Leu Leu Gln Val Ala Thr Phe Lys Gly Trp Met Asp
        1425            1430                1435 ata atg tat gca gca gtt gat tcc aga aat gtg gaa ctc cag cct         4619
Ile Met Tyr Ala Ala Val Asp Ser Arg Asn Val Glu Leu Gln Pro
        1440            1445                1450 aag tat gaa aaa agt ctg tac atg tat ctt tac ttt gtt att ttc         4664
Lys Tyr Glu Lys Ser Leu Tyr Met Tyr Leu Tyr Phe Val Ile Phe
        1455            1460                1465 atc atc ttt ggg tcc ttc ttc acc ttg aac ctg ttt att ggt gtc         4709
Ile Ile Phe Gly Ser Phe Phe Thr Leu Asn Leu Phe Ile Gly Val
        1470            1475                1480 atc ata gat aat ttc aac cag cag aaa aag aag ttt gga ggt caa         4754
Ile Ile Asp Asn Phe Asn Gln Gln Lys Lys Lys Phe Gly Gly Gln
        1485            1490                1495 gac atc ttt atg aca gaa gaa cag aag aaa tac tat aat gca atg         4799
Asp Ile Phe Met Thr Glu Glu Gln Lys Lys Tyr Tyr Asn Ala Met
        1500            1505                1510 aaa aaa tta gga tcg aaa aaa ccg caa aag cct ata cct cga cca         4844
Lys Lys Leu Gly Ser Lys Lys Pro Gln Lys Pro Ile Pro Arg Pro
        1515            1520                1525 gga aac aaa ttt caa gga atg gtc ttt gac ttc gta acc aga caa         4889
Gly Asn Lys Phe Gln Gly Met Val Phe Asp Phe Val Thr Arg Gln
        1530            1535                1540 gtt ttt gac ata agc atc atg att ctc atc tgt ctt aac atg gtc         4934
Val Phe Asp Ile Ser Ile Met Ile Leu Ile Cys Leu Asn Met Val
        1545            1550                1555 aca atg atg gtg gaa aca gat gac cag agt gaa tat gtg act acc         4979
Thr Met Met Val Glu Thr Asp Asp Gln Ser Glu Tyr Val Thr Thr
        1560            1565                1570 att ttg tca cgc atc aat ctg gtg ttc att gtg cta ttt act gga         5024
Ile Leu Ser Arg Ile Asn Leu Val Phe Ile Val Leu Phe Thr Gly
        1575            1580                1585 gag tgt gta ctg aaa ctc atc tct cta cgc cat tat tat ttt acc         5069
Glu Cys Val Leu Lys Leu Ile Ser Leu Arg His Tyr Tyr Phe Thr
        1590            1595                1600 att gga tgg aat att ttt gat ttt gtg gtt gtc att ctc tcc att         5114
Ile Gly Trp Asn Ile Phe Asp Phe Val Val Val Ile Leu Ser Ile
        1605            1610                1615 gta ggt atg ttt ctt gcc gag ctg ata gaa aag tat ttc gtg tcc         5159
Val Gly Met Phe Leu Ala Glu Leu Ile Glu Lys Tyr Phe Val Ser
        1620            1625                1630 cct acc ctg ttc cga gtg atc cgt ctt gct agg att ggc cga atc         5204
Pro Thr Leu Phe Arg Val Ile Arg Leu Ala Arg Ile Gly Arg Ile
        1635            1640                1645 cta cgt ctg atc aaa gga gca aag ggg atc cgc acg ctg ctc ttt         5249
Leu Arg Leu Ile Lys Gly Ala Lys Gly Ile Arg Thr Leu Leu Phe
        1650            1655                1660 gct ttg atg atg tcc ctt cct gcg ttg ttt aac atc ggc ctc cta         5294
Ala Leu Met Met Ser Leu Pro Ala Leu Phe Asn Ile Gly Leu Leu
        1665            1670                1675 ctc ttc cta gtc atg ttc atc tac gcc atc ttt ggg atg tcc aac         5339
Leu Phe Leu Val Met Phe Ile Tyr Ala Ile Phe Gly Met Ser Asn
        1680            1685                1690 ttt gcc tat gtt aag agg gaa gtt ggg atc gat gac atg ttc aac         5384
Phe Ala Tyr Val Lys Arg Glu Val Gly Ile Asp Asp Met Phe Asn
        1695            1700                1705
```

```
ttt gag acc ttt ggc aac agc atg atc tgc cta ttc caa att aca         5429
Phe Glu Thr Phe Gly Asn Ser Met Ile Cys Leu Phe Gln Ile Thr
1710                    1715                    1720 acc tct gct ggc tgg gat gga ttg cta gca ccc att ctc aac agt         5474
Thr Ser Ala Gly Trp Asp Gly Leu Leu Ala Pro Ile Leu Asn Ser
        1725                    1730                    1735 aag cca ccc gac tgt gac cct aat aaa gtt aac cct gga agc tca         5519
Lys Pro Pro Asp Cys Asp Pro Asn Lys Val Asn Pro Gly Ser Ser
1740                    1745                    1750 gtt aag gga gac tgt ggg aac cca tct gtt gga att ttc ttt ttt         5564
Val Lys Gly Asp Cys Gly Asn Pro Ser Val Gly Ile Phe Phe Phe
        1755                    1760                    1765 gtc agt tac atc atc ata tcc ttc ctg gtt gtg gtg aac atg tac         5609
Val Ser Tyr Ile Ile Ile Ser Phe Leu Val Val Val Asn Met Tyr
1770                    1775                    1780 atc gcg gtc atc ctg gag aac ttc agt gtt gct act gaa gaa agt         5654
Ile Ala Val Ile Leu Glu Asn Phe Ser Val Ala Thr Glu Glu Ser
        1785                    1790                    1795 gca gag cct ctg agt gag gat gac ttt gag atg ttc tat gag gtt         5699
Ala Glu Pro Leu Ser Glu Asp Asp Phe Glu Met Phe Tyr Glu Val
1800                    1805                    1810 tgg gag aag ttt gat ccc gat gca act cag ttc atg gaa ttt gaa         5744
Trp Glu Lys Phe Asp Pro Asp Ala Thr Gln Phe Met Glu Phe Glu
        1815                    1820                    1825 aaa tta tct cag ttt gca gct gcg ctt gaa ccg cct ctc aat ctg         5789
Lys Leu Ser Gln Phe Ala Ala Ala Leu Glu Pro Pro Leu Asn Leu
1830                    1835                    1840 cca caa cca aac aaa ctc cag ctc att gcc atg gat ttg ccc atg         5834
Pro Gln Pro Asn Lys Leu Gln Leu Ile Ala Met Asp Leu Pro Met
        1845                    1850                    1855 gtg agt ggt gac cgg atc cac tgt ctt gat atc tta ttt gct ttt         5879
Val Ser Gly Asp Arg Ile His Cys Leu Asp Ile Leu Phe Ala Phe
1860                    1865                    1870 aca aag cgg gtt cta gga gag agt gga gag atg gat gct cta cga         5924
Thr Lys Arg Val Leu Gly Glu Ser Gly Glu Met Asp Ala Leu Arg
        1875                    1880                    1885 ata cag atg gaa gag cga ttc atg gct tcc aat cct tcc aag gtc         5969
Ile Gln Met Glu Glu Arg Phe Met Ala Ser Asn Pro Ser Lys Val
1890                    1895                    1900 tcc tat cag cca atc act act act tta aaa cga aaa caa gag gaa         6014
Ser Tyr Gln Pro Ile Thr Thr Thr Leu Lys Arg Lys Gln Glu Glu
        1905                    1910                    1915 gta tct gct gtc att att cag cgt gct tac aga cgc cac ctt tta         6059
Val Ser Ala Val Ile Ile Gln Arg Ala Tyr Arg Arg His Leu Leu
1920                    1925                    1930 aag cga act gta aaa caa gct tcc ttt acg tac aat aaa aac aaa         6104
Lys Arg Thr Val Lys Gln Ala Ser Phe Thr Tyr Asn Lys Asn Lys
        1935                    1940                    1945 atc aaa ggt ggg gct aat ctt ctt ata aaa gaa gac atg ata att         6149
Ile Lys Gly Gly Ala Asn Leu Leu Ile Lys Glu Asp Met Ile Ile
1950                    1955                    1960 gac aga ata aat gaa aac tct att aca gaa aaa act gat ctg acc         6194
Asp Arg Ile Asn Glu Asn Ser Ile Thr Glu Lys Thr Asp Leu Thr
        1965                    1970                    1975 atg tcc act gca gct tgt cca cct tcc tat gac cgg gtg aca aag         6239
Met Ser Thr Ala Ala Cys Pro Pro Ser Tyr Asp Arg Val Thr Lys
1980                    1985                    1990
```

| | |
|---|---|
| cca att gtg gaa aaa cat gag caa gaa ggc aaa gat gaa aaa gcc<br>Pro Ile Val Glu Lys His Glu Gln Glu Gly Lys Asp Glu Lys Ala<br>             1995                2000                2005 | 6284 |
| aaa ggg aaa taa atgaaaataa ataaaaataa ttgggtgaca aattgtttac<br>Lys Gly Lys | 6336 |
| agcctgtgaa ggtgatgtat ttttatcaac aggactcctt taggaggtca atgccaaact | 6396 |
| gactgttttt acacaaatct ccttaaggtc agtgcctaca ataagacagt gaccccttgt | 6456 |
| cagcaaactg tgactctgtg taaaggggag atgaccttga caggaggtta ctgttctcac | 6516 |
| taccagctga cactgctgaa gataagatgc acaatggcta gtcagactgt agggaccagt | 6576 |
| ttcaagggggt gcaaacctgt gattttgggg ttgtttaaca tgaaacactt tagtgtagta | 6636 |
| attgtatcca ctgtttgcat ttcaactgcc acatttgtca catttttatg gaatctgtta | 6696 |
| gtggattcat cttttttgtta atccatgtgt ttattatatg tgactatttt tgtaaacgaa | 6756 |
| gtttctgttg agaaataggc taaggacctc tataacaggt atgccacctg gggggtatgg | 6816 |
| caaccacatg gccctcccag ctacacaaag tcgtggtttg catgagggca tgctgcactt | 6876 |
| agagatcatg catgagaaaa agtcacaaga aaaacaaatt cttaaatttc accatatttc | 6936 |
| tgggagggt aattgggtga taagtggagg tgctttgttg atcttgtttt gcgaaatcca | 6996 |
| gcccctagac caagtagatt atttgtgggt aggccagtaa atcttagcag gtgcaaactt | 7056 |
| cattcaaatg tttggagtca taaatgttat gtttctttt gttgtattaa aaaaaaacc | 7116 |
| tgaatagtga atattgcccc tcaccctcca ccgccagaag actgaattga ccaaaattac | 7176 |
| tctttataaa tttctgcttt ttcctgcact tgtttagcc atctttgggc tctcagcaag | 7236 |
| gttgacactg tatatgttaa tgaaatgcta tttattatgt aaatagtcat tttaccctgt | 7296 |
| ggtgcacgtt tgagcaaaca aataatgacc taagcacagt atttattgca tcaaatatgt | 7356 |
| accacaagaa atgtagagtg caagctttac acaggtaata aaatgtattc tgtaccattt | 7416 |
| atagatagtt tggatgctat caatgcatgt ttatattacc atgctgctgt atctggtttc | 7476 |
| tctcactgct cagaatctca tttatgagaa accatatgtc agtggtaaag tcaaggaaat | 7536 |
| tgttcaacag atctcattta tttaagtcat taagcaatag tttgcagcac tttaacagct | 7596 |
| ttttggttat ttttacattt taagtggata acatatggta tatagccaga ctgtacagac | 7656 |
| atgtttaaaa aaacacactg cttaacctat taaatatgtg tttagaattt tataagcaaa | 7716 |
| tataaatact gtaaaagtc actttatttt attttttcagc attatgtaca taaatatgaa | 7776 |
| gaggaaatta tcttcaggtt gatatcacaa tcacttttct tactttctgt ccatagtact | 7836 |
| ttttcatgaa agaaatttgc taaataagac atgaaaacaa gactgggtag ttgtagattt | 7896 |
| ctgctttta aattacattt gctaatttta gattatttca caatttttaag gagcaaaata | 7956 |
| ggttcacgat tcatatccaa attatgcttt gcaattggaa aagggtttaa aattttattt | 8016 |
| atatttctgg tagtacctgt actaactgaa ttgaaggtag tgcttatgtt attttttgttc | 8076 |
| ttttttttctg acttcggttt atgttttcat ttctttggag taatgctgct ctagattgtt | 8136 |
| ctaaatagaa tgtgggcttc ataatttttt tttccacaaa aacagagtag tcaacttata | 8196 |
| tagtcaatta catcaggaca ttttgtgttt cttacagaag caaaccatag gctcctcttt | 8256 |
| tccttaaaac tacttagata aactgtattc gtgaactgca tgctggaaaa tgctactatt | 8316 |
| atgctaaata atgctaacca acatttaaaa tgtgcaaaac taataaagat tacatttttt | 8376 |
| atttt | 8381 |

-continued

<210> SEQ ID NO 2
<211> LENGTH: 2009
<212> TYPE: PRT
<213> ORGANISM: Homo sapiens

<400> SEQUENCE: 2

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Val Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380
```

-continued

```
Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
                500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
                580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
        610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
        770                 775                 780

Met Ala Met Glu His Tyr Pro Met Thr Asp His Phe Asn Asn Val Leu
785                 790                 795                 800
```

-continued

```
Thr Val Gly Asn Leu Val Phe Thr Gly Ile Phe Thr Ala Glu Met Phe
            805                 810                 815

Leu Lys Ile Ile Ala Met Asp Pro Tyr Tyr Phe Gln Glu Gly Trp
            820                 825             830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
            995                 1000                1005

Met Asn Asn Leu Gln Ile Ala Val Asp Arg Met His Lys Gly Val
        1010                1015                1020

Ala Tyr Val Lys Arg Lys Ile Tyr Glu Phe Ile Gln Gln Ser Phe
        1025                1030                1035

Ile Arg Lys Gln Lys Ile Leu Asp Glu Ile Lys Pro Leu Asp Asp
        1040                1045                1050

Leu Asn Asn Lys Lys Asp Ser Cys Met Ser Asn His Thr Thr Glu
        1055                1060                1065

Ile Gly Lys Asp Leu Asp Tyr Leu Lys Asp Val Asn Gly Thr Thr
        1070                1075                1080

Ser Gly Ile Gly Thr Gly Ser Ser Val Glu Lys Tyr Ile Ile Asp
        1085                1090                1095

Glu Ser Asp Tyr Met Ser Phe Ile Asn Asn Pro Ser Leu Thr Val
        1100                1105                1110

Thr Val Pro Ile Ala Val Gly Glu Ser Asp Phe Glu Asn Leu Asn
        1115                1120                1125

Thr Glu Asp Phe Ser Ser Glu Ser Asp Leu Glu Glu Ser Lys Glu
        1130                1135                1140

Lys Leu Asn Glu Ser Ser Ser Ser Ser Glu Gly Ser Thr Val Asp
        1145                1150                1155

Ile Gly Ala Pro Val Glu Glu Gln Pro Val Val Glu Pro Glu Glu
        1160                1165                1170

Thr Leu Glu Pro Glu Ala Cys Phe Thr Glu Gly Cys Val Gln Arg
        1175                1180                1185

Phe Lys Cys Cys Gln Ile Asn Val Glu Glu Gly Arg Gly Lys Gln
        1190                1195                1200
```

-continued

| | | | | | | | | | | |
|---|---|---|---|---|---|---|---|---|---|---|
| Trp | Trp | Asn | Leu | Arg | Arg | Thr | Cys | Phe | Arg | Ile | Val | Glu | His | Asn |
| 1205 | | | | 1210 | | | | | 1215 | |
| Trp | Phe | Glu | Thr | Phe | Ile | Val | Phe | Met | Ile | Leu | Leu | Ser | Ser | Gly |
| 1220 | | | | | 1225 | | | | 1230 | |
| Ala | Leu | Ala | Phe | Glu | Asp | Ile | Tyr | Ile | Asp | Gln | Arg | Lys | Thr | Ile |
| 1235 | | | | | 1240 | | | | 1245 | |
| Lys | Thr | Met | Leu | Glu | Tyr | Ala | Asp | Lys | Val | Phe | Thr | Tyr | Ile | Phe |
| 1250 | | | | | 1255 | | | | 1260 | |
| Ile | Leu | Glu | Met | Leu | Leu | Lys | Trp | Val | Ala | Tyr | Gly | Tyr | Gln | Thr |
| 1265 | | | | | 1270 | | | | 1275 | |
| Tyr | Phe | Thr | Asn | Ala | Trp | Cys | Trp | Leu | Asp | Phe | Leu | Ile | Val | Asp |
| 1280 | | | | | 1285 | | | | 1290 | |
| Val | Ser | Leu | Val | Ser | Leu | Thr | Ala | Asn | Ala | Leu | Gly | Tyr | Ser | Glu |
| 1295 | | | | | 1300 | | | | 1305 | |
| Leu | Gly | Ala | Ile | Lys | Ser | Leu | Arg | Thr | Leu | Arg | Ala | Leu | Arg | Pro |
| 1310 | | | | | 1315 | | | | 1320 | |
| Leu | Arg | Ala | Leu | Ser | Arg | Phe | Glu | Gly | Met | Arg | Val | Val | Val | Asn |
| 1325 | | | | | 1330 | | | | 1335 | |
| Ala | Leu | Leu | Gly | Ala | Ile | Pro | Ser | Ile | Met | Asn | Val | Leu | Leu | Val |
| 1340 | | | | | 1345 | | | | 1350 | |
| Cys | Leu | Ile | Phe | Trp | Leu | Ile | Phe | Ser | Ile | Met | Gly | Val | Asn | Leu |
| 1355 | | | | | 1360 | | | | 1365 | |
| Phe | Ala | Gly | Lys | Phe | Tyr | His | Cys | Ile | Asn | Thr | Thr | Thr | Gly | Asp |
| 1370 | | | | | 1375 | | | | 1380 | |
| Arg | Phe | Asp | Ile | Glu | Asp | Val | Asn | Asn | His | Thr | Asp | Cys | Leu | Lys |
| 1385 | | | | | 1390 | | | | 1395 | |
| Leu | Ile | Glu | Arg | Asn | Glu | Thr | Ala | Arg | Trp | Lys | Asn | Val | Lys | Val |
| 1400 | | | | | 1405 | | | | 1410 | |
| Asn | Phe | Asp | Asn | Val | Gly | Phe | Gly | Tyr | Leu | Ser | Leu | Leu | Gln | Val |
| 1415 | | | | | 1420 | | | | 1425 | |
| Ala | Thr | Phe | Lys | Gly | Trp | Met | Asp | Ile | Met | Tyr | Ala | Ala | Val | Asp |
| 1430 | | | | | 1435 | | | | 1440 | |
| Ser | Arg | Asn | Val | Glu | Leu | Gln | Pro | Lys | Tyr | Glu | Lys | Ser | Leu | Tyr |
| 1445 | | | | | 1450 | | | | 1455 | |
| Met | Tyr | Leu | Tyr | Phe | Val | Ile | Phe | Ile | Ile | Phe | Gly | Ser | Phe | Phe |
| 1460 | | | | | 1465 | | | | 1470 | |
| Thr | Leu | Asn | Leu | Phe | Ile | Gly | Val | Ile | Ile | Asp | Asn | Phe | Asn | Gln |
| 1475 | | | | | 1480 | | | | 1485 | |
| Gln | Lys | Lys | Lys | Phe | Gly | Gly | Gln | Asp | Ile | Phe | Met | Thr | Glu | Glu |
| 1490 | | | | | 1495 | | | | 1500 | |
| Gln | Lys | Lys | Tyr | Tyr | Asn | Ala | Met | Lys | Lys | Leu | Gly | Ser | Lys | Lys |
| 1505 | | | | | 1510 | | | | 1515 | |
| Pro | Gln | Lys | Pro | Ile | Pro | Arg | Pro | Gly | Asn | Lys | Phe | Gln | Gly | Met |
| 1520 | | | | | 1525 | | | | 1530 | |
| Val | Phe | Asp | Phe | Val | Thr | Arg | Gln | Val | Phe | Asp | Ile | Ser | Ile | Met |
| 1535 | | | | | 1540 | | | | 1545 | |
| Ile | Leu | Ile | Cys | Leu | Asn | Met | Val | Thr | Met | Met | Val | Glu | Thr | Asp |
| 1550 | | | | | 1555 | | | | 1560 | |
| Asp | Gln | Ser | Glu | Tyr | Val | Thr | Ile | Leu | Ser | Arg | Ile | Asn | Leu |
| 1565 | | | | | 1570 | | | | 1575 | |
| Val | Phe | Ile | Val | Leu | Phe | Thr | Gly | Glu | Cys | Val | Leu | Lys | Leu | Ile |
| 1580 | | | | | 1585 | | | | 1590 | |

-continued

| | | | | | | | | | | | |
|---|---|---|---|---|---|---|---|---|---|---|---|
| Ser | Leu | Arg | His | Tyr | Tyr | Phe | Thr | Ile | Gly | Trp | Asn | Ile | Phe | Asp |
| 1595 | | | | | 1600 | | | | 1605 | | |

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
1640                1645                1650

Lys Gly Ile Arg Thr Leu Leu Phe Ala Leu Met Met Ser Leu Pro
1655                1660                1665

Ala Leu Phe Asn Ile Gly Leu Leu Leu Phe Leu Val Met Phe Ile
1670                1675                1680

Tyr Ala Ile Phe Gly Met Ser Asn Phe Ala Tyr Val Lys Arg Glu
1685                1690                1695

Val Gly Ile Asp Asp Met Phe Asn Phe Glu Thr Phe Gly Asn Ser
1700                1705                1710

Met Ile Cys Leu Phe Gln Ile Thr Thr Ser Ala Gly Trp Asp Gly
1715                1720                1725

Leu Leu Ala Pro Ile Leu Asn Ser Lys Pro Pro Asp Cys Asp Pro
1730                1735                1740

Asn Lys Val Asn Pro Gly Ser Ser Val Lys Gly Asp Cys Gly Asn
1745                1750                1755

Pro Ser Val Gly Ile Phe Phe Phe Val Ser Tyr Ile Ile Ile Ser
1760                1765                1770

Phe Leu Val Val Val Asn Met Tyr Ile Ala Val Ile Leu Glu Asn
1775                1780                1785

Phe Ser Val Ala Thr Glu Glu Ser Ala Glu Pro Leu Ser Glu Asp
1790                1795                1800

Asp Phe Glu Met Phe Tyr Glu Val Trp Glu Lys Phe Asp Pro Asp
1805                1810                1815

Ala Thr Gln Phe Met Glu Phe Glu Lys Leu Ser Gln Phe Ala Ala
1820                1825                1830

Ala Leu Glu Pro Pro Leu Asn Leu Pro Gln Pro Asn Lys Leu Gln
1835                1840                1845

Leu Ile Ala Met Asp Leu Pro Met Val Ser Gly Asp Arg Ile His
1850                1855                1860

Cys Leu Asp Ile Leu Phe Ala Phe Thr Lys Arg Val Leu Gly Glu
1865                1870                1875

Ser Gly Glu Met Asp Ala Leu Arg Ile Gln Met Glu Glu Arg Phe
1880                1885                1890

Met Ala Ser Asn Pro Ser Lys Val Ser Tyr Gln Pro Ile Thr Thr
1895                1900                1905

Thr Leu Lys Arg Lys Gln Glu Glu Val Ser Ala Val Ile Ile Gln
1910                1915                1920

Arg Ala Tyr Arg Arg His Leu Leu Lys Arg Thr Val Lys Gln Ala
1925                1930                1935

Ser Phe Thr Tyr Asn Lys Asn Lys Ile Lys Gly Gly Ala Asn Leu
1940                1945                1950

Leu Ile Lys Glu Asp Met Ile Ile Asp Arg Ile Asn Glu Asn Ser
1955                1960                1965

Ile Thr Glu Lys Thr Asp Leu Thr Met Ser Thr Ala Ala Cys Pro
1970                1975                1980

|  |  |
|---|---|
| Pro Ser Tyr Asp Arg Val Thr Lys Pro Ile Val Glu Lys His Glu<br>    1985                         1990                         1995 | |
| Gln Glu Gly Lys Asp Glu Lys Ala Lys Gly Lys<br>    2000                         2005 | |

<210> SEQ ID NO 3
<211> LENGTH: 8381
<212> TYPE: DNA
<213> ORGANISM: Homo sapiens
<220> FEATURE:
<221> NAME/KEY: CDS
<222> LOCATION: (267)..(6296)

<400> SEQUENCE: 3

| | |
|---|---:|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |
| ttcctcactg cagatggata atttttcctttt taatcaggaa tttcatatgc agaataaatg | 240 |
| gtaattaaaa tgtgcaggat gacaag atg gag caa aca gtg ctt gta cca cca | 293 |
|                                          Met Glu Gln Thr Val Leu Val Pro Pro<br>                                           1                          5 | |
| gga cct gac agc ttc aac ttc ttc acc aga gaa tct ctt gcg gct att<br>Gly Pro Asp Ser Phe Asn Phe Phe Thr Arg Glu Ser Leu Ala Ala Ile<br>10                        15                      20                      25 | 341 |
| gaa aga cgc att gca gaa gaa aag gca aag aat ccc aaa cca gac aaa<br>Glu Arg Arg Ile Ala Glu Glu Lys Ala Lys Asn Pro Lys Pro Asp Lys<br>                     30                      35                      40 | 389 |
| aaa gat gac gac gaa aat ggc cca aag cca aat agt gac ttg gaa gct<br>Lys Asp Asp Asp Glu Asn Gly Pro Lys Pro Asn Ser Asp Leu Glu Ala<br>                  45                      50                      55 | 437 |
| gga aag aac ctt cca ttt att tat gga gac att cct cca gag atg gtg<br>Gly Lys Asn Leu Pro Phe Ile Tyr Gly Asp Ile Pro Pro Glu Met Val<br>       60                      65                      70 | 485 |
| tca gag ccc ctg gag gac ctg gac ccc tac tat atc aat aag aaa act<br>Ser Glu Pro Leu Glu Asp Leu Asp Pro Tyr Tyr Ile Asn Lys Lys Thr<br>75                        80                      85 | 533 |
| ttt ata gta ttg aat aaa ttg aag gcc atc ttc cgg ttc agt gcc acc<br>Phe Ile Val Leu Asn Lys Leu Lys Ala Ile Phe Arg Phe Ser Ala Thr<br>90                        95                    100                105 | 581 |
| tct gcc ctg tac att tta act ccc ttc aat cct ctt agg aaa ata gct<br>Ser Ala Leu Tyr Ile Leu Thr Pro Phe Asn Pro Leu Arg Lys Ile Ala<br>                  110                    115                  120 | 629 |
| att aag att ttg gta cat tca tta ttc agc atg cta att atg tgc act<br>Ile Lys Ile Leu Val His Ser Leu Phe Ser Met Leu Ile Met Cys Thr<br>         125                      130                    135 | 677 |
| att ttg aca aac tgt gtg ttt atg aca atg agt aac cct cct gat tgg<br>Ile Leu Thr Asn Cys Val Phe Met Thr Met Ser Asn Pro Pro Asp Trp<br>                 140                    145                  150 | 725 |
| aca aag aat gta gaa tac acc ttc aca gga ata tat act ttt gaa tca<br>Thr Lys Asn Val Glu Tyr Thr Phe Thr Gly Ile Tyr Thr Phe Glu Ser<br>     155                      160                    165 | 773 |
| ctt ata aaa att att gca agg gga ttc tgt tta gaa gat ttt act ttc<br>Leu Ile Lys Ile Ile Ala Arg Gly Phe Cys Leu Glu Asp Phe Thr Phe<br>170                      175                    180                185 | 821 |
| ctt cgg gat cca tgg aac tgg ctc gat ttc act gtc att aca ttt gcg<br>Leu Arg Asp Pro Trp Asn Trp Leu Asp Phe Thr Val Ile Thr Phe Ala<br>                 190                    195                  200 | 869 |

-continued

| | |
|---|---|
| tac gtc aca gag ttt gtg gac ctg ggc aat gtc tcg gca ttg aga aca<br>Tyr Val Thr Glu Phe Val Asp Leu Gly Asn Val Ser Ala Leu Arg Thr<br>205 210 215 | 917 |
| ttc aga gtt ctc cga gca ttg aag acg att tca gtc att cca ggc ctg<br>Phe Arg Val Leu Arg Ala Leu Lys Thr Ile Ser Val Ile Pro Gly Leu<br>220 225 230 | 965 |
| aaa acc att gtg gga gcc ctg atc cag tct gtg aag aag ctc tca gat<br>Lys Thr Ile Val Gly Ala Leu Ile Gln Ser Val Lys Lys Leu Ser Asp<br>235 240 245 | 1013 |
| gta atg atc ctg act gtg ttc tgt ctg agc gta ttt gct cta att ggg<br>Val Met Ile Leu Thr Val Phe Cys Leu Ser Val Phe Ala Leu Ile Gly<br>250 255 260 265 | 1061 |
| ctg cag ctg ttc atg ggc aac ctg agg aat aaa tgt ata caa tgg cct<br>Leu Gln Leu Phe Met Gly Asn Leu Arg Asn Lys Cys Ile Gln Trp Pro<br>270 275 280 | 1109 |
| ccc acc aat gct tcc ttg gag gaa cat agt ata gaa aag aat ata act<br>Pro Thr Asn Ala Ser Leu Glu Glu His Ser Ile Glu Lys Asn Ile Thr<br>285 290 295 | 1157 |
| gtg aat tat aat ggt aca ctt ata aat gaa act gtc ttt gag ttt gac<br>Val Asn Tyr Asn Gly Thr Leu Ile Asn Glu Thr Val Phe Glu Phe Asp<br>300 305 310 | 1205 |
| tgg aag tca tat att caa gat tca aga tat cat tat ttc ctg gag ggt<br>Trp Lys Ser Tyr Ile Gln Asp Ser Arg Tyr His Tyr Phe Leu Glu Gly<br>315 320 325 | 1253 |
| ttt tta gat gca cta cta tgt gga aat agc tct gat gca ggc caa tgt<br>Phe Leu Asp Ala Leu Leu Cys Gly Asn Ser Ser Asp Ala Gly Gln Cys<br>330 335 340 345 | 1301 |
| cca gag gga tat atg tgt gtg aaa gct ggt aga aat ccc aat tat ggc<br>Pro Glu Gly Tyr Met Cys Val Lys Ala Gly Arg Asn Pro Asn Tyr Gly<br>350 355 360 | 1349 |
| tac aca agc ttt gat acc ttc agt tgg gct ttt ttg tcc ttg ttt cga<br>Tyr Thr Ser Phe Asp Thr Phe Ser Trp Ala Phe Leu Ser Leu Phe Arg<br>365 370 375 | 1397 |
| cta atg act cag gac ttc tgg gaa aat ctt tat caa ctg aca tta cgt<br>Leu Met Thr Gln Asp Phe Trp Glu Asn Leu Tyr Gln Leu Thr Leu Arg<br>380 385 390 | 1445 |
| gct gct ggg aaa acg tac atg ata ttt ttt gta ttg gtc att ttc ttg<br>Ala Ala Gly Lys Thr Tyr Met Ile Phe Phe Val Leu Val Ile Phe Leu<br>395 400 405 | 1493 |
| ggc tca ttc tac cta ata aat ttg atc ctg gct gtg gtg gcc atg gcc<br>Gly Ser Phe Tyr Leu Ile Asn Leu Ile Leu Ala Val Val Ala Met Ala<br>410 415 420 425 | 1541 |
| tac gag gaa cag aat cag gcc acc ttg gaa gaa gca gaa cag aaa gag<br>Tyr Glu Glu Gln Asn Gln Ala Thr Leu Glu Glu Ala Glu Gln Lys Glu<br>430 435 440 | 1589 |
| gcc gaa ttt cag cag atg att gaa cag ctt aaa aag caa cag gag gca<br>Ala Glu Phe Gln Gln Met Ile Glu Gln Leu Lys Lys Gln Gln Glu Ala<br>445 450 455 | 1637 |
| gct cag cag gca gca acg gca act gcc tca gaa cat tcc aga gag ccc<br>Ala Gln Gln Ala Ala Thr Ala Thr Ala Ser Glu His Ser Arg Glu Pro<br>460 465 470 | 1685 |
| agt gca gca ggc agg ctc tca gac agc tca tct gaa gcc tct aag ttg<br>Ser Ala Ala Gly Arg Leu Ser Asp Ser Ser Ser Glu Ala Ser Lys Leu<br>475 480 485 | 1733 |
| agt tcc aag agt gct aag gaa aga aga aat cgg agg aag aaa aga aaa<br>Ser Ser Lys Ser Ala Lys Glu Arg Arg Asn Arg Arg Lys Lys Arg Lys<br>490 495 500 505 | 1781 |
| cag aaa gag cag tct ggt ggg gaa gag aaa gat gag gat gaa ttc caa<br>Gln Lys Glu Gln Ser Gly Gly Glu Glu Lys Asp Glu Asp Glu Phe Gln<br>510 515 520 | 1829 |

```
                                                           -continued aaa tct gaa tct gag gac agc atc agg agg aaa ggt ttt cgc ttc tcc          1877
Lys Ser Glu Ser Glu Asp Ser Ile Arg Arg Lys Gly Phe Arg Phe Ser
        525                 530                 535 att gaa ggg aac cga ttg aca tat gaa aag agg tac tcc tcc cca cac          1925
Ile Glu Gly Asn Arg Leu Thr Tyr Glu Lys Arg Tyr Ser Ser Pro His
540                 545                 550 cag tct ttg ttg agc atc cgt ggc tcc cta ttt tca cca agg cga aat          1973
Gln Ser Leu Leu Ser Ile Arg Gly Ser Leu Phe Ser Pro Arg Arg Asn
    555                 560                 565 agc aga aca agc ctt ttc agc ttt aga ggg cga gca aag gat gtg gga          2021
Ser Arg Thr Ser Leu Phe Ser Phe Arg Gly Arg Ala Lys Asp Val Gly
570                 575                 580                 585 tct gag aac gac ttc gca gat gat gag cac agc acc ttt gag gat aac          2069
Ser Glu Asn Asp Phe Ala Asp Asp Glu His Ser Thr Phe Glu Asp Asn
                590                 595                 600 gag agc cgt aga gat tcc ttg ttt gtg ccc cga cga cac gga gag aga          2117
Glu Ser Arg Arg Asp Ser Leu Phe Val Pro Arg Arg His Gly Glu Arg
            605                 610                 615 cgc aac agc aac ctg agt cag acc agt agg tca tcc cgg atg ctg gca          2165
Arg Asn Ser Asn Leu Ser Gln Thr Ser Arg Ser Ser Arg Met Leu Ala
        620                 625                 630 gtg ttt cca gcg aat ggg aag atg cac agc act gtg gat tgc aat ggt          2213
Val Phe Pro Ala Asn Gly Lys Met His Ser Thr Val Asp Cys Asn Gly
635                 640                 645 gtg gtt tcc ttg gtt ggt gga cct tca gtt cct aca tcg cct gtt gga          2261
Val Val Ser Leu Val Gly Gly Pro Ser Val Pro Thr Ser Pro Val Gly
650                 655                 660                 665 cag ctt ctg cca gag gtg ata ata gat aag cca gct act gat gac aat          2309
Gln Leu Leu Pro Glu Val Ile Ile Asp Lys Pro Ala Thr Asp Asp Asn
                670                 675                 680 gga aca acc act gaa act gaa atg aga aag aga agg tca agt tct ttc          2357
Gly Thr Thr Thr Glu Thr Glu Met Arg Lys Arg Arg Ser Ser Ser Phe
            685                 690                 695 cac gtt tcc atg gac ttt cta gaa gat cct tcc caa agg caa cga gca          2405
His Val Ser Met Asp Phe Leu Glu Asp Pro Ser Gln Arg Gln Arg Ala
        700                 705                 710 atg agt ata gcc agc att cta aca aat aca gta gaa gaa ctt gaa gaa          2453
Met Ser Ile Ala Ser Ile Leu Thr Asn Thr Val Glu Glu Leu Glu Glu
715                 720                 725 tcc agg cag aaa tgc cca ccc tgt tgg tat aaa ttt tcc aac ata ttc          2501
Ser Arg Gln Lys Cys Pro Pro Cys Trp Tyr Lys Phe Ser Asn Ile Phe
730                 735                 740                 745 tta atc tgg gac tgt tct cca tat tgg tta aaa gtg aaa cat gtt gtc          2549
Leu Ile Trp Asp Cys Ser Pro Tyr Trp Leu Lys Val Lys His Val Val
                750                 755                 760 aac ctg gtt gtg atg gac cca ttt gtt gac ctg gcc atc acc atc tgt          2597
Asn Leu Val Val Met Asp Pro Phe Val Asp Leu Ala Ile Thr Ile Cys
            765                 770                 775 att gtc tta aat act ctt ttc atg gcc atg gag cac tat cca atg acg          2645
Ile Val Leu Asn Thr Leu Phe Met Ala Met Glu His Tyr Pro Met Thr
        780                 785                 790 gac cat ttc aat aat gtg ctt aca gta gga aac ttg gtt ttc act ggg          2693
Asp His Phe Asn Asn Val Leu Thr Val Gly Asn Leu Val Phe Thr Gly
795                 800                 805 atc ttt aca gca gaa atg ttt ctg aaa att att gcc atg gat cct tac          2741
Ile Phe Thr Ala Glu Met Phe Leu Lys Ile Ile Ala Met Asp Pro Tyr
810                 815                 820                 825 tat tat ttc caa gaa ggc tgg aat atc ttt gac ggt ttt att gtg acg          2789
Tyr Tyr Phe Gln Glu Gly Trp Asn Ile Phe Asp Gly Phe Ile Val Thr
                830                 835                 840
```

|  |  |  |  |  |  |  |  |  |  |  |  |  |  |  |  |
|---|---|---|---|---|---|---|---|---|---|---|---|---|---|---|---|
| ctt | agc | ctg | gta | gaa | ctt | gga | ctc | gcc | aat | gtg | gaa | gga | tta | tct | gtt |
| Leu | Ser | Leu | Val | Glu | Leu | Gly | Leu | Ala | Asn | Val | Glu | Gly | Leu | Ser | Val |
|  |  | 845 |  |  |  | 850 |  |  |  |  | 855 |  |  |  |  |

2837 ctc cgt tca ttt cga ttg ctg cga gtt ttc aag ttg gca aaa tct tgg
Leu Arg Ser Phe Arg Leu Leu Arg Val Phe Lys Leu Ala Lys Ser Trp
        860                 865                     870

2885 cca acg tta aat atg cta ata aag atc atc ggc aat tcc gtg ggg gct
Pro Thr Leu Asn Met Leu Ile Lys Ile Ile Gly Asn Ser Val Gly Ala
    875                 880                 885

2933 ctg gga aat tta acc ctc gtc ttg gcc atc atc gtc ttc att ttt gcc
Leu Gly Asn Leu Thr Leu Val Leu Ala Ile Ile Val Phe Ile Phe Ala
890                 895                 900                 905

2981 gtg gtc ggc atg cag ctc ttt ggt aaa agc tac aaa gat tgt gtc tgc
Val Val Gly Met Gln Leu Phe Gly Lys Ser Tyr Lys Asp Cys Val Cys
            910                 915                 920

3029 aag atc gcc agt gat tgt caa ctc cca cgc tgg cac atg aat gac ttc
Lys Ile Ala Ser Asp Cys Gln Leu Pro Arg Trp His Met Asn Asp Phe
        925                 930                 935

3077 ttc cac tcc ttc ctg att gtg ttc cgc gtg ctg tgt ggg gag tgg ata
Phe His Ser Phe Leu Ile Val Phe Arg Val Leu Cys Gly Glu Trp Ile
    940                 945                 950

3125 gag acc atg tgg gac tgt atg gag gtt gct ggt caa gcc atg tgc ctt
Glu Thr Met Trp Asp Cys Met Glu Val Ala Gly Gln Ala Met Cys Leu
955                 960                 965

3173 act gtc ttc atg atg gtc atg gtg att gga aac cta gtg gtc ctg aat
Thr Val Phe Met Met Val Met Val Ile Gly Asn Leu Val Val Leu Asn
970                 975                 980                 985

3221 ctc ttt ctg gcc ttg ctt ctg agc tca ttt agt gca gac aac ctt  gca
Leu Phe Leu Ala Leu Leu Leu Ser Ser Phe Ser Ala Asp Asn Leu  Ala
            990                 995                 1000

3269 gcc act gat gat gat aat gaa atg aat aat ctc caa att gct gtg
Ala Thr Asp Asp Asp Asn Glu Met Asn Asn Leu Gln Ile Ala Val
        1005                1010                1015

3314 gat agg atg cac aaa gga gta gct tat gtg aaa aga aaa ata tat
Asp Arg Met His Lys Gly Val Ala Tyr Val Lys Arg Lys Ile Tyr
    1020                1025                1030

3359 gaa ttt att caa cag tcc ttc att agg aaa caa aag att tta gat
Glu Phe Ile Gln Gln Ser Phe Ile Arg Lys Gln Lys Ile Leu Asp
1035                1040                1045

3404 gaa att aaa cca ctt gat gat cta aac aac aag aaa gac agt tgt
Glu Ile Lys Pro Leu Asp Asp Leu Asn Asn Lys Lys Asp Ser Cys
        1050                1055                1060

3449 atg tcc aat cat aca aca gaa att ggg aaa gat ctt gac tat ctt
Met Ser Asn His Thr Thr Glu Ile Gly Lys Asp Leu Asp Tyr Leu
    1065                1070                1075

3494 aaa gat gta aat gga act aca agt ggt ata gga act ggc agc agt
Lys Asp Val Asn Gly Thr Thr Ser Gly Ile Gly Thr Gly Ser Ser
1080                1085                1090

3539 gtt gaa aaa tac att att gat gaa agt gat tac atg tca ttc ata
Val Glu Lys Tyr Ile Ile Asp Glu Ser Asp Tyr Met Ser Phe Ile
        1095                1100                1105

3584 aac aac ccc agt ctt act gtg act gta cca att gct gta gga gaa
Asn Asn Pro Ser Leu Thr Val Thr Val Pro Ile Ala Val Gly Glu
    1110                1115                1120

3629 tct gac ttt gaa aat tta aac acg gaa gac ttt agt agt gaa tcg
Ser Asp Phe Glu Asn Leu Asn Thr Glu Asp Phe Ser Ser Glu Ser
1125                1130                1135

3674 gat ctg gaa gaa agc aaa gag aaa ctg aat gaa agc agt agc tca
Asp Leu Glu Glu Ser Lys Glu Lys Leu Asn Glu Ser Ser Ser Ser
        1140                1145                1150

3719

```
                                                        -continued tca gaa ggt agc  act gtg gac atc  ggc gca cct gta  gaa gaa cag          3764
Ser Glu Gly Ser  Thr Val Asp Ile  Gly Ala Pro Val  Glu Glu Gln
            1155              1160              1165 ccc gta gtg gaa  cct gaa gaa act  ctt gaa cca gaa  gct tgt ttc          3809
Pro Val Val Glu  Pro Glu Glu Thr  Leu Glu Pro Glu  Ala Cys Phe
        1170              1175              1180 act gaa ggc tgt  gta caa aga ttc  aag tgt tgt caa  atc aat gtg          3854
Thr Glu Gly Cys  Val Gln Arg Phe  Lys Cys Cys Gln  Ile Asn Val
        1185              1190              1195 gaa gaa ggc aga  gga aaa caa tgg  tgg aac ctg aga  agg acg tgt          3899
Glu Glu Gly Arg  Gly Lys Gln Trp  Trp Asn Leu Arg  Arg Thr Cys
        1200              1205              1210 ttc cga ata gtt  gaa cat aac tgg  ttt gag acc ttc  att gtt ttc          3944
Phe Arg Ile Val  Glu His Asn Trp  Phe Glu Thr Phe  Ile Val Phe
            1215              1220              1225 atg att ctc ctt  agt agt ggt gct  ctg gca ttt gaa  gat ata tat          3989
Met Ile Leu Leu  Ser Ser Gly Ala  Leu Ala Phe Glu  Asp Ile Tyr
        1230              1235              1240 att gat cag cga  aag acg att aag  acg atg ttg gaa  tat gct gac          4034
Ile Asp Gln Arg  Lys Thr Ile Lys  Thr Met Leu Glu  Tyr Ala Asp
        1245              1250              1255 aag gtt ttc act  tac att ttc att  ctg gaa atg ctt  cta aaa tgg          4079
Lys Val Phe Thr  Tyr Ile Phe Ile  Leu Glu Met Leu  Leu Lys Trp
        1260              1265              1270 gtg gca tat ggc  tat caa aca tat  ttc acc aat gcc  tgg tgt tgg          4124
Val Ala Tyr Gly  Tyr Gln Thr Tyr  Phe Thr Asn Ala  Trp Cys Trp
        1275              1280              1285 ctg gac ttc tta  att gtt gat gtt  tca ttg gtc agt  tta aca gca          4169
Leu Asp Phe Leu  Ile Val Asp Val  Ser Leu Val Ser  Leu Thr Ala
        1290              1295              1300 aat gcc ttg ggt  tac tca gaa ctt  gga gcc atc aaa  tct ctc agg          4214
Asn Ala Leu Gly  Tyr Ser Glu Leu  Gly Ala Ile Lys  Ser Leu Arg
        1305              1310              1315 aca cta aga gct  ctg aga cct cta  aga gcc tta tct  cga ttt gaa          4259
Thr Leu Arg Ala  Leu Arg Pro Leu  Arg Ala Leu Ser  Arg Phe Glu
        1320              1325              1330 ggg atg agg gtg  gtt gtg aat gcc  ctt tta gga gca  att cca tcc          4304
Gly Met Arg Val  Val Val Asn Ala  Leu Leu Gly Ala  Ile Pro Ser
        1335              1340              1345 atc atg aat gtg  ctt ctg ctt tgt  ctt ata ttc tgg  cta att ttc          4349
Ile Met Asn Val  Leu Leu Leu Cys  Leu Ile Phe Trp  Leu Ile Phe
        1350              1355              1360 agc atc atg ggc  gta aat ttg ttt  gct ggc aaa ttc  tac cac tgt          4394
Ser Ile Met Gly  Val Asn Leu Phe  Ala Gly Lys Phe  Tyr His Cys
        1365              1370              1375 att aac acc aca  act ggt gac agg  ttt gac atc gaa  gac gtg aat          4439
Ile Asn Thr Thr  Thr Gly Asp Arg  Phe Asp Ile Glu  Asp Val Asn
        1380              1385              1390 aat cat act gat  tgc cta aaa cta  ata gaa aga aat  gag act gct          4484
Asn His Thr Asp  Cys Leu Lys Leu  Ile Glu Arg Asn  Glu Thr Ala
        1395              1400              1405 cga tgg aaa aat  gtg aaa gta aac  ttt gat aat gta  gga ttt ggg          4529
Arg Trp Lys Asn  Val Lys Val Asn  Phe Asp Asn Val  Gly Phe Gly
        1410              1415              1420 tat ctc tct ttg  ctt caa gtt gcc  aca ttc aaa gga  tgg atg gat          4574
Tyr Leu Ser Leu  Leu Gln Val Ala  Thr Phe Lys Gly  Trp Met Asp
        1425              1430              1435 ata atg tat gca  gca gtt gat tcc  aga aat gtg gaa  ctc cag cct          4619
Ile Met Tyr Ala  Ala Val Asp Ser  Arg Asn Val Glu  Leu Gln Pro
        1440              1445              1450
```

```
aag tat gaa aaa agt ctg tac atg tat ctt tac ttt gtt att ttc     4664
Lys Tyr Glu Lys Ser Leu Tyr Met Tyr Leu Tyr Phe Val Ile Phe
            1455                1460                1465 atc atc ttt ggg tcc ttc ttc acc ttg aac ctg ttt att ggt gtc     4709
Ile Ile Phe Gly Ser Phe Phe Thr Leu Asn Leu Phe Ile Gly Val
            1470                1475                1480 atc ata gat aat ttc aac cag cag aaa aag aag ttt gga ggt caa     4754
Ile Ile Asp Asn Phe Asn Gln Gln Lys Lys Lys Phe Gly Gly Gln
            1485                1490                1495 gac atc ttt atg aca gaa gaa cag aag aaa tac tat aat gca atg     4799
Asp Ile Phe Met Thr Glu Glu Gln Lys Lys Tyr Tyr Asn Ala Met
            1500                1505                1510 aaa aaa tta gga tcg aaa aaa ccg caa aag cct ata cct cga cca     4844
Lys Lys Leu Gly Ser Lys Lys Pro Gln Lys Pro Ile Pro Arg Pro
            1515                1520                1525 gga aac aaa ttt caa gga atg gtc ttt gac ttc gta acc aga caa     4889
Gly Asn Lys Phe Gln Gly Met Val Phe Asp Phe Val Thr Arg Gln
            1530                1535                1540 gtt ttt gac ata agc atc atg att ctc atc tgt ctt aac atg gtc     4934
Val Phe Asp Ile Ser Ile Met Ile Leu Ile Cys Leu Asn Met Val
            1545                1550                1555 aca atg atg gtg gaa aca gat gac cag agt gaa tat gtg act acc     4979
Thr Met Met Val Glu Thr Asp Asp Gln Ser Glu Tyr Val Thr Thr
            1560                1565                1570 att ttg tca cgc atc aat ctg gtg ttc att gtg cta ttt act gga     5024
Ile Leu Ser Arg Ile Asn Leu Val Phe Ile Val Leu Phe Thr Gly
            1575                1580                1585 gag tgt gta ctg aaa ctc atc tct cta cgc cat tat tat ttt acc     5069
Glu Cys Val Leu Lys Leu Ile Ser Leu Arg His Tyr Tyr Phe Thr
            1590                1595                1600 att gga tgg aat att ttt gat ttt gtg gtt gtc att ctc tcc att     5114
Ile Gly Trp Asn Ile Phe Asp Phe Val Val Val Ile Leu Ser Ile
            1605                1610                1615 gta ggt atg ttt ctt gcc gag ctg ata gaa aag tat ttc gtg tcc     5159
Val Gly Met Phe Leu Ala Glu Leu Ile Glu Lys Tyr Phe Val Ser
            1620                1625                1630 cct acc ctg ttc cga gtg atc cgt ctt gct agg att ggc cga atc     5204
Pro Thr Leu Phe Arg Val Ile Arg Leu Ala Arg Ile Gly Arg Ile
            1635                1640                1645 cta cgt ctg atc aaa gga gca aag ggg atc cgc acg ctg ctc ttt     5249
Leu Arg Leu Ile Lys Gly Ala Lys Gly Ile Arg Thr Leu Leu Phe
            1650                1655                1660 gct ttg atg atg tcc ctt cct gcg ttg ttt aac atc ggc ctc cta     5294
Ala Leu Met Met Ser Leu Pro Ala Leu Phe Asn Ile Gly Leu Leu
            1665                1670                1675 ctc ttc cta gtc atg ttc atc tac gcc atc ttt ggg atg tcc aac     5339
Leu Phe Leu Val Met Phe Ile Tyr Ala Ile Phe Gly Met Ser Asn
            1680                1685                1690 ttt gcc tat gtt aag agg gaa gtt ggg atc gat gac atg ttc aac     5384
Phe Ala Tyr Val Lys Arg Glu Val Gly Ile Asp Asp Met Phe Asn
            1695                1700                1705 ttt gag acc ttt ggc aac agc atg atc tgc cta ttc caa att aca     5429
Phe Glu Thr Phe Gly Asn Ser Met Ile Cys Leu Phe Gln Ile Thr
            1710                1715                1720 acc tct gct ggc tgg gat gga ttg cta gca ccc att ctc aac agt     5474
Thr Ser Ala Gly Trp Asp Gly Leu Leu Ala Pro Ile Leu Asn Ser
            1725                1730                1735 aag cca ccc gac tgt gac cct aat aaa gtt aac cct gga agc tca     5519
Lys Pro Pro Asp Cys Asp Pro Asn Lys Val Asn Pro Gly Ser Ser
            1740                1745                1750
```

-continued

| | | |
|---|---|---|
| gtt aag gga gac tgt ggg aac cca tct gtt gga att ttc ttt ttt<br>Val Lys Gly Asp Cys Gly Asn Pro Ser Val Gly Ile Phe Phe Phe<br>1755              1760              1765 | 5564 |
| gtc agt tac atc atc ata tcc ttc ctg gtt gtg gtg aac atg tac<br>Val Ser Tyr Ile Ile Ile Ser Phe Leu Val Val Val Asn Met Tyr<br>1770              1775              1780 | 5609 |
| atc gcg gtc atc ctg gag aac ttc agt gtt gct act gaa gaa agt<br>Ile Ala Val Ile Leu Glu Asn Phe Ser Val Ala Thr Glu Glu Ser<br>1785              1790              1795 | 5654 |
| gca gag cct ctg agt gag gat gac ttt gag atg ttc tat gag gtt<br>Ala Glu Pro Leu Ser Glu Asp Asp Phe Glu Met Phe Tyr Glu Val<br>1800              1805              1810 | 5699 |
| tgg gag aag ttt gat ccc gat gca act cag ttc atg gaa ttt gaa<br>Trp Glu Lys Phe Asp Pro Asp Ala Thr Gln Phe Met Glu Phe Glu<br>1815              1820              1825 | 5744 |
| aaa tta tct cag ttt gca gct gcg ctt gaa ccg cct ctc aat ctg<br>Lys Leu Ser Gln Phe Ala Ala Ala Leu Glu Pro Pro Leu Asn Leu<br>1830              1835              1840 | 5789 |
| cca caa cca aac aaa ctc cag ctc att gcc atg gat ttg ccc atg<br>Pro Gln Pro Asn Lys Leu Gln Leu Ile Ala Met Asp Leu Pro Met<br>1845              1850              1855 | 5834 |
| gtg agt ggt gac cgg atc cac tgt ctt gat atc tta ttt gct ttt<br>Val Ser Gly Asp Arg Ile His Cys Leu Asp Ile Leu Phe Ala Phe<br>1860              1865              1870 | 5879 |
| aca aag cgg gtt cta gga gag agt gga gag atg gat gct cta cga<br>Thr Lys Arg Val Leu Gly Glu Ser Gly Glu Met Asp Ala Leu Arg<br>1875              1880              1885 | 5924 |
| ata cag atg gaa gag cga ttc atg gct tcc aat cct tcc aag gtc<br>Ile Gln Met Glu Glu Arg Phe Met Ala Ser Asn Pro Ser Lys Val<br>1890              1895              1900 | 5969 |
| tcc tat cag cca atc act act act tta aaa cga aaa caa gag gaa<br>Ser Tyr Gln Pro Ile Thr Thr Thr Leu Lys Arg Lys Gln Glu Glu<br>1905              1910              1915 | 6014 |
| gta tct gct gtc att att cag cgt gct tac aga cgc cac ctt tta<br>Val Ser Ala Val Ile Ile Gln Arg Ala Tyr Arg Arg His Leu Leu<br>1920              1925              1930 | 6059 |
| aag cga act gta aaa caa gct tcc ttt acg tac aat aaa aac aaa<br>Lys Arg Thr Val Lys Gln Ala Ser Phe Thr Tyr Asn Lys Asn Lys<br>1935              1940              1945 | 6104 |
| atc aaa ggt ggg gct aat ctt ctt ata aaa gaa gac atg ata att<br>Ile Lys Gly Gly Ala Asn Leu Leu Ile Lys Glu Asp Met Ile Ile<br>1950              1955              1960 | 6149 |
| gac aga ata aat gaa aac tct att aca gaa aaa act gat ctg acc<br>Asp Arg Ile Asn Glu Asn Ser Ile Thr Glu Lys Thr Asp Leu Thr<br>1965              1970              1975 | 6194 |
| atg tcc act gca gct tgt cca cct tcc tat gac cgg gtg aca aag<br>Met Ser Thr Ala Ala Cys Pro Pro Ser Tyr Asp Arg Val Thr Lys<br>1980              1985              1990 | 6239 |
| cca att gtg gaa aaa cat gag caa gaa ggc aaa gat gaa aaa gcc<br>Pro Ile Val Glu Lys His Glu Gln Glu Gly Lys Asp Glu Lys Ala<br>1995              2000              2005 | 6284 |
| aaa ggg aaa taa atgaaataa ataaaataa ttgggtgaca aattgtttac<br>Lys Gly Lys | 6336 |
| agcctgtgaa ggtgatgtat ttttatcaac aggactcctt taggaggtca atgccaaact | 6396 |
| gactgttttt acacaaatct ccttaaggtc agtgcctaca ataagacagt gacccctttgt | 6456 |
| cagcaaactg tgactctgtg taaaggggag atgaccttga caggaggtta ctgttctcac | 6516 |
| taccagctga cactgctgaa gataagatgc acaatggcta gtcagactgt agggaccagt | 6576 |

```
ttcaagggt gcaaacctgt gattttgggg ttgtttaaca tgaaacactt tagtgtagta    6636
attgtatcca ctgtttgcat ttcaactgcc acatttgtca cattttatg gaatctgtta     6696
gtggattcat cttttgtta atccatgtgt ttattatatg tgactatttt tgtaaacgaa     6756
gtttctgttg agaaataggc taaggacctc tataacaggt atgccacctg ggggtatgg     6816
caaccacatg gccctcccag ctacacaaag tcgtggtttg catgagggca tgctgcactt     6876
agagatcatg catgagaaaa agtcacaaga aaaacaaatt cttaaatttc accatatttc     6936
tgggaggggt aattgggtga taagtggagg tgctttgttg atcttgtttt gcgaaatcca     6996
gccccctagac caagtagatt atttgtgggt aggccagtaa atcttagcag gtgcaaactt   7056
cattcaaatg tttggagtca taaatgttat gtttctttt gttgtattaa aaaaaaaacc    7116
tgaatagtga atattgcccc tcaccctcca ccgccagaag actgaattga ccaaaattac     7176
tctttataaa tttctgcttt ttcctgcact tgtttagcc atctttgggc tctcagcaag      7236
gttgacactg tatatgttaa tgaaatgcta tttattatgt aaatagtcat tttaccctgt    7296
ggtgcacgtt tgagcaaaca aataatgacc taagcacagt atttattgca tcaaatatgt    7356
accacaagaa atgtagagtg caagctttac acaggtaata aaatgtattc tgtaccattt    7416
atagatagtt tggatgctat caatgcatgt ttatattacc atgctgctgt atctggtttc    7476
tctcactgct cagaatctca tttatgagaa accatatgtc agtggtaaag tcaaggaaat    7536
tgttcaacag atctcattta tttaagtcat taagcaatag tttgcagcac tttaacagct    7596
ttttggttat tttacatttt taagtggata acatatggta tatagccaga ctgtacagac    7656
atgtttaaaa aaacacactg cttaacctat taaatatgtg tttagaattt tataagcaaa    7716
tataaatact gtaaaaagtc actttatttt attttttcagc attatgtaca taaatatgaa   7776
gaggaaatta tcttcaggtt gatatcacaa tcactttct tactttctgt ccatagtact    7836
ttttcatgaa agaaatttgc taaataagac atgaaaacaa gactgggtag ttgtagattt    7896
ctgctttta aattacattt gctaatttta gattatttca caattttaag gagcaaaata    7956
ggttcacgat tcatatccaa attatgcttt gcaattggaa aagggtttaa aattttattt   8016
atatttctgg tagtacctgt actaactgaa ttgaaggtag tgcttatgtt attttgttc    8076
ttttttctg acttcggttt atgttttcat ttctttggag taatgctgct ctagattgtt    8136
ctaaatagaa tgtgggcttc ataatttttt tttccacaaa aacagagtag tcaacttata    8196
tagtcaatta catcaggaca ttttgtgttt cttacagaag caaaccatag gctcctcttt    8256
tccttaaaac tacttagata aactgtattc gtgaactgca tgctggaaaa tgctactatt    8316
atgctaaata atgctaacca acatttaaaa tgtgcaaaac taataaagat tacatttttt    8376
atttt                                                                 8381
```

<210> SEQ ID NO 4
<211> LENGTH: 2009
<212> TYPE: PRT
<213> ORGANISM: Homo sapiens

<400> SEQUENCE: 4

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
 50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Leu Asn Lys Leu
                 85                  90                  95

Lys Ala Ile Phe Arg Phe Ser Ala Thr Ser Ala Leu Tyr Ile Leu Thr
             100                 105                 110

Pro Phe Asn Pro Leu Arg Lys Ile Ala Ile Lys Ile Leu Val His Ser
         115                 120                 125

Leu Phe Ser Met Leu Ile Met Cys Thr Ile Leu Thr Asn Cys Val Phe
 130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
450                 455                 460

```
Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880
```

-continued

```
Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
                995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275
```

-continued

```
Tyr Phe Thr Asn Ala Trp Cys Trp Leu Asp Phe Leu Ile Val Asp
    1280            1285            1290

Val Ser Leu Val Ser Leu Thr Ala Asn Ala Leu Gly Tyr Ser Glu
    1295            1300            1305

Leu Gly Ala Ile Lys Ser Leu Arg Thr Leu Arg Ala Leu Arg Pro
    1310            1315            1320

Leu Arg Ala Leu Ser Arg Phe Glu Gly Met Arg Val Val Val Asn
    1325            1330            1335

Ala Leu Leu Gly Ala Ile Pro Ser Ile Met Asn Val Leu Leu Leu
    1340            1345            1350

Cys Leu Ile Phe Trp Leu Ile Phe Ser Ile Met Gly Val Asn Leu
    1355            1360            1365

Phe Ala Gly Lys Phe Tyr His Cys Ile Asn Thr Thr Thr Gly Asp
    1370            1375            1380

Arg Phe Asp Ile Glu Asp Val Asn Asn His Thr Asp Cys Leu Lys
    1385            1390            1395

Leu Ile Glu Arg Asn Glu Thr Ala Arg Trp Lys Asn Val Lys Val
    1400            1405            1410

Asn Phe Asp Asn Val Gly Phe Gly Tyr Leu Ser Leu Leu Gln Val
    1415            1420            1425

Ala Thr Phe Lys Gly Trp Met Asp Ile Met Tyr Ala Ala Val Asp
    1430            1435            1440

Ser Arg Asn Val Glu Leu Gln Pro Lys Tyr Glu Lys Ser Leu Tyr
    1445            1450            1455

Met Tyr Leu Tyr Phe Val Ile Phe Ile Ile Phe Gly Ser Phe Phe
    1460            1465            1470

Thr Leu Asn Leu Phe Ile Gly Val Ile Ile Asp Asn Phe Asn Gln
    1475            1480            1485

Gln Lys Lys Lys Phe Gly Gly Gln Asp Ile Phe Met Thr Glu Glu
    1490            1495            1500

Gln Lys Lys Tyr Tyr Asn Ala Met Lys Lys Leu Gly Ser Lys Lys
    1505            1510            1515

Pro Gln Lys Pro Ile Pro Arg Pro Gly Asn Lys Phe Gln Gly Met
    1520            1525            1530

Val Phe Asp Phe Val Thr Arg Gln Val Phe Asp Ile Ser Ile Met
    1535            1540            1545

Ile Leu Ile Cys Leu Asn Met Val Thr Met Met Val Glu Thr Asp
    1550            1555            1560

Asp Gln Ser Glu Tyr Val Thr Thr Ile Leu Ser Arg Ile Asn Leu
    1565            1570            1575

Val Phe Ile Val Leu Phe Thr Gly Glu Cys Val Leu Lys Leu Ile
    1580            1585            1590

Ser Leu Arg His Tyr Tyr Phe Thr Ile Gly Trp Asn Ile Phe Asp
    1595            1600            1605

Phe Val Val Val Ile Leu Ser Ile Val Gly Met Phe Leu Ala Glu
    1610            1615            1620

Leu Ile Glu Lys Tyr Phe Val Ser Pro Thr Leu Phe Arg Val Ile
    1625            1630            1635

Arg Leu Ala Arg Ile Gly Arg Ile Leu Arg Leu Ile Lys Gly Ala
    1640            1645            1650

Lys Gly Ile Arg Thr Leu Leu Phe Ala Leu Met Met Ser Leu Pro
    1655            1660            1665
```

```
Ala Leu Phe Asn Ile Gly Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005

<210> SEQ ID NO 5
<211> LENGTH: 8381
<212> TYPE: DNA
<213> ORGANISM: Homo sapiens
<220> FEATURE:
<221> NAME/KEY: CDS
<222> LOCATION: (267)..(6296)
```

<400> SEQUENCE: 5

```
atactgcaga ggtctctggt gcatgtgtgt atgtgtgcgt ttgtgtgtgt ttgtgtgtct        60
gtgtgttctg ccccagtgag actgcagccc ttgtaaatac tttgacacct tttgcaagaa       120
ggaatctgaa caattgcaac tgaaggcaca ttgttatcat ctcgtctttg ggtgatgctg       180
ttcctcactg cagatggata attttccttt taatcaggaa tttcatatgc agaataaatg       240
gtaattaaaa tgtgcaggat gacaag atg gag caa aca gtg ctt gta cca cca       293
                              Met Glu Gln Thr Val Leu Val Pro Pro
                                1               5 gga cct gac agc ttc aac ttc ttc acc aga gaa tct ctt gcg gct att        341
Gly Pro Asp Ser Phe Asn Phe Phe Thr Arg Glu Ser Leu Ala Ala Ile
 10              15                  20                  25 gaa aga cgc att gca gaa gaa aag gca aag aat ccc aaa cca gac aaa        389
Glu Arg Arg Ile Ala Glu Glu Lys Ala Lys Asn Pro Lys Pro Asp Lys
             30                  35                  40 aaa gat gac gac gaa aat ggc cca aag cca aat agt gac ttg gaa gct        437
Lys Asp Asp Asp Glu Asn Gly Pro Lys Pro Asn Ser Asp Leu Glu Ala
 45                  50                  55 gga aag aac ctt cca ttt att tat gga gac att cct cca gag atg gtg        485
Gly Lys Asn Leu Pro Phe Ile Tyr Gly Asp Ile Pro Pro Glu Met Val
             60                  65                  70 tca gag ccc ctg gag gac ctg gac ccc tac tat atc aat aag aaa act        533
Ser Glu Pro Leu Glu Asp Leu Asp Pro Tyr Tyr Ile Asn Lys Lys Thr
 75                  80                  85 ttt ata gta ttg aat aaa ttg aag gcc atc ttc cgg ttc agt gcc acc        581
Phe Ile Val Leu Asn Lys Leu Lys Ala Ile Phe Arg Phe Ser Ala Thr
 90                  95                 100                 105 tct gcc ctg tac att tta act ccc ttc aat cct ctt agg aaa ata gct        629
Ser Ala Leu Tyr Ile Leu Thr Pro Phe Asn Pro Leu Arg Lys Ile Ala
             110                 115                 120 att aag att ttg gta cat tca tta ttc agc atg cta att atg tgc act        677
Ile Lys Ile Leu Val His Ser Leu Phe Ser Met Leu Ile Met Cys Thr
             125                 130                 135 att ttg aca aac tgt gtg ttt atg aca atg agt aac cct cct gat tgg        725
Ile Leu Thr Asn Cys Val Phe Met Thr Met Ser Asn Pro Pro Asp Trp
             140                 145                 150 aca aag aat gta gaa tac acc ttc aca gga ata tat act ttt gaa tca        773
Thr Lys Asn Val Glu Tyr Thr Phe Thr Gly Ile Tyr Thr Phe Glu Ser
 155                 160                 165 ctt ata aaa att att gca agg gga ttc tgt tta gaa gat ttt act ttc        821
Leu Ile Lys Ile Ile Ala Arg Gly Phe Cys Leu Glu Asp Phe Thr Phe
 170                 175                 180                 185 ctt cgg gat cca tgg aac tgg ctc gat ttc act gtc att aca ttt gcg        869
Leu Arg Asp Pro Trp Asn Trp Leu Asp Phe Thr Val Ile Thr Phe Ala
             190                 195                 200 tac gtc aca gag ttt gtg gac ctg ggc aat gtc tcg gca ttg aga aca        917
Tyr Val Thr Glu Phe Val Asp Leu Gly Asn Val Ser Ala Leu Arg Thr
             205                 210                 215 ttc aga gtt ctc cga gca ttg aag acg att tca gtc att cca ggc ctg        965
Phe Arg Val Leu Arg Ala Leu Lys Thr Ile Ser Val Ile Pro Gly Leu
             220                 225                 230 aaa acc att gtg gga gcc ctg atc cag tct gtg aag aag ctc tca gat       1013
Lys Thr Ile Val Gly Ala Leu Ile Gln Ser Val Lys Lys Leu Ser Asp
 235                 240                 245 gta atg atc ctg act gtg ttc tgt ctg agc gta ttt gct cta att ggg       1061
Val Met Ile Leu Thr Val Phe Cys Leu Ser Val Phe Ala Leu Ile Gly
 250                 255                 260                 265
```

```
                                                              -continued
ctg cag ctg ttc atg ggc aac ctg agg aat aaa tgt ata caa tgg cct          1109
Leu Gln Leu Phe Met Gly Asn Leu Arg Asn Lys Cys Ile Gln Trp Pro
            270                 275                 280 ccc acc aat gct tcc ttg gag gaa cat agt ata gaa aag aat ata act          1157
Pro Thr Asn Ala Ser Leu Glu Glu His Ser Ile Glu Lys Asn Ile Thr
        285                 290                 295 gtg aat tat aat ggt aca ctt ata aat gaa act gtc ttt gag ttt gac          1205
Val Asn Tyr Asn Gly Thr Leu Ile Asn Glu Thr Val Phe Glu Phe Asp
300                 305                 310 tgg aag tca tat att caa gat tca aga tat cat tat ttc ctg gag ggt          1253
Trp Lys Ser Tyr Ile Gln Asp Ser Arg Tyr His Tyr Phe Leu Glu Gly
    315                 320                 325 ttt tta gat gca cta cta tgt gga aat agc tct gat gca ggc caa tgt          1301
Phe Leu Asp Ala Leu Leu Cys Gly Asn Ser Ser Asp Ala Gly Gln Cys
330                 335                 340                 345 cca gag gga tat atg tgt gtg aaa gct ggt aga aat ccc aat tat ggc          1349
Pro Glu Gly Tyr Met Cys Val Lys Ala Gly Arg Asn Pro Asn Tyr Gly
                350                 355                 360 tac aca agc ttt gat acc ttc agt tgg gct ttt ttg tcc ttg ttt cga          1397
Tyr Thr Ser Phe Asp Thr Phe Ser Trp Ala Phe Leu Ser Leu Phe Arg
            365                 370                 375 cta atg act cag gac ttc tgg gaa aat ctt tat caa ctg aca tta cgt          1445
Leu Met Thr Gln Asp Phe Trp Glu Asn Leu Tyr Gln Leu Thr Leu Arg
        380                 385                 390 gct gct ggg aaa acg tac atg ata ttt ttt gta ttg gtc att ttc ttg          1493
Ala Ala Gly Lys Thr Tyr Met Ile Phe Phe Val Leu Val Ile Phe Leu
    395                 400                 405 ggc tca ttc tac cta ata aat ttg atc ctg gct gtg gtg gcc atg gcc          1541
Gly Ser Phe Tyr Leu Ile Asn Leu Ile Leu Ala Val Val Ala Met Ala
410                 415                 420                 425 tac gag gaa cag aat cag gcc acc ttg gaa gaa gca gaa cag aaa gag          1589
Tyr Glu Glu Gln Asn Gln Ala Thr Leu Glu Glu Ala Glu Gln Lys Glu
                430                 435                 440 gcc gaa ttt cag cag atg att gaa cag ctt aaa aag caa cag gag gca          1637
Ala Glu Phe Gln Gln Met Ile Glu Gln Leu Lys Lys Gln Gln Glu Ala
            445                 450                 455 gct cag cag gca gca acg gca act gcc tca gaa cat tcc aga gag ccc          1685
Ala Gln Gln Ala Ala Thr Ala Thr Ala Ser Glu His Ser Arg Glu Pro
        460                 465                 470 agt gca gca ggc agg ctc tca gac agc tca tct gaa gcc tct aag ttg          1733
Ser Ala Ala Gly Arg Leu Ser Asp Ser Ser Ser Glu Ala Ser Lys Leu
    475                 480                 485 agt tcc aag agt gct aag gaa aga aga aat cgg agg aag aaa aga aaa          1781
Ser Ser Lys Ser Ala Lys Glu Arg Arg Asn Arg Arg Lys Lys Arg Lys
490                 495                 500                 505 cag aaa gag cag tct ggt ggg gaa gag aaa gat gag gat gaa ttc caa          1829
Gln Lys Glu Gln Ser Gly Gly Glu Glu Lys Asp Glu Asp Glu Phe Gln
                510                 515                 520 aaa tct gaa tct gag gac agc atc agg agg aaa ggt ttt cgc ttc tcc          1877
Lys Ser Glu Ser Glu Asp Ser Ile Arg Arg Lys Gly Phe Arg Phe Ser
            525                 530                 535 att gaa ggg aac cga ttg aca tat gaa aag agg tac tcc tcc cca cac          1925
Ile Glu Gly Asn Arg Leu Thr Tyr Glu Lys Arg Tyr Ser Ser Pro His
        540                 545                 550 cag tct ttg ttg agc atc cgt ggc tcc cta ttt tca cca agg cga aat          1973
Gln Ser Leu Leu Ser Ile Arg Gly Ser Leu Phe Ser Pro Arg Arg Asn
    555                 560                 565 agc aga aca agc ctt ttc agc ttt aga ggg cga gca aag gat gtg gga          2021
Ser Arg Thr Ser Leu Phe Ser Phe Arg Gly Arg Ala Lys Asp Val Gly
570                 575                 580                 585
```

-continued

| | |
|---|---|
| tct gag aac gac ttc gca gat gat gag cac agc acc ttt gag gat aac<br>Ser Glu Asn Asp Phe Ala Asp Asp Glu His Ser Thr Phe Glu Asp Asn<br>590                595                600 | 2069 |
| gag agc cgt aga gat tcc ttg ttt gtg ccc cga cga cac gga gag aga<br>Glu Ser Arg Arg Asp Ser Leu Phe Val Pro Arg Arg His Gly Glu Arg<br>605                610                615 | 2117 |
| cgc aac agc aac ctg agt cag acc agt agg tca tcc cgg atg ctg gca<br>Arg Asn Ser Asn Leu Ser Gln Thr Ser Arg Ser Ser Arg Met Leu Ala<br>620                625                630 | 2165 |
| gtg ttt cca gcg aat ggg aag atg cac agc act gtg gat tgc aat ggt<br>Val Phe Pro Ala Asn Gly Lys Met His Ser Thr Val Asp Cys Asn Gly<br>635                640                645 | 2213 |
| gtg gtt tcc ttg gtt ggt gga cct tca gtt cct aca tcg cct gtt gga<br>Val Val Ser Leu Val Gly Gly Pro Ser Val Pro Thr Ser Pro Val Gly<br>650              655                660                665 | 2261 |
| cag ctt ctg cca gag gtg ata ata gat aag cca gct act gat gac aat<br>Gln Leu Leu Pro Glu Val Ile Ile Asp Lys Pro Ala Thr Asp Asp Asn<br>670                675                680 | 2309 |
| gga aca acc act gaa act gaa atg aga aag aga agg tca agt tct ttc<br>Gly Thr Thr Thr Glu Thr Glu Met Arg Lys Arg Arg Ser Ser Ser Phe<br>685                690                695 | 2357 |
| cac gtt tcc atg gac ttt cta gaa gat cct tcc caa agg caa cga gca<br>His Val Ser Met Asp Phe Leu Glu Asp Pro Ser Gln Arg Gln Arg Ala<br>700                705                710 | 2405 |
| atg agt ata gcc agc att cta aca aat aca gta gaa gaa ctt gaa gaa<br>Met Ser Ile Ala Ser Ile Leu Thr Asn Thr Val Glu Glu Leu Glu Glu<br>715                720                725 | 2453 |
| tcc agg cag aaa tgc cca ccc tgt tgg tat aaa ttt tcc aac ata ttc<br>Ser Arg Gln Lys Cys Pro Pro Cys Trp Tyr Lys Phe Ser Asn Ile Phe<br>730                735                740                745 | 2501 |
| tta atc tgg gac tgt tct cca tat tgg tta aaa gtg aaa cat gtt gtc<br>Leu Ile Trp Asp Cys Ser Pro Tyr Trp Leu Lys Val Lys His Val Val<br>750                755                760 | 2549 |
| aac ctg gtt gtg atg gac cca ttt gtt gac ctg gcc atc acc atc tgt<br>Asn Leu Val Val Met Asp Pro Phe Val Asp Leu Ala Ile Thr Ile Cys<br>765                770                775 | 2597 |
| att gtc tta aat act ctt ttc atg gcc atg gag cac tat cca atg acg<br>Ile Val Leu Asn Thr Leu Phe Met Ala Met Glu His Tyr Pro Met Thr<br>780                785                790 | 2645 |
| gac cat ttc aat aat gtg ctt aca gta gga aac ttg gtt ttc act ggg<br>Asp His Phe Asn Asn Val Leu Thr Val Gly Asn Leu Val Phe Thr Gly<br>795                800                805 | 2693 |
| atc ttt aca gca gaa atg ttt ctg aaa att att gcc atg gat cct tac<br>Ile Phe Thr Ala Glu Met Phe Leu Lys Ile Ile Ala Met Asp Pro Tyr<br>810                815                820                825 | 2741 |
| tat tat ttc caa gaa ggc tgg aat atc ttt gac ggt ttt att gtg acg<br>Tyr Tyr Phe Gln Glu Gly Trp Asn Ile Phe Asp Gly Phe Ile Val Thr<br>830                835                840 | 2789 |
| ctt agc ctg gta gaa ctt gga ctc gcc aat gtg gaa gga tta tct gtt<br>Leu Ser Leu Val Glu Leu Gly Leu Ala Asn Val Glu Gly Leu Ser Val<br>845                850                855 | 2837 |
| ctc cgt tca ttt cga ttg ctg cga gtt ttc aag ttg gca aaa tct tgg<br>Leu Arg Ser Phe Arg Leu Leu Arg Val Phe Lys Leu Ala Lys Ser Trp<br>860                865                870 | 2885 |
| cca acg tta aat atg cta ata aag atc atc ggc aat tcc gtg ggg gct<br>Pro Thr Leu Asn Met Leu Ile Lys Ile Ile Gly Asn Ser Val Gly Ala<br>875                880                885 | 2933 |
| ctg gga aat tta acc ctc gtc ttg gcc atc atc gtc ttc att ttt gcc<br>Leu Gly Asn Leu Thr Leu Val Leu Ala Ile Ile Val Phe Ile Phe Ala<br>890                895                900                905 | 2981 |

```
gtg gtc ggc atg cag ctc ttt ggt aaa agc tac aaa gat tgt gtc tgc    3029
Val Val Gly Met Gln Leu Phe Gly Lys Ser Tyr Lys Asp Cys Val Cys
            910             915             920 aag atc gcc agt gat tgt caa ctc cca cgc tgg cac atg aat gac ttc    3077
Lys Ile Ala Ser Asp Cys Gln Leu Pro Arg Trp His Met Asn Asp Phe
        925             930             935 ttc cac tcc ttc ctg att gtg ttc cgc gtg ctg tgt ggg gag tgg ata    3125
Phe His Ser Phe Leu Ile Val Phe Arg Val Leu Cys Gly Glu Trp Ile
        940             945             950 gag acc atg tgg gac tgt atg gag gtt gct ggt caa gcc atg tgc ctt    3173
Glu Thr Met Trp Asp Cys Met Glu Val Ala Gly Gln Ala Met Cys Leu
        955             960             965 act gtc ttc atg atg gtc atg gtg att gga aac cta gtg gtc ctg aat    3221
Thr Val Phe Met Met Val Met Val Ile Gly Asn Leu Val Val Leu Asn
970             975             980             985 ctc ttt ctg gcc ttg ctt ctg agc tca ttt agt gca gac aac ctt  gca   3269
Leu Phe Leu Ala Leu Leu Leu Ser Ser Phe Ser Ala Asp Asn Leu  Ala
            990             995            1000 gcc act gat gat gat aat gaa atg aat  aat ctc caa att gct  gtg     3314
Ala Thr Asp Asp Asp Asn Glu Met Asn  Asn Leu Gln Ile Ala  Val
           1005            1010            1015 gat agg atg cac aaa gga gta gct tat  gtg aaa aga aaa ata  tat     3359
Asp Arg Met His Lys Gly Val Ala Tyr  Val Lys Arg Lys Ile  Tyr
           1020            1025            1030 gaa ttt att caa cag tcc ttc att agg  aaa caa aag att tta  gat     3404
Glu Phe Ile Gln Gln Ser Phe Ile Arg  Lys Gln Lys Ile Leu  Asp
           1035            1040            1045 gaa att aaa cca ctt gat gat cta aac  aac aag aaa gac agt  tgt     3449
Glu Ile Lys Pro Leu Asp Asp Leu Asn  Asn Lys Lys Asp Ser  Cys
           1050            1055            1060 atg tcc aat cat aca aca gaa att ggg  aaa gat ctt gac tat  ctt     3494
Met Ser Asn His Thr Thr Glu Ile Gly  Lys Asp Leu Asp Tyr  Leu
           1065            1070            1075 aaa gat gta aat gga act aca agt ggt  ata gga act ggc agc  agt     3539
Lys Asp Val Asn Gly Thr Thr Ser Gly  Ile Gly Thr Gly Ser  Ser
           1080            1085            1090 gtt gaa aaa tac att att gat gaa agt  gat tac atg tca ttc  ata     3584
Val Glu Lys Tyr Ile Ile Asp Glu Ser  Asp Tyr Met Ser Phe  Ile
           1095            1100            1105 aac aac ccc agt ctt act gtg act gta  cca att gct gta gga  gaa     3629
Asn Asn Pro Ser Leu Thr Val Thr Val  Pro Ile Ala Val Gly  Glu
           1110            1115            1120 tct gac ttt gaa aat tta aac acg gaa  gac ttt agt agt gaa  tcg     3674
Ser Asp Phe Glu Asn Leu Asn Thr Glu  Asp Phe Ser Ser Glu  Ser
           1125            1130            1135 gat ctg gaa gaa agc aaa gag aaa ctg  aat gaa agc agt agc  tca     3719
Asp Leu Glu Glu Ser Lys Glu Lys Leu  Asn Glu Ser Ser Ser  Ser
           1140            1145            1150 tca gaa ggt agc act gtg gac atc ggc  gca cct gta gaa gaa  cag     3764
Ser Glu Gly Ser Thr Val Asp Ile Gly  Ala Pro Val Glu Glu  Gln
           1155            1160            1165 ccc gta gtg gaa cct gaa gaa act ctt  gaa cca gaa gct tgt  ttc     3809
Pro Val Val Glu Pro Glu Glu Thr Leu  Glu Pro Glu Ala Cys  Phe
           1170            1175            1180 act gaa ggc tgt gta caa aga ttc aag  tgt tgt caa atc aat  gtg     3854
Thr Glu Gly Cys Val Gln Arg Phe Lys  Cys Cys Gln Ile Asn  Val
           1185            1190            1195 gaa gaa ggc aga gga aaa caa tgg tgg  aac ctg aga agg acg  tgt     3899
Glu Glu Gly Arg Gly Lys Gln Trp Trp  Asn Leu Arg Arg Thr  Cys
           1200            1205            1210
```

```
ttc cga ata gtt gaa cat aac tgg ttt gag acc ttc att gtt ttc      3944
Phe Arg Ile Val Glu His Asn Trp Phe Glu Thr Phe Ile Val Phe
        1215                1220                1225 atg att ctc ctt agt agt ggt gct ctg gca ttt gaa gat ata tat      3989
Met Ile Leu Leu Ser Ser Gly Ala Leu Ala Phe Glu Asp Ile Tyr
        1230                1235                1240 att gat cag cga aag acg att aag acg atg ttg gaa tat gct gac      4034
Ile Asp Gln Arg Lys Thr Ile Lys Thr Met Leu Glu Tyr Ala Asp
        1245                1250                1255 aag gtt ttc act tac att ttc att ctg gaa atg ctt cta aaa tgg      4079
Lys Val Phe Thr Tyr Ile Phe Ile Leu Glu Met Leu Leu Lys Trp
        1260                1265                1270 gtg gca tat ggc tat caa aca tat ttc acc aat gcc tgg tgt tgg      4124
Val Ala Tyr Gly Tyr Gln Thr Tyr Phe Thr Asn Ala Trp Cys Trp
        1275                1280                1285 ctg gac ttc tta att gtt gat gtt tca ttg gtc agt tta aca gca      4169
Leu Asp Phe Leu Ile Val Asp Val Ser Leu Val Ser Leu Thr Ala
        1290                1295                1300 aat gcc ttg ggt tac tca gaa ctt gga gcc atc aaa tct ctc agg      4214
Asn Ala Leu Gly Tyr Ser Glu Leu Gly Ala Ile Lys Ser Leu Arg
        1305                1310                1315 aca cta aga gct ctg aga cct cta aga gcc tta tct cga ttt gaa      4259
Thr Leu Arg Ala Leu Arg Pro Leu Arg Ala Leu Ser Arg Phe Glu
        1320                1325                1330 ggg atg agg gtg gtt gtg aat gcc ctt tta gga gca att cca tcc      4304
Gly Met Arg Val Val Val Asn Ala Leu Leu Gly Ala Ile Pro Ser
        1335                1340                1345 atc atg aat gtg ctt ctg gtt tgt ctt ata ttc tgg cta att ttc      4349
Ile Met Asn Val Leu Leu Val Cys Leu Ile Phe Trp Leu Ile Phe
        1350                1355                1360 agc atc atg ggc gta aat ttg ttt gct ggc aaa ttc tac cac tgt      4394
Ser Ile Met Gly Val Asn Leu Phe Ala Gly Lys Phe Tyr His Cys
        1365                1370                1375 att aac acc aca act ggt gac agg ttt gac atc gaa gac gtg aat      4439
Ile Asn Thr Thr Thr Gly Asp Arg Phe Asp Ile Glu Asp Val Asn
        1380                1385                1390 aat cat act gat tgc cta aaa cta ata gaa aga aat gag act gct      4484
Asn His Thr Asp Cys Leu Lys Leu Ile Glu Arg Asn Glu Thr Ala
        1395                1400                1405 cga tgg aaa aat gtg aaa gta aac ttt gat aat gta gga ttt ggg      4529
Arg Trp Lys Asn Val Lys Val Asn Phe Asp Asn Val Gly Phe Gly
        1410                1415                1420 tat ctc tct ttg ctt caa gtt gcc aca ttc aaa gga tgg atg gat      4574
Tyr Leu Ser Leu Leu Gln Val Ala Thr Phe Lys Gly Trp Met Asp
        1425                1430                1435 ata atg tat gca gca gtt gat tcc aga aat gtg gaa ctc cag cct      4619
Ile Met Tyr Ala Ala Val Asp Ser Arg Asn Val Glu Leu Gln Pro
        1440                1445                1450 aag tat gaa aaa agt ctg tac atg tat ctt tac ttt gtt att ttc      4664
Lys Tyr Glu Lys Ser Leu Tyr Met Tyr Leu Tyr Phe Val Ile Phe
        1455                1460                1465 atc atc ttt ggg tcc ttc ttc acc ttg aac ctg ttt att ggt gtc      4709
Ile Ile Phe Gly Ser Phe Phe Thr Leu Asn Leu Phe Ile Gly Val
        1470                1475                1480 atc ata gat aat ttc aac cag cag aaa aag aag ttt gga ggt caa      4754
Ile Ile Asp Asn Phe Asn Gln Gln Lys Lys Lys Phe Gly Gly Gln
        1485                1490                1495 gac atc ttt atg aca gaa gaa cag aag aaa tac tat aat gca atg      4799
Asp Ile Phe Met Thr Glu Glu Gln Lys Lys Tyr Tyr Asn Ala Met
        1500                1505                1510
```

```
aaa aaa tta gga tcg aaa aaa ccg caa aag cct ata cct cga cca       4844
Lys Lys Leu Gly Ser Lys Lys Pro Gln Lys Pro Ile Pro Arg Pro
        1515                1520                1525 gga aac aaa ttt caa gga atg gtc ttt gac ttc gta acc aga caa       4889
Gly Asn Lys Phe Gln Gly Met Val Phe Asp Phe Val Thr Arg Gln
        1530                1535                1540 gtt ttt gac ata agc atc atg att ctc atc tgt ctt aac atg gtc       4934
Val Phe Asp Ile Ser Ile Met Ile Leu Ile Cys Leu Asn Met Val
        1545                1550                1555 aca atg atg gtg gaa aca gat gac cag agt gaa tat gtg act acc       4979
Thr Met Met Val Glu Thr Asp Asp Gln Ser Glu Tyr Val Thr Thr
        1560                1565                1570 att ttg tca cgc atc aat ctg gtg ttc att gtg cta ttt act gga       5024
Ile Leu Ser Arg Ile Asn Leu Val Phe Ile Val Leu Phe Thr Gly
        1575                1580                1585 gag tgt gta ctg aaa ctc atc tct cta cgc cat tat tat ttt acc       5069
Glu Cys Val Leu Lys Leu Ile Ser Leu Arg His Tyr Tyr Phe Thr
        1590                1595                1600 att gga tgg aat att ttt gat ttt gtg gtt gtc att ctc tcc att       5114
Ile Gly Trp Asn Ile Phe Asp Phe Val Val Val Ile Leu Ser Ile
        1605                1610                1615 gta ggt atg ttt ctt gcc gag ctg ata gaa aag tat ttc gtg tcc       5159
Val Gly Met Phe Leu Ala Glu Leu Ile Glu Lys Tyr Phe Val Ser
        1620                1625                1630 cct acc ctg ttc cga gtg atc cgt ctt gct agg att ggc cga atc       5204
Pro Thr Leu Phe Arg Val Ile Arg Leu Ala Arg Ile Gly Arg Ile
        1635                1640                1645 cta cgt ctg atc aaa gga gca aag ggg atg cgc acg ctg ctc ttt       5249
Leu Arg Leu Ile Lys Gly Ala Lys Gly Met Arg Thr Leu Leu Phe
        1650                1655                1660 gct ttg atg atg tcc ctt cct gcg ttg ttt aac atc ggc ctc cta       5294
Ala Leu Met Met Ser Leu Pro Ala Leu Phe Asn Ile Gly Leu Leu
        1665                1670                1675 ctc ttc cta gtc atg ttc atc tac gcc atc ttt ggg atg tcc aac       5339
Leu Phe Leu Val Met Phe Ile Tyr Ala Ile Phe Gly Met Ser Asn
        1680                1685                1690 ttt gcc tat gtt aag agg gaa gtt ggg atc gat gac atg ttc aac       5384
Phe Ala Tyr Val Lys Arg Glu Val Gly Ile Asp Asp Met Phe Asn
        1695                1700                1705 ttt gag acc ttt ggc aac agc atg atc tgc cta ttc caa att aca       5429
Phe Glu Thr Phe Gly Asn Ser Met Ile Cys Leu Phe Gln Ile Thr
        1710                1715                1720 acc tct gct ggc tgg gat gga ttg cta gca ccc att ctc aac agt       5474
Thr Ser Ala Gly Trp Asp Gly Leu Leu Ala Pro Ile Leu Asn Ser
        1725                1730                1735 aag cca ccc gac tgt gac cct aat aaa gtt aac cct gga agc tca       5519
Lys Pro Pro Asp Cys Asp Pro Asn Lys Val Asn Pro Gly Ser Ser
        1740                1745                1750 gtt aag gga gac tgt ggg aac cca tct gtt gga att ttc ttt ttt       5564
Val Lys Gly Asp Cys Gly Asn Pro Ser Val Gly Ile Phe Phe Phe
        1755                1760                1765 gtc agt tac atc atc ata tcc ttc ctg gtt gtg gtg aac atg tac       5609
Val Ser Tyr Ile Ile Ile Ser Phe Leu Val Val Val Asn Met Tyr
        1770                1775                1780 atc gcg gtc atc ctg gag aac ttc agt gtt gct act gaa gaa agt       5654
Ile Ala Val Ile Leu Glu Asn Phe Ser Val Ala Thr Glu Glu Ser
        1785                1790                1795 gca gag cct ctg agt gag gat gac ttt gag atg ttc tat gag gtt       5699
Ala Glu Pro Leu Ser Glu Asp Asp Phe Glu Met Phe Tyr Glu Val
        1800                1805                1810
```

| | | | | | | | | | | | | | |
|---|---|---|---|---|---|---|---|---|---|---|---|---|---|
| tgg | gag | aag | ttt | gat | ccc | gat | gca | act | cag | ttc | atg | gaa | ttt | gaa | 5744 |
| Trp | Glu | Lys | Phe | Asp | Pro | Asp | Ala | Thr | Gln | Phe | Met | Glu | Phe | Glu |
| | | 1815 | | | | 1820 | | | | 1825 | | | | |

| aaa | tta | tct | cag | ttt | gca | gct | gcg | ctt | gaa | ccg | cct | ctc | aat | ctg | 5789 |
| Lys | Leu | Ser | Gln | Phe | Ala | Ala | Ala | Leu | Glu | Pro | Pro | Leu | Asn | Leu |
| | 1830 | | | | 1835 | | | | 1840 | | | | | |

| cca | caa | cca | aac | aaa | ctc | cag | ctc | att | gcc | atg | gat | ttg | ccc | atg | 5834 |
| Pro | Gln | Pro | Asn | Lys | Leu | Gln | Leu | Ile | Ala | Met | Asp | Leu | Pro | Met |
| 1845 | | | | | 1850 | | | | 1855 | | | | | |

| gtg | agt | ggt | gac | cgg | atc | cac | tgt | ctt | gat | atc | tta | ttt | gct | ttt | 5879 |
| Val | Ser | Gly | Asp | Arg | Ile | His | Cys | Leu | Asp | Ile | Leu | Phe | Ala | Phe |
| | | 1860 | | | | 1865 | | | | 1870 | | | | |

| aca | aag | cgg | gtt | cta | gga | gag | agt | gga | gag | atg | gat | gct | cta | cga | 5924 |
| Thr | Lys | Arg | Val | Leu | Gly | Glu | Ser | Gly | Glu | Met | Asp | Ala | Leu | Arg |
| | 1875 | | | | 1880 | | | | 1885 | | | | | |

| ata | cag | atg | gaa | gag | cga | ttc | atg | gct | tcc | aat | cct | tcc | aag | gtc | 5969 |
| Ile | Gln | Met | Glu | Glu | Arg | Phe | Met | Ala | Ser | Asn | Pro | Ser | Lys | Val |
| 1890 | | | | | 1895 | | | | 1900 | | | | | |

| tcc | tat | cag | cca | atc | act | act | act | tta | aaa | cga | aaa | caa | gag | gaa | 6014 |
| Ser | Tyr | Gln | Pro | Ile | Thr | Thr | Thr | Leu | Lys | Arg | Lys | Gln | Glu | Glu |
| | | 1905 | | | | 1910 | | | | 1915 | | | | |

| gta | tct | gct | gtc | att | att | cag | cgt | gct | tac | aga | cgc | cac | ctt | tta | 6059 |
| Val | Ser | Ala | Val | Ile | Ile | Gln | Arg | Ala | Tyr | Arg | Arg | His | Leu | Leu |
| | 1920 | | | | 1925 | | | | 1930 | | | | | |

| aag | cga | act | gta | aaa | caa | gct | tcc | ttt | acg | tac | aat | aaa | aac | aaa | 6104 |
| Lys | Arg | Thr | Val | Lys | Gln | Ala | Ser | Phe | Thr | Tyr | Asn | Lys | Asn | Lys |
| | | 1935 | | | | 1940 | | | | 1945 | | | | |

| atc | aaa | ggt | ggg | gct | aat | ctt | ctt | ata | aaa | gaa | gac | atg | ata | att | 6149 |
| Ile | Lys | Gly | Gly | Ala | Asn | Leu | Leu | Ile | Lys | Glu | Asp | Met | Ile | Ile |
| | 1950 | | | | 1955 | | | | 1960 | | | | | |

| gac | aga | ata | aat | gaa | aac | tct | att | aca | gaa | aaa | act | gat | ctg | acc | 6194 |
| Asp | Arg | Ile | Asn | Glu | Asn | Ser | Ile | Thr | Glu | Lys | Thr | Asp | Leu | Thr |
| 1965 | | | | | 1970 | | | | 1975 | | | | | |

| atg | tcc | act | gca | gct | tgt | cca | cct | tcc | tat | gac | cgg | gtg | aca | aag | 6239 |
| Met | Ser | Thr | Ala | Ala | Cys | Pro | Pro | Ser | Tyr | Asp | Arg | Val | Thr | Lys |
| | 1980 | | | | 1985 | | | | 1990 | | | | | |

| cca | att | gtg | gaa | aaa | cat | gag | caa | gaa | ggc | aaa | gat | gaa | aaa | gcc | 6284 |
| Pro | Ile | Val | Glu | Lys | His | Glu | Gln | Glu | Gly | Lys | Asp | Glu | Lys | Ala |
| | | 1995 | | | | 2000 | | | | 2005 | | | | |

| aaa | ggg | aaa | taa atgaaataa ataaaaataa ttgggtgaca aattgtttac | 6336 |
| Lys | Gly | Lys | | agcctgtgaa ggtgatgtat ttttatcaac aggactcctt taggaggtca atgccaaact    6396 gactgttttt acacaaatct ccttaaggtc agtgcctaca ataagacagt gacccctttgt   6456 cagcaaactg tgactctgtg taaagggag atgaccttga caggaggtta ctgttctcac    6516 taccagctga cactgctgaa gataagatgc acaatggcta gtcagactgt agggaccagt   6576 ttcaaggggt gcaaacctgt gattttgggg ttgtttaaca tgaaacactt tagtgtagta   6636 attgtatcca ctgtttgcat ttcaactgcc acatttgtca catttttatg gaatctgtta   6696 gtggattcat cttttttgtta atccatgtgt ttattatatg tgactatttt tgtaaacgaa   6756 gtttctgttg agaaataggc taaggacctc tataacaggt atgccacctg gggggtatgg   6816 caaccacatg gccctcccag ctacacaaag tcgtggtttg catgagggca tgctgcactt   6876 agagatcatg catgagaaaa agtcacaaga aaaacaaatt cttaaatttc accatatttc   6936 tgggaggggt aattgggtga taagtggagg tgctttgttg atcttgtttt gcgaaatcca   6996 gcccctagac caagtagatt atttgtgggt aggccagtaa atcttagcag gtgcaaactt   7056

-continued

```
cattcaaatg tttggagtca taaatgttat gtttcttttt gttgtattaa aaaaaaaacc    7116
tgaatagtga atattgcccc tcaccctcca ccgccagaag actgaattga ccaaaattac    7176
tctttataaa tttctgcttt ttcctgcact ttgtttagcc atctttgggc tctcagcaag    7236
gttgacactg tatatgttaa tgaaatgcta tttattatgt aaatagtcat tttaccctgt    7296
ggtgcacgtt tgagcaaaca aataatgacc taagcacagt atttattgca tcaaatatgt    7356
accacaagaa atgtagagtg caagctttac acaggtaata aaatgtattc tgtaccattt    7416
atagatagtt tggatgctat caatgcatgt ttatattacc atgctgctgt atctggtttc    7476
tctcactgct cagaatctca tttatgagaa accatatgtc agtggtaaag tcaaggaaat    7536
tgttcaacag atctcattta tttaagtcat taagcaatag tttgcagcac tttaacagct    7596
ttttggttat ttttacattt taagtggata acatatggta tatagccaga ctgtacagac    7656
atgtttaaaa aaacacactg cttaacctat taaatatgtg tttagaattt tataagcaaa    7716
tataaatact gtaaaagtc actttatttt atttttcagc attatgtaca taaatatgaa    7776
gaggaaatta tcttcaggtt gatatcacaa tcactttttct tactttctgt ccatagtact    7836
ttttcatgaa agaaatttgc taaataagac atgaaaacaa gactgggtag ttgtagattt    7896
ctgcttttta aattacattt gctaatttta gattatttca caattttaag gagcaaaata    7956
ggttcacgat tcatatccaa attatgcttt gcaattggaa aagggtttaa aattttattt    8016
atatttctgg tagtacctgt actaactgaa ttgaaggtag tgcttatgtt attttttgttc    8076
ttttttctg acttcggttt atgttttcat ttctttggag taatgctgct ctagattgtt    8136
ctaaatagaa tgtgggcttc ataatttttt tttccacaaa aacagagtag tcaacttata    8196
tagtcaatta catcaggaca ttttgtgttt cttacagaag caaaccatag gctcctcttt    8256
tccttaaaac tacttagata aactgtattc gtgaactgca tgctggaaaa tgctactatt    8316
atgctaaata atgctaacca acatttaaaa tgtgcaaaac taataaagat tacatttttt    8376
atttt                                                                8381
```

<210> SEQ ID NO 6
<211> LENGTH: 2009
<212> TYPE: PRT
<213> ORGANISM: Homo sapiens

<400> SEQUENCE: 6

```
Met Glu Gln Thr Val Leu Val Pro Pro Gly Pro Asp Ser Phe Asn Phe
 1               5                  10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125
```

```
Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
    275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
            325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
            370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540
```

-continued

```
Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asn Gly Thr Thr Thr Glu Thr Glu
            675                 680                 685

Met Arg Lys Arg Arg Ser Ser Phe His Val Ser Met Asp Phe Leu
            690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
                755                 760                 765

Phe Val Asp Leu Ala Ile Thr Ile Cys Ile Val Leu Asn Thr Leu Phe
                770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
                835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
        930                 935                 940

Phe Arg Val Leu Cys Gly Glu Trp Ile Glu Thr Met Trp Asp Cys Met
945                 950                 955                 960
```

-continued

```
Glu Val Ala Gly Gln Ala Met Cys Leu Thr Val Phe Met Met Val Met
                965                 970                 975
Val Ile Gly Asn Leu Val Val Leu Asn Leu Phe Leu Ala Leu Leu Leu
            980                 985                 990
Ser Ser Phe Ser Ala Asp Asn Leu Ala Ala Thr Asp Asp Asn Glu
        995                 1000                1005
Met Asn Asn Leu Gln Ile Ala Val Asp Arg Met His Lys Gly Val
    1010                1015                1020
Ala Tyr Val Lys Arg Lys Ile Tyr Glu Phe Ile Gln Gln Ser Phe
    1025                1030                1035
Ile Arg Lys Gln Lys Ile Leu Asp Glu Ile Lys Pro Leu Asp Asp
    1040                1045                1050
Leu Asn Asn Lys Lys Asp Ser Cys Met Ser Asn His Thr Thr Glu
    1055                1060                1065
Ile Gly Lys Asp Leu Asp Tyr Leu Lys Asp Val Asn Gly Thr Thr
    1070                1075                1080
Ser Gly Ile Gly Thr Gly Ser Ser Val Glu Lys Tyr Ile Ile Asp
    1085                1090                1095
Glu Ser Asp Tyr Met Ser Phe Ile Asn Asn Pro Ser Leu Thr Val
    1100                1105                1110
Thr Val Pro Ile Ala Val Gly Glu Ser Asp Phe Glu Asn Leu Asn
    1115                1120                1125
Thr Glu Asp Phe Ser Ser Glu Ser Asp Leu Glu Glu Ser Lys Glu
    1130                1135                1140
Lys Leu Asn Glu Ser Ser Ser Ser Glu Gly Ser Thr Val Asp
    1145                1150                1155
Ile Gly Ala Pro Val Glu Glu Gln Pro Val Val Glu Pro Glu Glu
    1160                1165                1170
Thr Leu Glu Pro Glu Ala Cys Phe Thr Glu Gly Cys Val Gln Arg
    1175                1180                1185
Phe Lys Cys Cys Gln Ile Asn Val Glu Glu Gly Arg Gly Lys Gln
    1190                1195                1200
Trp Trp Asn Leu Arg Arg Thr Cys Phe Arg Ile Val Glu His Asn
    1205                1210                1215
Trp Phe Glu Thr Phe Ile Val Phe Met Ile Leu Leu Ser Ser Gly
    1220                1225                1230
Ala Leu Ala Phe Glu Asp Ile Tyr Ile Asp Gln Arg Lys Thr Ile
    1235                1240                1245
Lys Thr Met Leu Glu Tyr Ala Asp Lys Val Phe Thr Tyr Ile Phe
    1250                1255                1260
Ile Leu Glu Met Leu Leu Lys Trp Val Ala Tyr Gly Tyr Gln Thr
    1265                1270                1275
Tyr Phe Thr Asn Ala Trp Cys Trp Leu Asp Phe Leu Ile Val Asp
    1280                1285                1290
Val Ser Leu Val Ser Leu Thr Ala Asn Ala Leu Gly Tyr Ser Glu
    1295                1300                1305
Leu Gly Ala Ile Lys Ser Leu Arg Thr Leu Arg Ala Leu Arg Pro
    1310                1315                1320
Leu Arg Ala Leu Ser Arg Phe Glu Gly Met Arg Val Val Val Asn
    1325                1330                1335
Ala Leu Leu Gly Ala Ile Pro Ser Ile Met Asn Val Leu Leu Val
    1340                1345                1350
```

```
Cys Leu Ile Phe Trp Leu Ile Phe Ser Ile Met Gly Val Asn Leu
    1355            1360            1365

Phe Ala Gly Lys Phe Tyr His Cys Ile Asn Thr Thr Thr Gly Asp
    1370            1375            1380

Arg Phe Asp Ile Glu Asp Val Asn Asn His Thr Asp Cys Leu Lys
    1385            1390            1395

Leu Ile Glu Arg Asn Glu Thr Ala Arg Trp Lys Asn Val Lys Val
    1400            1405            1410

Asn Phe Asp Asn Val Gly Phe Gly Tyr Leu Ser Leu Leu Gln Val
    1415            1420            1425

Ala Thr Phe Lys Gly Trp Met Asp Ile Met Tyr Ala Ala Val Asp
    1430            1435            1440

Ser Arg Asn Val Glu Leu Gln Pro Lys Tyr Glu Lys Ser Leu Tyr
    1445            1450            1455

Met Tyr Leu Tyr Phe Val Ile Phe Ile Ile Phe Gly Ser Phe Phe
    1460            1465            1470

Thr Leu Asn Leu Phe Ile Gly Val Ile Ile Asp Asn Phe Asn Gln
    1475            1480            1485

Gln Lys Lys Lys Phe Gly Gly Gln Asp Ile Phe Met Thr Glu Glu
    1490            1495            1500

Gln Lys Lys Tyr Tyr Asn Ala Met Lys Lys Leu Gly Ser Lys Lys
    1505            1510            1515

Pro Gln Lys Pro Ile Pro Arg Pro Gly Asn Lys Phe Gln Gly Met
    1520            1525            1530

Val Phe Asp Phe Val Thr Arg Gln Val Phe Asp Ile Ser Ile Met
    1535            1540            1545

Ile Leu Ile Cys Leu Asn Met Val Thr Met Met Val Glu Thr Asp
    1550            1555            1560

Asp Gln Ser Glu Tyr Val Thr Thr Ile Leu Ser Arg Ile Asn Leu
    1565            1570            1575

Val Phe Ile Val Leu Phe Thr Gly Glu Cys Val Leu Lys Leu Ile
    1580            1585            1590

Ser Leu Arg His Tyr Tyr Phe Thr Ile Gly Trp Asn Ile Phe Asp
    1595            1600            1605

Phe Val Val Val Ile Leu Ser Ile Val Gly Met Phe Leu Ala Glu
    1610            1615            1620

Leu Ile Glu Lys Tyr Phe Val Ser Pro Thr Leu Phe Arg Val Ile
    1625            1630            1635

Arg Leu Ala Arg Ile Gly Arg Ile Leu Arg Leu Ile Lys Gly Ala
    1640            1645            1650

Lys Gly Met Arg Thr Leu Leu Phe Ala Leu Met Met Ser Leu Pro
    1655            1660            1665

Ala Leu Phe Asn Ile Gly Leu Leu Leu Phe Leu Val Met Phe Ile
    1670            1675            1680

Tyr Ala Ile Phe Gly Met Ser Asn Phe Ala Tyr Val Lys Arg Glu
    1685            1690            1695

Val Gly Ile Asp Asp Met Phe Asn Phe Glu Thr Phe Gly Asn Ser
    1700            1705            1710

Met Ile Cys Leu Phe Gln Ile Thr Thr Ser Ala Gly Trp Asp Gly
    1715            1720            1725

Leu Leu Ala Pro Ile Leu Asn Ser Lys Pro Pro Asp Cys Asp Pro
    1730            1735            1740
```

-continued

| | | | | | | | | | |
|---|---|---|---|---|---|---|---|---|---|
| Asn | Lys | Val | Asn | Pro | Gly | Ser | Ser | Val | Lys | Gly | Asp | Cys | Gly | Asn |
| | 1745 | | | | 1750 | | | | 1755 | |

Asn Lys Val Asn Pro Gly Ser Ser Val Lys Gly Asp Cys Gly Asn
    1745                1750                1755

Pro Ser Val Gly Ile Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005

<210> SEQ ID NO 7
<211> LENGTH: 8381
<212> TYPE: DNA
<213> ORGANISM: Homo sapiens

<400> SEQUENCE: 7

```
atactgcaga ggtctctggt gcatgtgtgt atgtgtgcgt ttgtgtgtgt ttgtgtgtct      60
gtgtgttctg ccccagtgag actgcagccc ttgtaaatac tttgacacct tttgcaagaa     120
ggaatctgaa caattgcaac tgaaggcaca ttgttatcat ctcgtctttg ggtgatgctg     180
ttcctcactg cagatggata attttccttt taatcaggaa tttcatatgc agaataaatg     240
gtaattaaaa tgtgcaggat gacaagatgg agcaaacagt gcttgtacca ccaggacctg     300
acagcttcaa cttcttcacc agagaatctc ttgcggctat tgaaagacgc attgcagaag     360
aaaaggcaaa gaatcccaaa ccagacaaaa aagatgacga cgaaaatggc ccaaagccaa     420
atagtgactt ggaagctgga aagaaccttc catttattta tggagacatt cctccagaga     480
tggtgtcaga gccctggag gacctggacc cctactatat caataagaaa acttttatag     540
```

```
                                         -continued
tattgaataa attgaaggcc atcttccggt tcagtgccac ctctgccctg tacattttaa      600 ctccottcaa tcctcttagg aaaatagcta ttaagatttt ggtacattca ttattcagca      660
tgctaattat gtgcactatt ttgacaaact gtgtgtttat gacaatgagt aaccctcctg      720
attggacaaa gaatgtagaa tacaccttca caggaatata tacttttgaa tcacttataa      780
aaattattgc aagggattc tgtttagaag attttacttt ccttcgggat ccatggaact       840
ggctcgattt cactgtcatt acatttgcgt acgtcacaga gtttgtggac ctgggcaatg      900
tctcggcatt gagaacattc agagttctcc gagcattgaa gacgatttca gtcattccag      960
gcctgaaaac cattgtggga gccctgatcc agtctgtgaa gaagctctca gatgtaatga     1020
tcctgactgt gttctgtctg agcgtatttg ctctaattgg gctgcagctg ttcatgggca     1080
acctgaggaa taaatgtata caatggcctc ccaccaatgc ttccttggag gaacatagta     1140
tagaaaagaa tataactgtg aattataatg gtacacttat aaatgaaact gtctttgagt     1200
ttgactggaa gtcatatatt caagattcaa gatatcatta tttcctggag gttttttag      1260 atgcactact atgtggaaat agctctgatg caggccaatg tccagaggga tatatgtgtg     1320
tgaaagctgg tagaaatccc aattatggct acacaagctt tgataccttc agttgggctt     1380
ttttgtcctt gttcgacta atgactcagg acttctggga aaatctttat caactgacat      1440
tacgtgctgc tggaaaacg tacatgatat tttttgtatt ggtcattttc ttgggctcat       1500
tctacctaat aaatttgatc ctggctgtgg tggccatggc ctacgaggaa cagaatcagg     1560
ccaccttgga agaagcagaa cagaaagagg ccgaatttca gcagatgatt gaacagctta     1620
aaaagcaaca ggaggcagct cagcaggcag caacggcaac tgcctcagaa cattccagag     1680
agcccagtgc agcaggcagg ctctcagaca gctcatctga agcctctaag ttgagttcca     1740
agagtgctaa ggaaagaaga aatcggagga agaaaagaaa acagaaagag cagtctggtg     1800
gggaagagaa agatgaggat gaattccaaa aatctgaatc tgaggacagc atcaggagga     1860
aaggttttcg cttctccatt gaagggaacc gattgacata tgaaaagagg tactcctccc     1920
cacaccagtc tttgttgagc atccgtggct ccctattttc accaaggcga aatagcagaa     1980 caagccttt cagctttaga gggcgagcaa aggatgtggg atctgagaac gacttcgcag      2040
atgatgagca cagcaccttt gaggataacg agagccgtag agattccttg tttgtgcccc     2100
gacgacacgg agagagacgc aacagcaacc tgagtcagac cagtaggtca tcccggatgc     2160
tggcagtgtt tccagcgaat gggaagatgc acagcactgt ggattgcaat ggtgtggttt     2220
ccttggttgg tggaccttca gttcctacat cgcctgttgg acagcttctg ccagaggtga     2280
taatagataa gccagctact gatgacaatg gaacaaccac tgaaactgaa atgagaaaga     2340
gaaggtcaag ttctttccac gtttccatgg actttctaga agatcottcc caaaggcaac     2400 gagcaatgag tatagccagc attctaacaa atacagtaga agaacttgaa gaatccaggc     2460
agaaatgccc accctgttgg tataaatttt ccaacatatt cttaatctgg gactgttctc     2520
catattggtt aaaagtgaaa catgttgtca acctggttgt gatggaccca tttgttgacc     2580
tggccatcac catctgtatt gtcttaaata ctctttttcat ggccatggag cactatccaa     2640
tgacggacca tttcaataat gtgcttacag taggaaactt ggttttcact gggatcttta     2700
cagcagaaat gttctgaaa attattgcca tggatcctta ctattattc caagaaggct       2760 ggaatatctt tgacggtttt attgtgaggc ttagcctggt agaacttgga ctcgccaatg     2820
tggaaggatt atctgttctc cgttcatttc gattgctgcg agttttcaag ttggcaaaat     2880
cttggccaac gttaaatatg ctaataaaga tcatcggcaa ttccgtgggg gctctgggaa     2940
```

```
atttaacccct cgtcttggcc atcatcgtct tcatttttgc cgtggtcggc atgcagctct    3000
ttggtaaaag ctacaaagat tgtgtctgca agatcgccag tgattgtcaa ctcccacgct    3060
ggcacatgaa tgacttcttc cactccttcc tgattgtgtt ccgcgtgctg tgtggggagt    3120
ggatagagac catgtgggac tgtatggagg ttgctggtca agccatgtgc cttactgtct    3180
tcatgatggt catggtgatt ggaaacctag tggtcctgaa tctctttctg gccttgcttc    3240
tgagctcatt tagtgcagac aaccttgcag ccactgatga tgataatgaa atgaataatc    3300
tccaaattgc tgtggatagg atgcacaaag gagtagctta tgtgaaaaga aaaatatatg    3360
aatttattca acagtccttc attaggaaac aaaagatttt agatgaaatt aaaccacttg    3420
atgatctaaa caacaagaaa gacagttgta tgtccaatca tacaacagaa attgggaaag    3480
atcttgacta tcttaaagat gtaaatgaaa ctacaagtgg tataggaact ggcagcagtg    3540
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca agagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa acaatggtg gaacctgaga aggacgtgtt    3900
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctaag agccttatct cgatttgaag    4260
ggatgagggt ggttgtgaat gcccttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatctttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctatacctcg accaggaaac aaatttcaag    4860
gaatggtctt tgacttcgta accagacaag tttttgacat aagcatcatg attctcatct    4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tattttacca ttggatggaa tatttttgat tttgtggttg    5100
tcattctctc cattgtaggt atgtttcttg ccgagctgat agaaaagtat ttcgtgtccc    5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340
```

```
ttgcctatgt taagagggaa gttgggatcg atgacatgtt caactttgag acctttggca   5400
acagcatgat ctgcctattc caaattacaa cctctgctgg ctgggatgga ttgctagcac   5460
ccattctcaa cagtaagcca cccgactgtg accctaataa agttaaccct ggaagctcag   5520
ttaagggaga ctgtgggaac ccatctgttg gaattttctt ttttgtcagt tacatcatca   5580
tatccttcct ggttgtggtg aacatgtaca tcgcggtcat cctggagaac ttcagtgttg   5640
ctactgaaga aagtgcagag cctctgagtg aggatgactt tgagatgttc tatgaggttt   5700
gggagaagtt tgatcccgat gcaactcagt tcatggaatt tgaaaaatta tctcagtttg   5760
cagctgcgct tgaaccgcct ctcaatctgc acaaccaaa caaactccag ctcattgcca   5820
tggatttgcc catggtgagt ggtgaccgga tccactgtct tgatatctta tttgctttta   5880
caaagcgggt tctaggagag agtggagaga tggatgctct acgaatacag atggaagagc   5940
gattcatggc ttccaatcct tccaaggtct cctatcagcc aatcactact actttaaaac   6000
gaaaacaaga ggaagtatct gctgtcatta ttcagcgtgc ttacagacgc caccttttaa   6060
agcgaactgt aaaacaagct tcctttacgt acaataaaaa caaaatcaaa ggtggggcta   6120
atcttcttat aaaagaagac atgataattg acagaataaa tgaaaactct attacagaaa   6180
aaactgatct gaccatgtcc actgcagctt gtccaccttc ctatgaccgg gtgacaaagc   6240
caattgtgga aaaacatgag caagaaggca aagatgaaaa agccaagggg aaataaatga   6300
aaataaataa aaataattgg gtgacaaatt gtttacagcc tgtgaaggtg atgtattttt   6360
atcaacagga ctcctttagg aggtcaatgc caaactgact gtttttacac aaatctcctt   6420
aaggtcagtg cctacaataa gacagtgacc ccttgtcagc aaactgtgac tctgtgtaaa   6480
ggggagatga ccttgacagg aggttactgt tctcactacc agctgacact gctgaagata   6540
agatgcacaa tggctagtca gactgtaggg accagtttca aggggtgcaa acctgtgatt   6600
ttggggttgt ttaacatgaa acactttagt gtagtaattg tatccactgt ttgcatttca   6660
actgccacat ttgtcacatt tttatggaat ctgttagtgg attcatcttt ttgttaatcc   6720
atgtgtttat tatatgtgac tattttttgta acgaagttt ctgttgagaa ataggctaag   6780
gacctctata acaggtatgc cacctggggg gtatggcaac cacatggccc tcccagctac   6840
acaaagtcgt ggtttgcatg agggcatgct gcacttagag atcatgcatg agaaaaagtc   6900
acaagaaaaa caaattctta aatttcacca tatttctggg aggggtaatt gggtgataag   6960
tggaggtgct ttgttgatct tgttttgcga aatccagccc ctagaccaag tagattattt   7020
gtgggtaggc cagtaaatct tagcaggtgc aaacttcatt caaatgtttg gagtcataaa   7080
tgttatgttt cttttgttg tattaaaaaa aaaacctgaa tagtgaatat tgcccctcac   7140
cctccaccgc cagaagactg aattgaccaa aattactctt tataaatttc tgcttttccc   7200
tgcactttgt ttagccatct ttgggctctc agcaaggttg acactgtata tgttaatgaa   7260
atgctattta ttatgtaaat agtcattta ccctgtggtg cacgtttgag caaacaaata   7320
atgacctaag cacagtattt attgcatcaa atatgtacca caagaaatgt agagtgcaag   7380
ctttacacag gtaataaaat gtattctgta ccatttatag atagtttgga tgctatcaat   7440
gcatgtttat attaccatgc tgctgtatct ggtttctctc actgctcaga atctcattta   7500
tgagaaacca tatgtcagtg gtaaagtcaa ggaaattgtt caacagatct catttattta   7560
agtcattaag caatagtttg cagcacttta acagcttttt ggttattttt acattttaag   7620
tggataacat atggtatata gccagactgt acagacatgt ttaaaaaaac acactgctta   7680
acctattaaa tatgtgttta gaattttata agcaaatata aatactgtaa aaagtcactt   7740
```

-continued

| | |
|---|---|
| tattttatttt ttcagcatta tgtacataaa tatgaagagg aaattatctt caggttgata | 7800 |
| tcacaatcac ttttcttact ttctgtccat agtacttttt catgaaagaa atttgctaaa | 7860 |
| taagacatga aaacaagact gggtagttgt agatttctgc tttttaaatt acatttgcta | 7920 |
| attttagatt atttcacaat tttaaggagc aaaataggtt cacgattcat atccaaatta | 7980 |
| tgctttgcaa ttggaaaagg gtttaaaatt ttatttatat ttctggtagt acctgtacta | 8040 |
| actgaattga aggtagtgct tatgttattt ttgttctttt tttctgactt cggtttatgt | 8100 |
| tttcatttct ttggagtaat gctgctctag attgttctaa atagaatgtg ggcttcataa | 8160 |
| tttttttttc cacaaaaaca gagtagtcaa cttatatagt caattacatc aggacatttt | 8220 |
| gtgtttctta cagaagcaaa ccataggctc ctcttttcct taaaactact tagataaact | 8280 |
| gtattcgtga actgcatgct ggaaaatgct actattatgc taaataatgc taaccaacat | 8340 |
| ttaaaatgtg caaaactaat aaagattaca ttttttattt t | 8381 |

<210> SEQ ID NO 8
<211> LENGTH: 8381
<212> TYPE: DNA
<213> ORGANISM: Homo sapiens

<400> SEQUENCE: 8

| | |
|---|---|
| atactgcaga ggtctctggt gcatgtgtgt atgtgtgcgt ttgtgtgtgt ttgtgtgtct | 60 |
| gtgtgttctg ccccagtgag actgcagccc ttgtaaatac tttgacacct tttgcaagaa | 120 |
| ggaatctgaa caattgcaac tgaaggcaca ttgttatcat ctcgtctttg ggtgatgctg | 180 |
| ttcctcactg cagatggata atttttccttt taatcaggaa tttcatatgc agaataaatg | 240 |
| gtaattaaaa tgtgcaggat gacaagatgg agcaaacagt gcttgtacca ccaggacctg | 300 |
| acagcttcaa cttcttcacc agagaatctc ttgcggctat tgaaagacgc attgcagaag | 360 |
| aaaaggcaaa gaatcccaaa ccagacaaaa aagatgacga cgaaaatggc ccaaagccaa | 420 |
| atagtgactt ggaagctgga aagaaccttc catttattta tggagacatt cctccagaga | 480 |
| tggtgtcaga gccctggag gacctggacc cctactatat caataagaaa acttttatag | 540 |
| tattgaataa attgaaggcc atcttccggt tcagtgccac ctctgccctg tacattttaa | 600 |
| ctcccttcaa tcctcttagg aaaatagcta ttaagatttt ggtacattca ttattcagca | 660 |
| tgctaattat gtgcactatt ttgacaaact gtgtgtttat gacaatgagt aaccctcctg | 720 |
| attggacaaa gaatgtagaa tacaccttca caggaatata tacttttgaa tcacttataa | 780 |
| aaattattgc aaggggattc tgtttagaag atttttactt ccttcgggat ccatggaact | 840 |
| ggctcgattt cactgtcatt acatttgcgt acgtcacaga gtttgtggac ctgggcaatg | 900 |
| tctcggcatt gagaacattc agagttctcc gagcattgaa gacgatttca gtcattccag | 960 |
| gcctgaaaac cattgtggga gccctgatcc agtctgtgaa gaagctctca gatgtaatga | 1020 |
| tcctgactgt gttctgtctg agcgtatttg ctctaattgg gctgcagctg ttcatgggca | 1080 |
| acctgaggaa taaatgtata caatggcctc ccaccaatgc ttccttggag gaacatagta | 1140 |
| tagaaaagaa tataactgtg aattataatg gtacacttat aaatgaaact gtctttgagt | 1200 |
| ttgactggaa gtcatatatt caagattcaa gatatcatta tttcctggag gttttttttag | 1260 |
| atgcactact atgtggaaat agctctgatg caggccaatg tccagaggga tatatgtgtg | 1320 |
| tgaaagctgg tagaaatccc aattatggct acacaagctt tgataccttc agttgggctt | 1380 |
| ttttgtcctt gttcgactaa tgactcagg acttctggga aaatctttat caactgacat | 1440 |
| tacgtgctgc tgggaaaacg tacatgatat tttttgtatt ggtcatttttc ttgggctcat | 1500 |

-continued

```
tctacctaat aaatttgatc ctggctgtgg tggccatggc ctacgaggaa cagaatcagg    1560
ccaccttgga agaagcagaa cagaaagagg ccgaatttca gcagatgatt gaacagctta    1620
aaaagcaaca ggaggcagct cagcaggcag caacggcaac tgcctcagaa cattccagag    1680
agcccagtgc agcaggcagg ctctcagaca gctcatctga agcctctaag ttgagttcca    1740
agagtgctaa ggaaagaaga aatcggagga agaaaagaaa acagaaagag cagtctggtg    1800
gggaagagaa agatgaggat gaattccaaa aatctgaatc tgaggacagc atcaggagga    1860
aaggttttcg cttctccatt gaagggaacc gattgacata tgaaaagagg tactcctccc    1920
cacaccagtc tttgttgagc atccgtggct ccctatttcc accaaggcga aatagcagaa    1980
caagcctttt cagctttaga gggcgagcaa aggatgtggg atctgagaac gacttcgcag    2040
atgatgagca cagcaccttt gaggataacg agagccgtag agattccttg tttgtgcccc    2100
gacgacacgg agagagacgc aacagcaacc tgagtcagac cagtaggtca tcccggatgc    2160
tggcagtgtt tccagcgaat gggaagatgc acagcactgt ggattgcaat ggtgtggttt    2220
ccttggttgg tggaccttca gttcctacat cgcctgttgg acagcttctg ccagaggtga    2280
taatagataa gccagctact gatgacaatg aacaaccac tgaaactgaa atgagaaaga    2340
gaaggtcaag ttcttttccac gttttccatgg actttctaga agatccttcc caaaggcaac    2400
gagcaatgag tatagccagc attctaacaa atacagtaga agaacttgaa gaatccaggc    2460
agaaatgccc accctgttgg tataaatttt ccaacatatt cttaatctgg gactgttctc    2520
catattggtt aaaagtgaaa catgttgtca acctggttgt gatggaccca tttgttgacc    2580
tggccatcac catctgtatt gtcttaaata ctcttttcat ggccatggag cactatccaa    2640
tgacggacca tttcaataat gtgcttacag taggaaactt ggttttcact gggatcttta    2700
cagcagaaat gtttctgaaa attattgcca tggatcctta ctattatttc caagaaggct    2760
ggaatatctt tgacggtttt attgtgacgc ttagcctggt agaacttgga ctcgccaatg    2820
tggaaggatt atctgttctc cgttcatttc gattgctgcg agttttcaag ttggcaaaat    2880
cttggccaac gttaaatatg ctaataaaga tcatcggcaa ttccgtgggg gctctgggaa    2940
atttaaccct cgtcttggcc atcatcgtct tcattttgc cgtggtcggc atgcagctct    3000
ttggtaaaag ctacaaagat tgtgtctgca agatcgccag tgattgtcaa ctcccacgct    3060
ggcacatgaa tgacttcttc cactccttcc tgattgtgtt ccgcgtgctg tgtggggagt    3120
ggatagagac catgtgggac tgtatggagg ttgccggtca agccatgtgc cttactgtct    3180
tcatgatggt catggtgatt ggaaacctag tggtcctgaa tctctttctg gccttgcttc    3240
tgagctcatt tagtgcagac aaccttgcag ccactgatga tgataatgaa atgaataatc    3300
tccaaattgc tgtggatagg atgcacaaag gagtagctta tgtgaaaaga aaaatatatg    3360
aatttattca acagtccttc attaggaaac aaaagatttt agatgaaatt aaaccacttg    3420
atgatctaaa caacaagaaa gacagttgta tgtccaatca tacaacagaa attgggaaag    3480
atcttgacta tcttaaagat gtaaatggaa ctacaagtgg tataggaact ggcagcagtg    3540
ttgaaaaata cattattgat gaaagtgatt acatgtcatt cataaacaac cccagtctta    3600
ctgtgactgt accaattgct gtaggagaat ctgactttga aaatttaaac acggaagact    3660
ttagtagtga atcggatctg gaagaaagca agagaaact gaatgaaagc agtagctcat    3720
cagaaggtag cactgtggac atcggcgcac ctgtagaaga acagcccgta gtggaacctg    3780
aagaaactct tgaaccagaa gcttgtttca ctgaaggctg tgtacaaaga ttcaagtgtt    3840
gtcaaatcaa tgtggaagaa ggcagaggaa aacaatggtg gaacctgaga aggacgtgtt    3900
```

```
tccgaatagt tgaacataac tggtttgaga ccttcattgt tttcatgatt ctccttagta    3960
gtggtgctct ggcatttgaa gatatatata ttgatcagcg aaagacgatt aagacgatgt    4020
tggaatatgc tgacaaggtt ttcacttaca ttttcattct ggaaatgctt ctaaaatggg    4080
tggcatatgg ctatcaaaca tatttcacca atgcctggtg ttggctggac ttcttaattg    4140
ttgatgtttc attggtcagt ttaacagcaa atgccttggg ttactcagaa cttggagcca    4200
tcaaatctct caggacacta agagctctga gacctctaag agccttatct cgatttgaag    4260
ggatgagggt ggttgtgaat gcccttttag gagcaattcc atccatcatg aatgtgcttc    4320
tggtttgtct tatattctgg ctaattttca gcatcatggg cgtaaatttg tttgctggca    4380
aattctacca ctgtattaac accacaactg gtgacaggtt tgacatcgaa gacgtgaata    4440
atcatactga ttgcctaaaa ctaatagaaa gaaatgagac tgctcgatgg aaaaatgtga    4500
aagtaaactt tgataatgta ggatttgggt atctctcttt gcttcaagtt gccacattca    4560
aaggatggat ggatataatg tatgcagcag ttgattccag aaatgtggaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaagaa    4740
agtttggagg tcaagacatc tttatgacag aagaacagaa gaaatactat aatgcaatga    4800
aaaaattagg atcgaaaaaa ccgcaaaagc ctatacctcg accaggaaac aaatttcaag    4860
gaatggtctt tgacttcgta accagacaag tttttgacat aagcatcatg attctcatct    4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tatttttacca ttggatggaa tatttttgat tttgtggttg    5100
tcattctctc cattgtaggt atgtttcttg ccgagctgat agaaaagtat ttcgtgtccc    5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340 tgcctatgt taagagggaa gttgggatcg atgacatgtt caactttgag accttttggca    5400 acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc cacaaccaaa caaactccag ctcattgcca    5820
tggatttgcc catggtgagt ggtgaccgga tccactgtct tgatatctta tttgctttta    5880
caaagcgggt tctaggagag agtggagaga tggatgctct acgaatacag atggaagagc    5940
gattcatggc ttccaatcct tccaaggtct cctatcagcc aatcactact actttaaaaac    6000 gaaaacaaga ggaagtatct gctgtcatta ttcagcgtgc ttacagacgc caccttttaa    6060
agcgaactgt aaaacaagct tcctttacgt acaataaaaa caaatcaaa ggtgggcta    6120 atcttcttat aaaagaagac atgataattg acagaataaa tgaaaactct attacagaaa    6180
aaactgatct gaccatgtcc actgcagctt gtccacctcc ctatgaccgg gtgacaaagc    6240
caattgtgga aaaacatgag caagaaggca agatgaaaa agccaagggg aaataaatga    6300
```

```
aaataaataa aaataattgg gtgacaaatt gtttacagcc tgtgaaggtg atgtattttt      6360
atcaacagga ctcctttagg aggtcaatgc caaactgact gtttttacac aaatctcctt      6420
aaggtcagtg cctacaataa gacagtgacc ccttgtcagc aaactgtgac tctgtgtaaa      6480
ggggagatga ccttgacagg aggttactgt tctcactacc agctgacact gctgaagata      6540
agatgcacaa tggctagtca gactgtaggg accagtttca aggggtgcaa acctgtgatt      6600
ttggggttgt ttaacatgaa acactttagt gtagtaattg tatccactgt ttgcatttca      6660
actgccacat ttgtcacatt tttatggaat ctgttagtgg attcatcttt ttgttaatcc      6720
atgtgtttat tatatgtgac tatttttgta aacgaagttt ctgttgagaa ataggctaag      6780
gacctctata acaggtatgc cacctggggg gtatggcaac cacatggccc tcccagctac      6840
acaaagtcgt ggtttgcatg agggcatgct gcacttagag atcatgcatg agaaaaagtc      6900
acaagaaaaa caaattctta aatttcacca tatttctggg aggggtaatt gggtgataag      6960
tggaggtgct tgttgatct tgttttgcga aatccagccc ctagaccaag tagattattt      7020
gtgggtaggc cagtaaatct tagcaggtgc aaacttcatt caaatgtttg gagtcataaa      7080
tgttatgttt cttttttgttg tattaaaaaa aaaacctgaa tagtgaatat tgcccctcac      7140
cctccaccgc cagaagactg aattgaccaa aattactctt tataaatttc tgcttttttcc    7200 tgcactttgt ttagccatct ttgggctctc agcaaggttg acactgtata tgttaatgaa      7260 atgctatta ttatgtaaat agtcatttta ccctgtggtg cacgtttgag caaacaaata      7320
atgacctaag cacagtattt attgcatcaa atatgtacca caagaaatgt agagtgcaag      7380
ctttacacag gtaataaaat gtattctgta ccatttatag atagtttgga tgctatcaat      7440
gcatgtttat attaccatgc tgctgtatct ggtttctctc actgtcaga atctcattta      7500 tgagaaacca tatgtcagtg gtaaagtcaa ggaaattgtt caacagatct catttattta    7560
agtcattaag caatagtttg cagcacttta acagctttt ggttattttt acattttaag      7620
tggataacat atggtatata gccagactgt acagacatgt ttaaaaaaac acactgctta      7680
acctattaaa tatgtgttta gaatttttata agcaaatata aatactgtaa aaagtcactt      7740
tatttatttt ttcagcatta tgtacataaa tatgaagagg aaattatctt caggttgata      7800
tcacaatcac ttttcttact ttctgtccat agtactttttt catgaaagaa atttgctaaa    7860
taagacatga aaacaagact gggtagttgt agatttctgc tttttaaatt acatttgcta      7920
attttagatt atttcacaat tttaaggagc aaaataggtt cacgattcat atccaaatta     7980
tgctttgcaa ttggaaaagg gtttaaaatt ttatttatat ttctggtagt acctgtacta     8040
actgaattga aggtagtgct tatgttattt ttgttctttt tttctgactt cggtttatgt     8100
tttcatttct ttggagtaat gctgctctag attgttctaa atagaatgtg ggcttcataa     8160 ttttttttc cacaaaaaca gagtagtcaa cttatatagt caattacatc aggacatttt      8220
gtgtttctta cagaagcaaa ccataggctc ctcttttcct taaaactact tagataaact     8280
gtattcgtga actgcatgct ggaaaatgct actattatgc taaataatgc taaccaacat     8340
ttaaaatgtg caaaactaat aaagattaca ttttttattt t                         8381
```

<210> SEQ ID NO 9
<211> LENGTH: 8381
<212> TYPE: DNA
<213> ORGANISM: Homo sapiens
<220> FEATURE:
<221> NAME/KEY: CDS
<222> LOCATION: (267)..(6296)

<400> SEQUENCE: 9

```
atactgcaga ggtctctggt gcatgtgtgt atgtgtgcgt ttgtgtgtgt ttgtgtgtct        60
gtgtgttctg ccccagtgag actgcagccc ttgtaaatac tttgacacct tttgcaagaa       120
ggaatctgaa caattgcaac tgaaggcaca ttgttatcat ctcgtctttg ggtgatgctg       180
ttcctcactg cagatggata attttccttt taatcaggaa tttcatatgc agaataaatg       240
gtaattaaaa tgtgcaggat gacaag atg gag caa aca gtg ctt gta cca cca        293
                             Met Glu Gln Thr Val Leu Val Pro Pro
                              1               5
```

| | | | | | | | | | |
|---|---|---|---|---|---|---|---|---|---|
| gga | cct | gac | agc | ttc | aac | ttc | ttc | acc | aga gaa tct ctt gcg gct att  341 |
| Gly | Pro | Asp | Ser | Phe | Asn | Phe | Phe | Thr | Arg Glu Ser Leu Ala Ala Ile |
| 10 | | | | 15 | | | | 20 | 25 |

```
gaa aga cgc att gca gaa gaa aag gca aag aat ccc aaa cca gac aaa        389
Glu Arg Arg Ile Ala Glu Glu Lys Ala Lys Asn Pro Lys Pro Asp Lys
             30                  35                  40 aaa gat gac gac gaa aat ggc cca aag cca aat agt gac ttg gaa gct        437
Lys Asp Asp Asp Glu Asn Gly Pro Lys Pro Asn Ser Asp Leu Glu Ala
 45                  50                  55 gga aag aac ctt cca ttt att tat gga gac att cct cca gag atg gtg        485
Gly Lys Asn Leu Pro Phe Ile Tyr Gly Asp Ile Pro Pro Glu Met Val
         60                  65                  70 tca gag ccc ctg gag gac ctg gac ccc tac tat atc aat aag aaa act        533
Ser Glu Pro Leu Glu Asp Leu Asp Pro Tyr Tyr Ile Asn Lys Lys Thr
 75                  80                  85 ttt ata gta ttg aat aaa ttg aag gcc atc ttc cgg ttc agt gcc acc        581
Phe Ile Val Leu Asn Lys Leu Lys Ala Ile Phe Arg Phe Ser Ala Thr
 90                  95                 100                 105 tct gcc ctg tac att tta act ccc ttc aat cct ctt agg aaa ata gct        629
Ser Ala Leu Tyr Ile Leu Thr Pro Phe Asn Pro Leu Arg Lys Ile Ala
             110                 115                 120 att aag att ttg gta cat tca tta ttc agc atg cta att atg tgc act        677
Ile Lys Ile Leu Val His Ser Leu Phe Ser Met Leu Ile Met Cys Thr
         125                 130                 135 att ttg aca aac tgt gtg ttt atg aca atg agt aac cct cct gat tgg        725
Ile Leu Thr Asn Cys Val Phe Met Thr Met Ser Asn Pro Pro Asp Trp
     140                 145                 150 aca aag aat gta gaa tac acc ttc aca gga ata tat act ttt gaa tca        773
Thr Lys Asn Val Glu Tyr Thr Phe Thr Gly Ile Tyr Thr Phe Glu Ser
 155                 160                 165 ctt ata aaa att att gca agg gga ttc tgt tta gaa gat ttt act ttc        821
Leu Ile Lys Ile Ile Ala Arg Gly Phe Cys Leu Glu Asp Phe Thr Phe
170                 175                 180                 185 ctt cgg gat cca tgg aac tgg ctc gat ttc act gtc att aca ttt gcg        869
Leu Arg Asp Pro Trp Asn Trp Leu Asp Phe Thr Val Ile Thr Phe Ala
             190                 195                 200 tac gtc aca gag ttt gtg gac ctg ggc aat gtc tcg gca ttg aga aca        917
Tyr Val Thr Glu Phe Val Asp Leu Gly Asn Val Ser Ala Leu Arg Thr
         205                 210                 215 ttc aga gtt ctc cga gca ttg aag acg att tca gtc att cca ggc ctg        965
Phe Arg Val Leu Arg Ala Leu Lys Thr Ile Ser Val Ile Pro Gly Leu
     220                 225                 230 aaa acc att gtg gga gcc ctg atc cag tct gtg aag aag ctc tca gat       1013
Lys Thr Ile Val Gly Ala Leu Ile Gln Ser Val Lys Lys Leu Ser Asp
 235                 240                 245 gta atg atc ctg act gtg ttc tgt ctg agc gta ttt gct cta att ggg       1061
Val Met Ile Leu Thr Val Phe Cys Leu Ser Val Phe Ala Leu Ile Gly
250                 255                 260                 265
```

-continued

| | | |
|---|---|---|
| ctg cag ctg ttc atg ggc aac ctg agg aat aaa tgt ata caa tgg cct<br>Leu Gln Leu Phe Met Gly Asn Leu Arg Asn Lys Cys Ile Gln Trp Pro<br>                270                    275                  280 | 1109 |
| ccc acc aat gct tcc ttg gag gaa cat agt ata gaa aag aat ata act<br>Pro Thr Asn Ala Ser Leu Glu Glu His Ser Ile Glu Lys Asn Ile Thr<br>             285                    290                    295 | 1157 |
| gtg aat tat aat ggt aca ctt ata aat gaa act gtc ttt gag ttt gac<br>Val Asn Tyr Asn Gly Thr Leu Ile Asn Glu Thr Val Phe Glu Phe Asp<br>         300                    305                    310 | 1205 |
| tgg aag tca tat att caa gat tca aga tat cat tat ttc ctg gag ggt<br>Trp Lys Ser Tyr Ile Gln Asp Ser Arg Tyr His Tyr Phe Leu Glu Gly<br>     315                    320                    325 | 1253 |
| ttt tta gat gca cta cta tgt gga aat agc tct gat gca ggc caa tgt<br>Phe Leu Asp Ala Leu Leu Cys Gly Asn Ser Ser Asp Ala Gly Gln Cys<br>330                    335                    340                    345 | 1301 |
| cca gag gga tat atg tgt gtg aaa gct ggt aga aat ccc aat tat ggc<br>Pro Glu Gly Tyr Met Cys Val Lys Ala Gly Arg Asn Pro Asn Tyr Gly<br>              350                    355                    360 | 1349 |
| tac aca agc ttt gat acc ttc agt tgg gct ttt ttg tcc ttg ttt cga<br>Tyr Thr Ser Phe Asp Thr Phe Ser Trp Ala Phe Leu Ser Leu Phe Arg<br>         365                    370                    375 | 1397 |
| cta atg act cag gac ttc tgg gaa aat ctt tat caa ctg aca tta cgt<br>Leu Met Thr Gln Asp Phe Trp Glu Asn Leu Tyr Gln Leu Thr Leu Arg<br>     380                    385                    390 | 1445 |
| gct gct ggg aaa acg tac atg ata ttt ttt gta ttg gtc att ttc ttg<br>Ala Ala Gly Lys Thr Tyr Met Ile Phe Phe Val Leu Val Ile Phe Leu<br>395                    400                    405 | 1493 |
| ggc tca ttc tac cta ata aat ttg atc ctg gct gtg gtg gcc atg gcc<br>Gly Ser Phe Tyr Leu Ile Asn Leu Ile Leu Ala Val Val Ala Met Ala<br>410                    415                    420                    425 | 1541 |
| tac gag gaa cag aat cag gcc acc ttg gaa gaa gca gaa cag aaa gag<br>Tyr Glu Glu Gln Asn Gln Ala Thr Leu Glu Glu Ala Glu Gln Lys Glu<br>              430                    435                    440 | 1589 |
| gcc gaa ttt cag cag atg att gaa cag ctt aaa aag caa cag gag gca<br>Ala Glu Phe Gln Gln Met Ile Glu Gln Leu Lys Lys Gln Gln Glu Ala<br>         445                    450                    455 | 1637 |
| gct cag cag gca gca acg gca act gcc tca gaa cat tcc aga gag ccc<br>Ala Gln Gln Ala Ala Thr Ala Thr Ala Ser Glu His Ser Arg Glu Pro<br>     460                    465                    470 | 1685 |
| agt gca gca ggc agg ctc tca gac agc tca tct gaa gcc tct aag ttg<br>Ser Ala Ala Gly Arg Leu Ser Asp Ser Ser Ser Glu Ala Ser Lys Leu<br>              475                    480                    485 | 1733 |
| agt tcc aag agt gct aag gaa aga aga aat cgg agg aag aaa aga aaa<br>Ser Ser Lys Ser Ala Lys Glu Arg Arg Asn Arg Arg Lys Lys Arg Lys<br>490                    495                    500                    505 | 1781 |
| cag aaa gag cag tct ggt ggg gaa gag aaa gat gag gat gaa ttc caa<br>Gln Lys Glu Gln Ser Gly Gly Glu Glu Lys Asp Glu Asp Glu Phe Gln<br>              510                    515                    520 | 1829 |
| aaa tct gaa tct gag gac agc atc agg agg aaa ggt ttt cgc ttc tcc<br>Lys Ser Glu Ser Glu Asp Ser Ile Arg Arg Lys Gly Phe Arg Phe Ser<br>         525                    530                    535 | 1877 |
| att gaa ggg aac cga ttg aca tat gaa aag agg tac tcc tcc cca cac<br>Ile Glu Gly Asn Arg Leu Thr Tyr Glu Lys Arg Tyr Ser Ser Pro His<br>     540                    545                    550 | 1925 |
| cag tct ttg ttg agc atc cgt ggc tcc cta ttt tca cca agg cga aat<br>Gln Ser Leu Leu Ser Ile Arg Gly Ser Leu Phe Ser Pro Arg Arg Asn<br> 555                    560                    565 | 1973 |
| agc aga aca agc ctt ttc agc ttt aga ggg cga gca aag gat gtg gga<br>Ser Arg Thr Ser Leu Phe Ser Phe Arg Gly Arg Ala Lys Asp Val Gly<br>570                    575                    580                    585 | 2021 |

```
tct gag aac gac ttc gca gat gat gag cac agc acc ttt gag gat aac          2069
Ser Glu Asn Asp Phe Ala Asp Asp Glu His Ser Thr Phe Glu Asp Asn
            590                 595                 600 gag agc cgt aga gat tcc ttg ttt gtg ccc cga cga cac gga gag aga          2117
Glu Ser Arg Arg Asp Ser Leu Phe Val Pro Arg Arg His Gly Glu Arg
        605                 610                 615 cgc aac agc aac ctg agt cag acc agt agg tca tcc cgg atg ctg gca          2165
Arg Asn Ser Asn Leu Ser Gln Thr Ser Arg Ser Ser Arg Met Leu Ala
    620                 625                 630 gtg ttt cca gcg aat ggg aag atg cac agc act gtg gat tgc aat ggt          2213
Val Phe Pro Ala Asn Gly Lys Met His Ser Thr Val Asp Cys Asn Gly
635                 640                 645 gtg gtt tcc ttg gtt ggt gga cct tca gtt cct aca tcg cct gtt gga          2261
Val Val Ser Leu Val Gly Gly Pro Ser Val Pro Thr Ser Pro Val Gly
650                 655                 660                 665 cag ctt ctg cca gag gtg ata ata gat aag cca gct act gat gac aat          2309
Gln Leu Leu Pro Glu Val Ile Ile Asp Lys Pro Ala Thr Asp Asp Asn
            670                 675                 680 gga aca acc act gaa act gaa atg aga aag aga agg tca agt tct ttc          2357
Gly Thr Thr Thr Glu Thr Glu Met Arg Lys Arg Arg Ser Ser Ser Phe
        685                 690                 695 cac gtt tcc atg gac ttt cta gaa gat cct tcc caa agg caa cga gca          2405
His Val Ser Met Asp Phe Leu Glu Asp Pro Ser Gln Arg Gln Arg Ala
    700                 705                 710 atg agt ata gcc agc att cta aca aat aca gta gaa gaa ctt gaa gaa          2453
Met Ser Ile Ala Ser Ile Leu Thr Asn Thr Val Glu Glu Leu Glu Glu
715                 720                 725 tcc agg cag aaa tgc cca ccc tgt tgg tat aaa ttt tcc aac ata ttc          2501
Ser Arg Gln Lys Cys Pro Pro Cys Trp Tyr Lys Phe Ser Asn Ile Phe
730                 735                 740                 745 tta atc tgg gac tgt tct cca tat tgg tta aaa gtg aaa cat gtt gtc          2549
Leu Ile Trp Asp Cys Ser Pro Tyr Trp Leu Lys Val Lys His Val Val
            750                 755                 760 aac ctg gtt gtg atg gac cca ttt gtt gac ctg gcc atc acc atc tgt          2597
Asn Leu Val Val Met Asp Pro Phe Val Asp Leu Ala Ile Thr Ile Cys
        765                 770                 775 att gtc tta aat act ctt ttc atg gcc atg gag cac tat cca atg acg          2645
Ile Val Leu Asn Thr Leu Phe Met Ala Met Glu His Tyr Pro Met Thr
    780                 785                 790 gac cat ttc aat aat gtg ctt aca gta gga aac ttg gtt ttc act ggg          2693
Asp His Phe Asn Asn Val Leu Thr Val Gly Asn Leu Val Phe Thr Gly
795                 800                 805 atc ttt aca gca gaa atg ttt ctg aaa att att gcc atg gat cct tac          2741
Ile Phe Thr Ala Glu Met Phe Leu Lys Ile Ile Ala Met Asp Pro Tyr
810                 815                 820                 825 tat tat ttc caa gaa ggc tgg aat atc ttt gac ggt ttt att gtg acg          2789
Tyr Tyr Phe Gln Glu Gly Trp Asn Ile Phe Asp Gly Phe Ile Val Thr
            830                 835                 840 ctt agc ctg gta gaa ctt gga ctc gcc aat gtg gaa gga tta tct gtt          2837
Leu Ser Leu Val Glu Leu Gly Leu Ala Asn Val Glu Gly Leu Ser Val
        845                 850                 855 ctc cgt tca ttt cga ttg ctg cga gtt ttc aag ttg gca aaa tct tgg          2885
Leu Arg Ser Phe Arg Leu Leu Arg Val Phe Lys Leu Ala Lys Ser Trp
    860                 865                 870 cca acg tta aat atg cta ata aag atc atc ggc aat tcc gtg ggg gct          2933
Pro Thr Leu Asn Met Leu Ile Lys Ile Ile Gly Asn Ser Val Gly Ala
875                 880                 885 ctg gga aat tta acc ctc gtc ttg gcc atc atc gtc ttc att ttt gcc          2981
Leu Gly Asn Leu Thr Leu Val Leu Ala Ile Ile Val Phe Ile Phe Ala
890                 895                 900                 905
```

```
gtg gtc ggc atg cag ctc ttt ggt aaa agc tac aaa gat tgt gtc tgc      3029
Val Val Gly Met Gln Leu Phe Gly Lys Ser Tyr Lys Asp Cys Val Cys
            910             915             920 aag atc gcc agt gat tgt caa ctc cca cgc tgg cac atg aat gac ttc      3077
Lys Ile Ala Ser Asp Cys Gln Leu Pro Arg Trp His Met Asn Asp Phe
        925             930             935 ttc cac tcc ttc ctg att gtg ttc cgc gtg ctg tgt ggg gag tgg ata      3125
Phe His Ser Phe Leu Ile Val Phe Arg Val Leu Cys Gly Glu Trp Ile
        940             945             950 gag acc atg tgg gac tgt atg gag gtt gct ggt caa gcc atg tgc ctt      3173
Glu Thr Met Trp Asp Cys Met Glu Val Ala Gly Gln Ala Met Cys Leu
        955             960             965 act gtc ttc atg atg gtc atg gtg att gga aac cta gtg gtc ctg aat      3221
Thr Val Phe Met Met Val Met Val Ile Gly Asn Leu Val Val Leu Asn
970             975             980             985 ctc ttt ctg gcc ttg ctt ctg agc tca ttt agt gca gac aac ctt  gca     3269
Leu Phe Leu Ala Leu Leu Leu Ser Ser Phe Ser Ala Asp Asn Leu  Ala
            990             995             1000 gcc act gat gat  gat aat gaa atg aat  aat ctc caa att gct  gtg       3314
Ala Thr Asp Asp  Asp Asn Glu Met Asn  Asn Leu Gln Ile Ala  Val
            1005            1010            1015 gat agg atg cac  aaa gga gta gct tat  gtg aaa aga aaa ata  tat       3359
Asp Arg Met His  Lys Gly Val Ala Tyr  Val Lys Arg Lys Ile  Tyr
            1020            1025            1030 gaa ttt att caa  cag tcc ttc att agg  aaa caa aag att tta  gat       3404
Glu Phe Ile Gln  Gln Ser Phe Ile Arg  Lys Gln Lys Ile Leu  Asp
            1035            1040            1045 gaa att aaa cca  ctt gat gat cta aac  aac aag aaa gac agt  tgt       3449
Glu Ile Lys Pro  Leu Asp Asp Leu Asn  Asn Lys Lys Asp Ser  Cys
            1050            1055            1060 atg tcc aat cat  aca gca gaa att ggg  aaa gat ctt gac tat  ctt       3494
Met Ser Asn His  Thr Ala Glu Ile Gly  Lys Asp Leu Asp Tyr  Leu
            1065            1070            1075 aaa gat gta aat  gga act aca agt ggt  ata gga act ggc agc  agt       3539
Lys Asp Val Asn  Gly Thr Thr Ser Gly  Ile Gly Thr Gly Ser  Ser
            1080            1085            1090 gtt gaa aaa tac  att att gat gaa agt  gat tac atg tca ttc  ata       3584
Val Glu Lys Tyr  Ile Ile Asp Glu Ser  Asp Tyr Met Ser Phe  Ile
            1095            1100            1105 aac aac ccc agt  ctt act gtg act gta  cca att gct gta gga  gaa       3629
Asn Asn Pro Ser  Leu Thr Val Thr Val  Pro Ile Ala Val Gly  Glu
            1110            1115            1120 tct gac ttt gaa  aat tta aac acg gaa  gac ttt agt agt gaa  tcg       3674
Ser Asp Phe Glu  Asn Leu Asn Thr Glu  Asp Phe Ser Ser Glu  Ser
            1125            1130            1135 gat ctg gaa gaa  agc aaa gag aaa ctg  aat gaa agc agc agc  tca       3719
Asp Leu Glu Glu  Ser Lys Glu Lys Leu  Asn Glu Ser Ser Ser  Ser
            1140            1145            1150 tca gaa ggt agc  act gtg gac atc ggc  gca cct gta gaa gaa  cag       3764
Ser Glu Gly Ser  Thr Val Asp Ile Gly  Ala Pro Val Glu Glu  Gln
            1155            1160            1165 ccc gta gtg gaa  cct gaa gaa act ctt  gaa cca gaa gct tgt  ttc       3809
Pro Val Val Glu  Pro Glu Glu Thr Leu  Glu Pro Glu Ala Cys  Phe
            1170            1175            1180 act gaa ggc tgt  gta caa aga ttc aag  tgt tgt caa atc aat  gtg       3854
Thr Glu Gly Cys  Val Gln Arg Phe Lys  Cys Cys Gln Ile Asn  Val
            1185            1190            1195 gaa gaa ggc aga  gga aaa caa tgg tgg  aac ctg aga agg acg  tgt       3899
Glu Glu Gly Arg  Gly Lys Gln Trp Trp  Asn Leu Arg Arg Thr  Cys
            1200            1205            1210
```

```
ttc cga ata gtt gaa cat aac tgg ttt gag acc ttc att gtt ttc    3944
Phe Arg Ile Val Glu His Asn Trp Phe Glu Thr Phe Ile Val Phe
        1215            1220            1225 atg att ctc ctt agt agt ggt gct ctg gca ttt gaa gat ata tat    3989
Met Ile Leu Leu Ser Ser Gly Ala Leu Ala Phe Glu Asp Ile Tyr
        1230            1235            1240 att gat cag cga aag acg att aag acg atg ttg gaa tat gct gac    4034
Ile Asp Gln Arg Lys Thr Ile Lys Thr Met Leu Glu Tyr Ala Asp
        1245            1250            1255 aag gtt ttc act tac att ttc att ctg gaa atg ctt cta aaa tgg    4079
Lys Val Phe Thr Tyr Ile Phe Ile Leu Glu Met Leu Leu Lys Trp
        1260            1265            1270 gtg gca tat ggc tat caa aca tat ttc acc aat gcc tgg tgt tgg    4124
Val Ala Tyr Gly Tyr Gln Thr Tyr Phe Thr Asn Ala Trp Cys Trp
        1275            1280            1285 ctg gac ttc tta att gtt gat gtt tca ttg gtc agt tta aca gca    4169
Leu Asp Phe Leu Ile Val Asp Val Ser Leu Val Ser Leu Thr Ala
        1290            1295            1300 aat gcc ttg ggt tac tca gaa ctt gga gcc atc aaa tct ctc agg    4214
Asn Ala Leu Gly Tyr Ser Glu Leu Gly Ala Ile Lys Ser Leu Arg
        1305            1310            1315 aca cta aga gct ctg aga cct cta aga gcc tta tct cga ttt gaa    4259
Thr Leu Arg Ala Leu Arg Pro Leu Arg Ala Leu Ser Arg Phe Glu
        1320            1325            1330 ggg atg agg gtg gtt gtg aat gcc ctt tta gga gca att cca tcc    4304
Gly Met Arg Val Val Val Asn Ala Leu Leu Gly Ala Ile Pro Ser
        1335            1340            1345 atc atg aat gtg ctt ctg gtt tgt ctt ata ttc tgg cta att ttc    4349
Ile Met Asn Val Leu Leu Val Cys Leu Ile Phe Trp Leu Ile Phe
        1350            1355            1360 agc atc atg ggc gta aat ttg ttt gct ggc aaa ttc tac cac tgt    4394
Ser Ile Met Gly Val Asn Leu Phe Ala Gly Lys Phe Tyr His Cys
        1365            1370            1375 att aac acc aca act ggt gac agg ttt gac atc gaa gac gtg aat    4439
Ile Asn Thr Thr Thr Gly Asp Arg Phe Asp Ile Glu Asp Val Asn
        1380            1385            1390 aat cat act gat tgc cta aaa cta ata gaa aga aat gag act gct    4484
Asn His Thr Asp Cys Leu Lys Leu Ile Glu Arg Asn Glu Thr Ala
        1395            1400            1405 cga tgg aaa aat gtg aaa gta aac ttt gat aat gta gga ttt ggg    4529
Arg Trp Lys Asn Val Lys Val Asn Phe Asp Asn Val Gly Phe Gly
        1410            1415            1420 tat ctc tct ttg ctt caa gtt gcc aca ttc aaa gga tgg atg gat    4574
Tyr Leu Ser Leu Leu Gln Val Ala Thr Phe Lys Gly Trp Met Asp
        1425            1430            1435 ata atg tat gca gca gtt gat tcc aga aat gtg gaa ctc cag cct    4619
Ile Met Tyr Ala Ala Val Asp Ser Arg Asn Val Glu Leu Gln Pro
        1440            1445            1450 aag tat gaa aaa agt ctg tac atg tat ctt tac ttt gtt att ttc    4664
Lys Tyr Glu Lys Ser Leu Tyr Met Tyr Leu Tyr Phe Val Ile Phe
        1455            1460            1465 atc atc ttt ggg tcc ttc ttc acc ttg aac ctg ttt att ggt gtc    4709
Ile Ile Phe Gly Ser Phe Phe Thr Leu Asn Leu Phe Ile Gly Val
        1470            1475            1480 atc ata gat aat ttc aac cag cag aaa aag aag ttt gga ggt caa    4754
Ile Ile Asp Asn Phe Asn Gln Gln Lys Lys Lys Phe Gly Gly Gln
        1485            1490            1495 gac atc ttt atg aca gaa gaa cag aag aaa tac tat aat gca atg    4799
Asp Ile Phe Met Thr Glu Glu Gln Lys Lys Tyr Tyr Asn Ala Met
        1500            1505            1510
```

| | | | | | | | | | | | | | | |
|---|---|---|---|---|---|---|---|---|---|---|---|---|---|---|
| aaa | aaa | tta | gga | tcg | aaa | aaa | ccg | caa | aag | cct | ata | cct | cga | cca | 4844 |
| Lys | Lys | Leu | Gly | Ser | Lys | Lys | Pro | Gln | Lys | Pro | Ile | Pro | Arg | Pro | |
| | | | 1515 | | | | 1520 | | | | 1525 | | | | |
| gga | aac | aaa | ttt | caa | gga | atg | gtc | ttt | gac | ttc | gta | acc | aga | caa | 4889 |
| Gly | Asn | Lys | Phe | Gln | Gly | Met | Val | Phe | Asp | Phe | Val | Thr | Arg | Gln | |
| | | | 1530 | | | | 1535 | | | | 1540 | | | | |
| gtt | ttt | gac | ata | agc | atc | atg | att | ctc | atc | tgt | ctt | aac | atg | gtc | 4934 |
| Val | Phe | Asp | Ile | Ser | Ile | Met | Ile | Leu | Ile | Cys | Leu | Asn | Met | Val | |
| | | | 1545 | | | | 1550 | | | | 1555 | | | | |
| aca | atg | atg | gtg | gaa | aca | gat | gac | cag | agt | gaa | tat | gtg | act | acc | 4979 |
| Thr | Met | Met | Val | Glu | Thr | Asp | Asp | Gln | Ser | Glu | Tyr | Val | Thr | Thr | |
| | | | 1560 | | | | 1565 | | | | 1570 | | | | |
| att | ttg | tca | cgc | atc | aat | ctg | gtg | ttc | att | gtg | cta | ttt | act | gga | 5024 |
| Ile | Leu | Ser | Arg | Ile | Asn | Leu | Val | Phe | Ile | Val | Leu | Phe | Thr | Gly | |
| | | | 1575 | | | | 1580 | | | | 1585 | | | | |
| gag | tgt | gta | ctg | aaa | ctc | atc | tct | cta | cgc | cat | tat | tat | ttt | acc | 5069 |
| Glu | Cys | Val | Leu | Lys | Leu | Ile | Ser | Leu | Arg | His | Tyr | Tyr | Phe | Thr | |
| | | | 1590 | | | | 1595 | | | | 1600 | | | | |
| att | gga | tgg | aat | att | ttt | gat | ttt | gtg | gtt | gtc | att | ctc | tcc | att | 5114 |
| Ile | Gly | Trp | Asn | Ile | Phe | Asp | Phe | Val | Val | Val | Ile | Leu | Ser | Ile | |
| | | | 1605 | | | | 1610 | | | | 1615 | | | | |
| gta | ggt | atg | ttt | ctt | gcc | gag | ctg | ata | gaa | aag | tat | ttc | gtg | tcc | 5159 |
| Val | Gly | Met | Phe | Leu | Ala | Glu | Leu | Ile | Glu | Lys | Tyr | Phe | Val | Ser | |
| | | | 1620 | | | | 1625 | | | | 1630 | | | | |
| cct | acc | ctg | ttc | cga | gtg | atc | cgt | ctt | gct | agg | att | ggc | cga | atc | 5204 |
| Pro | Thr | Leu | Phe | Arg | Val | Ile | Arg | Leu | Ala | Arg | Ile | Gly | Arg | Ile | |
| | | | 1635 | | | | 1640 | | | | 1645 | | | | |
| cta | cgt | ctg | atc | aaa | gga | gca | aag | ggg | atc | cgc | acg | ctg | ctc | ttt | 5249 |
| Leu | Arg | Leu | Ile | Lys | Gly | Ala | Lys | Gly | Ile | Arg | Thr | Leu | Leu | Phe | |
| | | | 1650 | | | | 1655 | | | | 1660 | | | | |
| gct | ttg | atg | atg | tcc | ctt | cct | gcg | ttg | ttt | aac | atc | ggc | ctc | cta | 5294 |
| Ala | Leu | Met | Met | Ser | Leu | Pro | Ala | Leu | Phe | Asn | Ile | Gly | Leu | Leu | |
| | | | 1665 | | | | 1670 | | | | 1675 | | | | |
| ctc | ttc | cta | gtc | atg | ttc | atc | tac | gcc | atc | ttt | ggg | atg | tcc | aac | 5339 |
| Leu | Phe | Leu | Val | Met | Phe | Ile | Tyr | Ala | Ile | Phe | Gly | Met | Ser | Asn | |
| | | | 1680 | | | | 1685 | | | | 1690 | | | | |
| ttt | gcc | tat | gtt | aag | agg | gaa | gtt | ggg | atc | gat | gac | atg | ttc | aac | 5384 |
| Phe | Ala | Tyr | Val | Lys | Arg | Glu | Val | Gly | Ile | Asp | Asp | Met | Phe | Asn | |
| | | | 1695 | | | | 1700 | | | | 1705 | | | | |
| ttt | gag | acc | ttt | ggc | aac | agc | atg | atc | tgc | cta | ttc | caa | att | aca | 5429 |
| Phe | Glu | Thr | Phe | Gly | Asn | Ser | Met | Ile | Cys | Leu | Phe | Gln | Ile | Thr | |
| | | | 1710 | | | | 1715 | | | | 1720 | | | | |
| acc | tct | gct | ggc | tgg | gat | gga | ttg | cta | gca | ccc | att | ctc | aac | agt | 5474 |
| Thr | Ser | Ala | Gly | Trp | Asp | Gly | Leu | Leu | Ala | Pro | Ile | Leu | Asn | Ser | |
| | | | 1725 | | | | 1730 | | | | 1735 | | | | |
| aag | cca | ccc | gac | tgt | gac | cct | aat | aaa | gtt | aac | cct | gga | agc | tca | 5519 |
| Lys | Pro | Pro | Asp | Cys | Asp | Pro | Asn | Lys | Val | Asn | Pro | Gly | Ser | Ser | |
| | | | 1740 | | | | 1745 | | | | 1750 | | | | |
| gtt | aag | gga | gac | tgt | ggg | aac | cca | tct | gtt | gga | att | ttc | ttt | ttt | 5564 |
| Val | Lys | Gly | Asp | Cys | Gly | Asn | Pro | Ser | Val | Gly | Ile | Phe | Phe | Phe | |
| | | | 1755 | | | | 1760 | | | | 1765 | | | | |
| gtc | agt | tac | atc | atc | ata | tcc | ttc | ctg | gtt | gtg | gtg | aac | atg | tac | 5609 |
| Val | Ser | Tyr | Ile | Ile | Ile | Ser | Phe | Leu | Val | Val | Val | Asn | Met | Tyr | |
| | | | 1770 | | | | 1775 | | | | 1780 | | | | |
| atc | gcg | gtc | atc | ctg | gag | aac | ttc | agt | gtt | gct | act | gaa | gaa | agt | 5654 |
| Ile | Ala | Val | Ile | Leu | Glu | Asn | Phe | Ser | Val | Ala | Thr | Glu | Glu | Ser | |
| | | | 1785 | | | | 1790 | | | | 1795 | | | | |
| gca | gag | cct | ctg | agt | gag | gat | gac | ttt | gag | atg | ttc | tat | gag | gtt | 5699 |
| Ala | Glu | Pro | Leu | Ser | Glu | Asp | Asp | Phe | Glu | Met | Phe | Tyr | Glu | Val | |
| | | | 1800 | | | | 1805 | | | | 1810 | | | | |

| | | |
|---|---|---|
| tgg gag aag ttt gat ccc gat gca act cag ttc atg gaa ttt gaa<br>Trp Glu Lys Phe Asp Pro Asp Ala Thr Gln Phe Met Glu Phe Glu<br>1815                        1820                      1825 | | 5744 |
| aaa tta tct cag ttt gca gct gcg ctt gaa ccg cct ctc aat ctg<br>Lys Leu Ser Gln Phe Ala Ala Ala Leu Glu Pro Pro Leu Asn Leu<br>1830                        1835                      1840 | | 5789 |
| cca caa cca aac aaa ctc cag ctc att gcc atg gat ttg ccc atg<br>Pro Gln Pro Asn Lys Leu Gln Leu Ile Ala Met Asp Leu Pro Met<br>1845                        1850                      1855 | | 5834 |
| gtg agt ggt gac cgg atc cac tgt ctt gat atc tta ttt gct ttt<br>Val Ser Gly Asp Arg Ile His Cys Leu Asp Ile Leu Phe Ala Phe<br>1860                        1865                      1870 | | 5879 |
| aca aag cgg gtt cta gga gag agt gga gag atg gat gct cta cga<br>Thr Lys Arg Val Leu Gly Glu Ser Gly Glu Met Asp Ala Leu Arg<br>1875                        1880                      1885 | | 5924 |
| ata cag atg gaa gag cga ttc atg gct tcc aat cct tcc aag gtc<br>Ile Gln Met Glu Glu Arg Phe Met Ala Ser Asn Pro Ser Lys Val<br>1890                        1895                      1900 | | 5969 |
| tcc tat cag cca atc act act act tta aaa cga aaa caa gag gaa<br>Ser Tyr Gln Pro Ile Thr Thr Thr Leu Lys Arg Lys Gln Glu Glu<br>1905                        1910                      1915 | | 6014 |
| gta tct gct gtc att att cag cgt gct tac aga cgc cac ctt tta<br>Val Ser Ala Val Ile Ile Gln Arg Ala Tyr Arg Arg His Leu Leu<br>1920                        1925                      1930 | | 6059 |
| aag cga act gta aaa caa gct tcc ttt acg tac aat aaa aac aaa<br>Lys Arg Thr Val Lys Gln Ala Ser Phe Thr Tyr Asn Lys Asn Lys<br>1935                        1940                      1945 | | 6104 |
| atc aaa ggt ggg gct aat ctt ctt ata aaa gaa gac atg ata att<br>Ile Lys Gly Gly Ala Asn Leu Leu Ile Lys Glu Asp Met Ile Ile<br>1950                        1955                      1960 | | 6149 |
| gac aga ata aat gaa aac tct att aca gaa aaa act gat ctg acc<br>Asp Arg Ile Asn Glu Asn Ser Ile Thr Glu Lys Thr Asp Leu Thr<br>1965                        1970                      1975 | | 6194 |
| atg tcc act gca gct tgt cca cct tcc tat gac cgg gtg aca aag<br>Met Ser Thr Ala Ala Cys Pro Pro Ser Tyr Asp Arg Val Thr Lys<br>1980                        1985                      1990 | | 6239 |
| cca att gtg gaa aaa cat gag caa gaa ggc aaa gat gaa aaa gcc<br>Pro Ile Val Glu Lys His Glu Gln Glu Gly Lys Asp Glu Lys Ala<br>1995                        2000                      2005 | | 6284 |
| aaa ggg aaa taa atgaaaataa ataaaaataa ttgggtgaca aattgtttac<br>Lys Gly Lys | | 6336 |
| agcctgtgaa ggtgatgtat ttttatcaac aggactcctt taggaggtca atgccaaact | | 6396 |
| gactgttttt acacaaatct ccttaaggtc agtgcctaca ataagacagt gaccccttgt | | 6456 |
| cagcaaactg tgactctgtg taaaggggag atgaccttga caggaggtta ctgttctcac | | 6516 |
| taccagctga cactgctgaa gataagatgc acaatggcta gtcagactgt agggaccagt | | 6576 |
| ttcaaggggt gcaaacctgt gattttgggg ttgtttaaca tgaaacactt tagtgtagta | | 6636 |
| attgtatcca ctgtttgcat ttcaactgcc acatttgtca cattttatg gaatctgtta | | 6696 |
| gtggattcat cttttttgtta atccatgtgt ttattatatg tgactatttt tgtaaacgaa | | 6756 |
| gtttctgttg agaaataggc taaggacctc tataacaggt atgccacctg ggggtatgg | | 6816 |
| caaccacatg gccctcccag ctacacaaag tcgtggtttg catgagggca tgctgcactt | | 6876 |
| agagatcatg catgagaaaa agtcacaaga aaaacaaatt cttaaatttc accatatttc | | 6936 |
| tgggagggggt aattgggtga taagtggagg tgctttgttg atcttgtttt gcgaaatcca | | 6996 |
| gcccctagac caagtagatt atttgtgggt aggccagtaa atcttagcag gtgcaaactt | | 7056 |

-continued

```
cattcaaatg tttggagtca taaatgttat gtttcttttt gttgtattaa aaaaaaaacc    7116
tgaatagtga atattgcccc tcaccctcca ccgccagaag actgaattga ccaaaattac    7176
tctttataaa tttctgcttt ttcctgcact ttgtttagcc atctttgggc tctcagcaag    7236
gttgacactg tatatgttaa tgaaatgcta tttattatgt aaatagtcat tttaccctgt    7296
ggtgcacgtt tgagcaaaca ataatgacc taagcacagt atttattgca tcaaatatgt     7356
accacaagaa atgtagagtg caagctttac acaggtaata aaatgtattc tgtaccattt    7416
atagatagtt tggatgctat caatgcatgt ttatattacc atgctgctgt atctggtttc    7476
tctcactgct cagaatctca tttatgagaa accatatgtc agtggtaaag tcaaggaaat    7536
tgttcaacag atctcattta tttaagtcat taagcaatag tttgcagcac tttaacagct    7596
ttttggttat tttacatttt taagtggata acatatggta tatagccaga ctgtacagac    7656
atgtttaaaa aaacacactg cttaacctat taaatatgtg tttagaattt tataagcaaa    7716
tataaatact gtaaaagtc actttatttt atttttcagc attatgtaca taaatatgaa     7776
gaggaaatta tcttcaggtt gatatcacaa tcacttttct tactttctgt ccatagtact    7836
ttttcatgaa agaaatttgc taaataagac atgaaaacaa gactgggtag ttgtagattt    7896 ctgctttta aattacattt gctaatttta gattatttca caattttaag gagcaaaata     7956
ggttcacgat tcatatccaa attatgcttt gcaattggaa aagggtttaa aatttttattt   8016 atatttctgg tagtacctgt actaactgaa ttgaaggtag tgcttatgtt attttttgttc   8076 tttttttctg acttcggttt atgttttcat ttctttggag taatgctgct ctagattgtt    8136
ctaaatagaa tgtgggcttc ataatttttt tttccacaaa aacagagtag tcaacttata    8196
tagtcaatta catcaggaca ttttgtgttt cttacagaag caaaccatag gctcctcttt    8256
tccttaaaac tacttagata aactgtattc gtgaactgca tgctggaaaa tgctactatt    8316
atgctaaata atgctaacca acatttaaaa tgtgcaaaac taataaagat tacattttt    8376 attt                                                                 8381
```

<210> SEQ ID NO 10
<211> LENGTH: 2009
<212> TYPE: PRT
<213> ORGANISM: Homo sapiens

<400> SEQUENCE: 10

```
Met Glu Gln Thr Val Leu Val Pro Pro Gly Pro Asp Ser Phe Asn Phe
  1               5                  10                  15

Phe Thr Arg Glu Ser Leu Ala Ala Ile Glu Arg Arg Ile Ala Glu Glu
                 20                  25                  30

Lys Ala Lys Asn Pro Lys Pro Asp Lys Lys Asp Asp Asp Glu Asn Gly
             35                  40                  45

Pro Lys Pro Asn Ser Asp Leu Glu Ala Gly Lys Asn Leu Pro Phe Ile
         50                  55                  60

Tyr Gly Asp Ile Pro Pro Glu Met Val Ser Glu Pro Leu Glu Asp Leu
 65                  70                  75                  80

Asp Pro Tyr Tyr Ile Asn Lys Lys Thr Phe Ile Val Leu Asn Lys Leu
                 85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125
```

-continued

```
Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ala Arg
                165                 170                 175

Gly Phe Cys Leu Glu Asp Phe Thr Phe Leu Arg Asp Pro Trp Asn Trp
                180                 185                 190

Leu Asp Phe Thr Val Ile Thr Phe Ala Tyr Val Thr Glu Phe Val Asp
            195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
    275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
                355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
    435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
                500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
    530                 535                 540
```

```
Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asn Gly Thr Thr Thr Glu Thr Glu
            675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
            930                 935                 940

Phe Arg Val Leu Cys Gly Glu Trp Ile Glu Thr Met Trp Asp Cys Met
945                 950                 955                 960
```

```
Glu Val Ala Gly Gln Ala Met Cys Leu Thr Val Phe Met Met Val Met
                965                 970                 975
Val Ile Gly Asn Leu Val Val Leu Asn Leu Phe Leu Ala Leu Leu Leu
                980                 985                 990
Ser Ser Phe Ser Ala Asp Asn Leu Ala Ala Thr Asp Asp Asn Glu
            995                1000                1005
Met Asn Asn Leu Gln Ile Ala Val Asp Arg Met His Lys Gly Val
    1010                1015                1020
Ala Tyr Val Lys Arg Lys Ile Tyr Glu Phe Ile Gln Gln Ser Phe
    1025                1030                1035
Ile Arg Lys Gln Lys Ile Leu Asp Glu Ile Lys Pro Leu Asp Asp
    1040                1045                1050
Leu Asn Asn Lys Lys Asp Ser Cys Met Ser Asn His Thr Ala Glu
    1055                1060                1065
Ile Gly Lys Asp Leu Asp Tyr Leu Lys Asp Val Asn Gly Thr Thr
    1070                1075                1080
Ser Gly Ile Gly Thr Gly Ser Ser Val Glu Lys Tyr Ile Ile Asp
    1085                1090                1095
Glu Ser Asp Tyr Met Ser Phe Ile Asn Asn Pro Ser Leu Thr Val
    1100                1105                1110
Thr Val Pro Ile Ala Val Gly Glu Ser Asp Phe Glu Asn Leu Asn
    1115                1120                1125
Thr Glu Asp Phe Ser Ser Glu Ser Asp Leu Glu Glu Ser Lys Glu
    1130                1135                1140
Lys Leu Asn Glu Ser Ser Ser Ser Glu Gly Ser Thr Val Asp
    1145                1150                1155
Ile Gly Ala Pro Val Glu Glu Gln Pro Val Val Glu Pro Glu Glu
    1160                1165                1170
Thr Leu Glu Pro Glu Ala Cys Phe Thr Glu Gly Cys Val Gln Arg
    1175                1180                1185
Phe Lys Cys Cys Gln Ile Asn Val Glu Glu Gly Arg Gly Lys Gln
    1190                1195                1200
Trp Trp Asn Leu Arg Arg Thr Cys Phe Arg Ile Val Glu His Asn
    1205                1210                1215
Trp Phe Glu Thr Phe Ile Val Phe Met Ile Leu Leu Ser Ser Gly
    1220                1225                1230
Ala Leu Ala Phe Glu Asp Ile Tyr Ile Asp Gln Arg Lys Thr Ile
    1235                1240                1245
Lys Thr Met Leu Glu Tyr Ala Asp Lys Val Phe Thr Tyr Ile Phe
    1250                1255                1260
Ile Leu Glu Met Leu Leu Lys Trp Val Ala Tyr Gly Tyr Gln Thr
    1265                1270                1275
Tyr Phe Thr Asn Ala Trp Cys Trp Leu Asp Phe Leu Ile Val Asp
    1280                1285                1290
Val Ser Leu Val Ser Leu Thr Ala Asn Ala Leu Gly Tyr Ser Glu
    1295                1300                1305
Leu Gly Ala Ile Lys Ser Leu Arg Thr Leu Arg Ala Leu Arg Pro
    1310                1315                1320
Leu Arg Ala Leu Ser Arg Phe Glu Gly Met Arg Val Val Val Asn
    1325                1330                1335
Ala Leu Leu Gly Ala Ile Pro Ser Ile Met Asn Val Leu Leu Val
    1340                1345                1350
```

```
Cys Leu Ile Phe Trp Leu Ile Phe Ser Ile Met Gly Val Asn Leu
    1355            1360            1365

Phe Ala Gly Lys Phe Tyr His Cys Ile Asn Thr Thr Thr Gly Asp
    1370            1375            1380

Arg Phe Asp Ile Glu Asp Val Asn Asn His Thr Asp Cys Leu Lys
    1385            1390            1395

Leu Ile Glu Arg Asn Glu Thr Ala Arg Trp Lys Asn Val Lys Val
    1400            1405            1410

Asn Phe Asp Asn Val Gly Phe Gly Tyr Leu Ser Leu Leu Gln Val
    1415            1420            1425

Ala Thr Phe Lys Gly Trp Met Asp Ile Met Tyr Ala Ala Val Asp
    1430            1435            1440

Ser Arg Asn Val Glu Leu Gln Pro Lys Tyr Glu Lys Ser Leu Tyr
    1445            1450            1455

Met Tyr Leu Tyr Phe Val Ile Phe Ile Ile Phe Gly Ser Phe Phe
    1460            1465            1470

Thr Leu Asn Leu Phe Ile Gly Val Ile Ile Asp Asn Phe Asn Gln
    1475            1480            1485

Gln Lys Lys Lys Phe Gly Gly Gln Asp Ile Phe Met Thr Glu Glu
    1490            1495            1500

Gln Lys Lys Tyr Tyr Asn Ala Met Lys Lys Leu Gly Ser Lys Lys
    1505            1510            1515

Pro Gln Lys Pro Ile Pro Arg Pro Gly Asn Lys Phe Gln Gly Met
    1520            1525            1530

Val Phe Asp Phe Val Thr Arg Gln Val Phe Asp Ile Ser Ile Met
    1535            1540            1545

Ile Leu Ile Cys Leu Asn Met Val Thr Met Met Val Glu Thr Asp
    1550            1555            1560

Asp Gln Ser Glu Tyr Val Thr Thr Ile Leu Ser Arg Ile Asn Leu
    1565            1570            1575

Val Phe Ile Val Leu Phe Thr Gly Glu Cys Val Leu Lys Leu Ile
    1580            1585            1590

Ser Leu Arg His Tyr Tyr Phe Thr Ile Gly Trp Asn Ile Phe Asp
    1595            1600            1605

Phe Val Val Val Ile Leu Ser Ile Val Gly Met Phe Leu Ala Glu
    1610            1615            1620

Leu Ile Glu Lys Tyr Phe Val Ser Pro Thr Leu Phe Arg Val Ile
    1625            1630            1635

Arg Leu Ala Arg Ile Gly Arg Ile Leu Arg Leu Ile Lys Gly Ala
    1640            1645            1650

Lys Gly Ile Arg Thr Leu Leu Phe Ala Leu Met Met Ser Leu Pro
    1655            1660            1665

Ala Leu Phe Asn Ile Gly Leu Leu Leu Phe Leu Val Met Phe Ile
    1670            1675            1680

Tyr Ala Ile Phe Gly Met Ser Asn Phe Ala Tyr Val Lys Arg Glu
    1685            1690            1695

Val Gly Ile Asp Asp Met Phe Asn Phe Glu Thr Phe Gly Asn Ser
    1700            1705            1710

Met Ile Cys Leu Phe Gln Ile Thr Thr Ser Ala Gly Trp Asp Gly
    1715            1720            1725

Leu Leu Ala Pro Ile Leu Asn Ser Lys Pro Pro Asp Cys Asp Pro
    1730            1735            1740
```

-continued

| | | | | | | | | | |
|---|---|---|---|---|---|---|---|---|---|
| Asn | Lys | Val | Asn | Pro | Gly | Ser | Ser | Val | Lys | Gly | Asp | Cys | Gly | Asn |
| | 1745 | | | | 1750 | | | | 1755 | |

```
Asn Lys Val Asn Pro Gly Ser  Ser Val Lys Gly Asp  Cys Gly Asn
    1745              1750              1755

Pro Ser Val Gly Ile Phe Phe  Val Ser Tyr Ile  Ile Ile Ser
    1760             1765              1770

Phe Leu Val Val Val Asn Met  Tyr Ile Ala Val  Ile Leu Glu Asn
    1775             1780              1785

Phe Ser Val Ala Thr Glu Glu  Ser Ala Glu Pro Leu  Ser Glu Asp
    1790             1795              1800

Asp Phe Glu Met Phe Tyr Glu  Val Trp Glu Lys Phe  Asp Pro Asp
    1805             1810              1815

Ala Thr Gln Phe Met Glu Phe  Glu Lys Leu Ser Gln  Phe Ala Ala
    1820             1825              1830

Ala Leu Glu Pro Pro Leu Asn  Leu Pro Gln Pro Asn  Lys Leu Gln
    1835             1840              1845

Leu Ile Ala Met Asp Leu Pro  Met Val Ser Gly Asp  Arg Ile His
    1850             1855              1860

Cys Leu Asp Ile Leu Phe Ala  Phe Thr Lys Arg Val  Leu Gly Glu
    1865             1870              1875

Ser Gly Glu Met Asp Ala Leu  Arg Ile Gln Met Glu  Glu Arg Phe
    1880             1885              1890

Met Ala Ser Asn Pro Ser Lys  Val Ser Tyr Gln Pro  Ile Thr Thr
    1895             1900              1905

Thr Leu Lys Arg Lys Gln Glu  Glu Val Ser Ala Val  Ile Ile Gln
    1910             1915              1920

Arg Ala Tyr Arg Arg His Leu  Leu Lys Arg Thr Val  Lys Gln Ala
    1925             1930              1935

Ser Phe Thr Tyr Asn Lys Asn  Lys Ile Lys Gly Gly  Ala Asn Leu
    1940             1945              1950

Leu Ile Lys Glu Asp Met Ile  Ile Asp Arg Ile Asn  Glu Asn Ser
    1955             1960              1965

Ile Thr Glu Lys Thr Asp Leu  Thr Met Ser Thr Ala  Ala Cys Pro
    1970             1975              1980

Pro Ser Tyr Asp Arg Val Thr  Lys Pro Ile Val Glu  Lys His Glu
    1985             1990              1995

Gln Glu Gly Lys Asp Glu Lys  Ala Lys Gly Lys
    2000             2005
```

```
<210> SEQ ID NO 11
<211> LENGTH: 8381
<212> TYPE: DNA
<213> ORGANISM: Homo sapiens
<220> FEATURE:
<221> NAME/KEY: CDS
<222> LOCATION: (267)..(6296)

<400> SEQUENCE: 11
atactgcaga ggtctctggt gcatgtgtgt atgtgtgcgt ttgtgtgtgt ttgtgtgtct    60
gtgtgttctg ccccagtgag actgcagccc ttgtaaatac tttgacacct tttgcaagaa   120
ggaatctgaa caattgcaac tgaaggcaca ttgttatcat ctcgtctttg ggtgatgctg   180
ttcctcactg cagatggata attttccttt taatcaggaa tttcatatgc agaataaatg   240
gtaattaaaa tgtgcaggat gacaag atg gag caa aca gtg ctt gta cca cca   293
                              Met Glu Gln Thr Val Leu Val Pro Pro
                                1               5
```

-continued

| | | |
|---|---|---|
| gga cct gac agc ttc aac ttc ttc acc aga gaa tct ctt gcg gct att<br>Gly Pro Asp Ser Phe Asn Phe Phe Thr Arg Glu Ser Leu Ala Ala Ile<br>10                        15                  20                      25 | 341 |
| gaa aga cgc att gca gaa gaa aag gca aag aat ccc aaa cca gac aaa<br>Glu Arg Arg Ile Ala Glu Glu Lys Ala Lys Asn Pro Lys Pro Asp Lys<br>                  30                  35                  40 | 389 |
| aaa gat gac gac gaa aat ggc cca aag cca aat agt gac ttg gaa gct<br>Lys Asp Asp Asp Glu Asn Gly Pro Lys Pro Asn Ser Asp Leu Glu Ala<br>              45                  50                  55 | 437 |
| gga aag aac ctt cca ttt att tat gga gac att cct cca gag atg gtg<br>Gly Lys Asn Leu Pro Phe Ile Tyr Gly Asp Ile Pro Pro Glu Met Val<br>        60                  65                  70 | 485 |
| tca gag ccc ctg gag gac ctg gac ccc tac tat atc aat aag aaa act<br>Ser Glu Pro Leu Glu Asp Leu Asp Pro Tyr Tyr Ile Asn Lys Lys Thr<br>75                        80                  85 | 533 |
| ttt ata gta ttg aat aaa ttg aag gcc atc ttc cgg ttc agt gcc acc<br>Phe Ile Val Leu Asn Lys Leu Lys Ala Ile Phe Arg Phe Ser Ala Thr<br>90                        95                 100             105 | 581 |
| tct gcc ctg tac att tta act ccc ttc aat cct ctt agg aaa ata gct<br>Ser Ala Leu Tyr Ile Leu Thr Pro Phe Asn Pro Leu Arg Lys Ile Ala<br>                  110               115              120 | 629 |
| att aag att ttg gta cat tca tta ttc agc atg cta att atg tgc act<br>Ile Lys Ile Leu Val His Ser Leu Phe Ser Met Leu Ile Met Cys Thr<br>                  125               130              135 | 677 |
| att ttg aca aac tgt gtg ttt atg aca atg agt aac cct cct gat tgg<br>Ile Leu Thr Asn Cys Val Phe Met Thr Met Ser Asn Pro Pro Asp Trp<br>140                      145               150 | 725 |
| aca aag aat gta gaa tac acc ttc aca gga ata tat act ttt gaa tca<br>Thr Lys Asn Val Glu Tyr Thr Phe Thr Gly Ile Tyr Thr Phe Glu Ser<br>155                     160               165 | 773 |
| ctt ata aaa att att gca agg gga ttc tgt tta gaa gat ttt act ttc<br>Leu Ile Lys Ile Ile Ala Arg Gly Phe Cys Leu Glu Asp Phe Thr Phe<br>170                     175               180              185 | 821 |
| ctt cgg gat cca tgg aac tgg ctc gat ttc act gtc att aca ttt gcg<br>Leu Arg Asp Pro Trp Asn Trp Leu Asp Phe Thr Val Ile Thr Phe Ala<br>                  190               195              200 | 869 |
| tac gtc aca gag ttt gtg gac ctg ggc aat gtc tcg gca ttg aga aca<br>Tyr Val Thr Glu Phe Val Asp Leu Gly Asn Val Ser Ala Leu Arg Thr<br>                  205               210              215 | 917 |
| ttc aga gtt ctc cga gca ttg aag acg att tca gtc att cca ggc ctg<br>Phe Arg Val Leu Arg Ala Leu Lys Thr Ile Ser Val Ile Pro Gly Leu<br>220                      225               230 | 965 |
| aaa acc att gtg gga gcc ctg atc cag tct gtg aag aag ctc tca gat<br>Lys Thr Ile Val Gly Ala Leu Ile Gln Ser Val Lys Lys Leu Ser Asp<br>235                     240               245 | 1013 |
| gta atg atc ctg act gtg ttc tgt ctg agc gta ttt gct cta att ggg<br>Val Met Ile Leu Thr Val Phe Cys Leu Ser Val Phe Ala Leu Ile Gly<br>250                      255               260              265 | 1061 |
| ctg cag ctg ttc atg ggc aac ctg agg aat aaa tgt ata caa tgg cct<br>Leu Gln Leu Phe Met Gly Asn Leu Arg Asn Lys Cys Ile Gln Trp Pro<br>                  270               275              280 | 1109 |
| ccc acc aat gct tcc ttg gag gaa cat agt ata gaa aag aat ata act<br>Pro Thr Asn Ala Ser Leu Glu Glu His Ser Ile Glu Lys Asn Ile Thr<br>                  285               290              295 | 1157 |
| gtg aat tat aat ggt aca ctt ata aat gaa act gtc ttt gag ttt gac<br>Val Asn Tyr Asn Gly Thr Leu Ile Asn Glu Thr Val Phe Glu Phe Asp<br>300                     305               310 | 1205 |
| tgg aag tca tat att caa gat tca aga tat cat tat ttc ctg gag ggt<br>Trp Lys Ser Tyr Ile Gln Asp Ser Arg Tyr His Tyr Phe Leu Glu Gly<br>315                     320               325 | 1253 |

-continued

| | |
|---|---|
| ttt tta gat gca cta cta tgt gga aat agc tct gat gca ggc caa tgt<br>Phe Leu Asp Ala Leu Leu Cys Gly Asn Ser Ser Asp Ala Gly Gln Cys<br>330                        335                        340                        345 | 1301 |
| cca gag gga tat atg tgt gtg aaa gct ggt aga aat ccc aat tat ggc<br>Pro Glu Gly Tyr Met Cys Val Lys Ala Gly Arg Asn Pro Asn Tyr Gly<br>                        350                        355                        360 | 1349 |
| tac aca agc ttt gat acc ttc agt tgg gct ttt ttg tcc ttg ttt cga<br>Tyr Thr Ser Phe Asp Thr Phe Ser Trp Ala Phe Leu Ser Leu Phe Arg<br>                365                        370                        375 | 1397 |
| cta atg act cag gac ttc tgg gaa aat ctt tat caa ctg aca tta cgt<br>Leu Met Thr Gln Asp Phe Trp Glu Asn Leu Tyr Gln Leu Thr Leu Arg<br>              380                        385                        390 | 1445 |
| gct gct ggg aaa acg tac atg ata ttt ttt gta ttg gtc att ttc ttg<br>Ala Ala Gly Lys Thr Tyr Met Ile Phe Phe Val Leu Val Ile Phe Leu<br>395                        400                        405 | 1493 |
| ggc tca ttc tac cta ata aat ttg atc ctg gct gtg gtg gcc atg gcc<br>Gly Ser Phe Tyr Leu Ile Asn Leu Ile Leu Ala Val Val Ala Met Ala<br>410                        415                        420                        425 | 1541 |
| tac gag gaa cag aat cag gcc acc ttg gaa gaa gca gaa cag aaa gag<br>Tyr Glu Glu Gln Asn Gln Ala Thr Leu Glu Glu Ala Glu Gln Lys Glu<br>                        430                        435                        440 | 1589 |
| gcc gaa ttt cag cag atg att gaa cag ctt aaa aag caa cag gag gca<br>Ala Glu Phe Gln Gln Met Ile Glu Gln Leu Lys Lys Gln Gln Glu Ala<br>                445                        450                        455 | 1637 |
| gct cag cag gca gca acg gca act gcc tca gaa cat tcc aga gag ccc<br>Ala Gln Gln Ala Ala Thr Ala Thr Ala Ser Glu His Ser Arg Glu Pro<br>              460                        465                        470 | 1685 |
| agt gca gca ggc agg ctc tca gac agc tca tct gaa gcc tct aag ttg<br>Ser Ala Ala Gly Arg Leu Ser Asp Ser Ser Ser Glu Ala Ser Lys Leu<br>475                        480                        485 | 1733 |
| agt tcc aag agt gct aag gaa aga aga aat cgg agg aag aaa aga aaa<br>Ser Ser Lys Ser Ala Lys Glu Arg Arg Asn Arg Arg Lys Lys Arg Lys<br>490                        495                        500                        505 | 1781 |
| cag aaa gag cag tct ggt ggg gaa gag aaa gat gag gat gaa ttc caa<br>Gln Lys Glu Gln Ser Gly Gly Glu Glu Lys Asp Glu Asp Glu Phe Gln<br>                        510                        515                        520 | 1829 |
| aaa tct gaa tct gag gac agc atc agg agg aaa ggt ttt cgc ttc tcc<br>Lys Ser Glu Ser Glu Asp Ser Ile Arg Arg Lys Gly Phe Arg Phe Ser<br>              525                        530                        535 | 1877 |
| att gaa ggg aac cga ttg aca tat gaa aag agg tac tcc tcc cca cac<br>Ile Glu Gly Asn Arg Leu Thr Tyr Glu Lys Arg Tyr Ser Ser Pro His<br>540                        545                        550 | 1925 |
| cag tct ttg ttg agc atc cgt ggc tcc cta ttt tca cca agg cga aat<br>Gln Ser Leu Leu Ser Ile Arg Gly Ser Leu Phe Ser Pro Arg Arg Asn<br>555                        560                        565 | 1973 |
| agc aga aca agc ctt ttc agc ttt aga ggg cga gca aag gat gtg gga<br>Ser Arg Thr Ser Leu Phe Ser Phe Arg Gly Arg Ala Lys Asp Val Gly<br>570                        575                        580                        585 | 2021 |
| tct gag aac gac ttc gca gat gat gag cac agc acc ttt gag gat aac<br>Ser Glu Asn Asp Phe Ala Asp Asp Glu His Ser Thr Phe Glu Asp Asn<br>                        590                        595                        600 | 2069 |
| gag agc cgt aga gat tcc ttg ttt gtg ccc cga cga cac gga gag aga<br>Glu Ser Arg Arg Asp Ser Leu Phe Val Pro Arg Arg His Gly Glu Arg<br>                605                        610                        615 | 2117 |
| cgc aac agc aac ctg agt cag acc agt agg tca tcc cgg atg ctg gca<br>Arg Asn Ser Asn Leu Ser Gln Thr Ser Arg Ser Ser Arg Met Leu Ala<br>              620                        625                        630 | 2165 |
| gtg ttt cca gcg aat ggg aag atg cac agc act gtg gat tgc aat ggt<br>Val Phe Pro Ala Asn Gly Lys Met His Ser Thr Val Asp Cys Asn Gly<br>635                        640                        645 | 2213 |

```
                                                          -continued gtg gtt tcc ttg gtt ggt gga cct tca gtt cct aca tcg cct gtt gga     2261
Val Val Ser Leu Val Gly Gly Pro Ser Val Pro Thr Ser Pro Val Gly
650             655                 660                 665 cag ctt ctg cca gag gtg ata ata gat aag cca gct act gat gac aat     2309
Gln Leu Leu Pro Glu Val Ile Ile Asp Lys Pro Ala Thr Asp Asp Asn
            670                 675                 680 gga aca acc act gaa act gaa atg aga aag aga agg tca agt tct ttc     2357
Gly Thr Thr Thr Glu Thr Glu Met Arg Lys Arg Arg Ser Ser Ser Phe
        685                 690                 695 cac gtt tcc atg gac ttt cta gaa gat cct tcc caa agg caa cga gca     2405
His Val Ser Met Asp Phe Leu Glu Asp Pro Ser Gln Arg Gln Arg Ala
    700                 705                 710 atg agt ata gcc agc att cta aca aat aca gta gaa gaa ctt gaa gaa     2453
Met Ser Ile Ala Ser Ile Leu Thr Asn Thr Val Glu Glu Leu Glu Glu
715                 720                 725 tcc agg cag aaa tgc cca ccc tgt tgg tat aaa ttt tcc aac ata ttc     2501
Ser Arg Gln Lys Cys Pro Pro Cys Trp Tyr Lys Phe Ser Asn Ile Phe
730                 735                 740                 745 tta atc tgg gac tgt tct cca tat tgg tta aaa gtg aaa cat gtt gtc     2549
Leu Ile Trp Asp Cys Ser Pro Tyr Trp Leu Lys Val Lys His Val Val
                750                 755                 760 aac ctg gtt gtg atg gac cca ttt gtt gac ctg gcc atc acc atc tgt     2597
Asn Leu Val Val Met Asp Pro Phe Val Asp Leu Ala Ile Thr Ile Cys
            765                 770                 775 att gtc tta aat act ctt ttc atg gcc atg gag cac tat cca atg acg     2645
Ile Val Leu Asn Thr Leu Phe Met Ala Met Glu His Tyr Pro Met Thr
        780                 785                 790 gac cat ttc aat aat gtg ctt aca gta gga aac ttg gtt ttc act ggg     2693
Asp His Phe Asn Asn Val Leu Thr Val Gly Asn Leu Val Phe Thr Gly
    795                 800                 805 atc ttt aca gca gaa atg ttt ctg aaa att att gcc atg gat cct tac     2741
Ile Phe Thr Ala Glu Met Phe Leu Lys Ile Ile Ala Met Asp Pro Tyr
810                 815                 820                 825 tat tat ttc caa gaa ggc tgg aat atc ttt gac ggt ttt att gtg acg     2789
Tyr Tyr Phe Gln Glu Gly Trp Asn Ile Phe Asp Gly Phe Ile Val Thr
                830                 835                 840 ctt agc ctg gta gaa ctt gga ctc gcc aat gtg gaa gga tta tct gtt     2837
Leu Ser Leu Val Glu Leu Gly Leu Ala Asn Val Glu Gly Leu Ser Val
            845                 850                 855 ctc cgt tca ttt cga ttg ctg cga gtt ttc aag ttg gca aaa tct tgg     2885
Leu Arg Ser Phe Arg Leu Leu Arg Val Phe Lys Leu Ala Lys Ser Trp
        860                 865                 870 cca acg tta aat atg cta ata aag atc atc ggc aat tcc gtg ggg gct     2933
Pro Thr Leu Asn Met Leu Ile Lys Ile Ile Gly Asn Ser Val Gly Ala
    875                 880                 885 ctg gga aat tta acc ctc gtc ttg gcc atc atc gtc ttc att ttt gcc     2981
Leu Gly Asn Leu Thr Leu Val Leu Ala Ile Ile Val Phe Ile Phe Ala
890                 895                 900                 905 gtg gtc ggc atg cag ctc ttt ggt aaa agc tac aaa gat tgt gtc tgc     3029
Val Val Gly Met Gln Leu Phe Gly Lys Ser Tyr Lys Asp Cys Val Cys
                910                 915                 920 aag atc gcc agt gat tgt caa ctc cca cgc tgg cac atg aat gac ttc     3077
Lys Ile Ala Ser Asp Cys Gln Leu Pro Arg Trp His Met Asn Asp Phe
            925                 930                 935 ttc cac tcc ttc ctg att gtg ttc cgc gtg ctg tgt ggg gag tgg ata     3125
Phe His Ser Phe Leu Ile Val Phe Arg Val Leu Cys Gly Glu Trp Ile
        940                 945                 950 gag acc atg tgg gac tgt atg gag gtt gct ggt caa gcc atg tgc ctt     3173
Glu Thr Met Trp Asp Cys Met Glu Val Ala Gly Gln Ala Met Cys Leu
    955                 960                 965
```

```
act gtc ttc atg atg gtc atg gtg att gga aac cta gtg gtc ctg aat    3221
Thr Val Phe Met Met Val Met Val Ile Gly Asn Leu Val Val Leu Asn
970                 975                 980                 985 ctc ttt ctg gcc ttg ctt ctg agc tca ttt agt gca gac aac ctt gca    3269
Leu Phe Leu Ala Leu Leu Leu Ser Ser Phe Ser Ala Asp Asn Leu Ala
            990                 995                 1000 gcc act gat gat gat aat gaa atg aat aat ctc caa att gct gtg        3314
Ala Thr Asp Asp Asp Asn Glu Met Asn Asn Leu Gln Ile Ala Val
        1005                1010                1015 gat agg atg cac aaa gga gta gct tat gtg aaa aga aaa ata tat        3359
Asp Arg Met His Lys Gly Val Ala Tyr Val Lys Arg Lys Ile Tyr
        1020                1025                1030 gaa ttt att caa cag tcc ttc att agg aaa caa aag att tta gat        3404
Glu Phe Ile Gln Gln Ser Phe Ile Arg Lys Gln Lys Ile Leu Asp
        1035                1040                1045 gaa att aaa cca ctt gat gat cta aac aac aag aaa gac agt tgt        3449
Glu Ile Lys Pro Leu Asp Asp Leu Asn Asn Lys Lys Asp Ser Cys
        1050                1055                1060 atg tcc aat cat aca aca gaa att ggg aaa gat ctt gac tat ctt        3494
Met Ser Asn His Thr Thr Glu Ile Gly Lys Asp Leu Asp Tyr Leu
        1065                1070                1075 aaa gat gta aat gga act aca agt ggt ata gga act ggc agc agt        3539
Lys Asp Val Asn Gly Thr Thr Ser Gly Ile Gly Thr Gly Ser Ser
        1080                1085                1090 gtt gaa aaa tac att att gat gaa agt gat tac atg tca ttc ata        3584
Val Glu Lys Tyr Ile Ile Asp Glu Ser Asp Tyr Met Ser Phe Ile
        1095                1100                1105 aac aac ccc agt ctt act gtg act gta cca att gct gta gga gaa        3629
Asn Asn Pro Ser Leu Thr Val Thr Val Pro Ile Ala Val Gly Glu
        1110                1115                1120 tct gac ttt gaa aat tta aac acg gaa gac ttt agt agt gaa tcg        3674
Ser Asp Phe Glu Asn Leu Asn Thr Glu Asp Phe Ser Ser Glu Ser
        1125                1130                1135 gat ctg gaa gaa agc aaa gag aaa ctg aat gaa agc agt agc tca        3719
Asp Leu Glu Glu Ser Lys Glu Lys Leu Asn Glu Ser Ser Ser Ser
        1140                1145                1150 tca gaa ggt agc act gtg gac atc ggc gca cct gta gaa gaa cag        3764
Ser Glu Gly Ser Thr Val Asp Ile Gly Ala Pro Val Glu Glu Gln
        1155                1160                1165 ccc gta gtg gaa cct gaa gaa act ctt gaa cca gaa gct tgt ttc        3809
Pro Val Val Glu Pro Glu Glu Thr Leu Glu Pro Glu Ala Cys Phe
        1170                1175                1180 act gaa ggc tgt gta caa aga ttc aag tgt tgt caa atc aat gtg        3854
Thr Glu Gly Cys Val Gln Arg Phe Lys Cys Cys Gln Ile Asn Val
        1185                1190                1195 gaa gaa ggc aga gga aaa caa tgg tgg aac ctg aga agg acg tgt        3899
Glu Glu Gly Arg Gly Lys Gln Trp Trp Asn Leu Arg Arg Thr Cys
        1200                1205                1210 ttc cga ata gtt gaa cat aac tgg ttt gag acc ttc att gtt ttc        3944
Phe Arg Ile Val Glu His Asn Trp Phe Glu Thr Phe Ile Val Phe
        1215                1220                1225 atg att ctc ctt agt agt ggt gct ctg gca ttt gaa gat ata tat        3989
Met Ile Leu Leu Ser Ser Gly Ala Leu Ala Phe Glu Asp Ile Tyr
        1230                1235                1240 att gat cag cga aag acg att aag acg atg ttg gaa tat gct gac        4034
Ile Asp Gln Arg Lys Thr Ile Lys Thr Met Leu Glu Tyr Ala Asp
        1245                1250                1255 aag gtt ttc act tac att ttc att ctg gaa atg ctt cta aaa tgg        4079
Lys Val Phe Thr Tyr Ile Phe Ile Leu Glu Met Leu Leu Lys Trp
        1260                1265                1270
```

```
gtg gca tat ggc tat caa aca tat ttc acc aat gcc tgg tgt tgg      4124
Val Ala Tyr Gly Tyr Gln Thr Tyr Phe Thr Asn Ala Trp Cys Trp
        1275            1280            1285 ctg gac ttc tta att gtt gat gtt tca ttg gtc agt tta aca gca      4169
Leu Asp Phe Leu Ile Val Asp Val Ser Leu Val Ser Leu Thr Ala
        1290            1295            1300 aat gcc ttg ggt tac tca gaa ctt gga gcc atc aaa tct ctc agg      4214
Asn Ala Leu Gly Tyr Ser Glu Leu Gly Ala Ile Lys Ser Leu Arg
        1305            1310            1315 aca cta aga gct ctg aga cct cta aga gcc tta tct cga ttt gaa      4259
Thr Leu Arg Ala Leu Arg Pro Leu Arg Ala Leu Ser Arg Phe Glu
        1320            1325            1330 ggg atg agg gtg gtt gtg aat gcc ctt tta gga gca att cca tcc      4304
Gly Met Arg Val Val Val Asn Ala Leu Leu Gly Ala Ile Pro Ser
        1335            1340            1345 atc atg aat gtg ctt ctg gtt tgt ctt ata ttc tgg cta att ttc      4349
Ile Met Asn Val Leu Leu Val Cys Leu Ile Phe Trp Leu Ile Phe
        1350            1355            1360 agc atc atg ggc gta aat ttg ttt gct ggc aaa ttc tac cac tgt      4394
Ser Ile Met Gly Val Asn Leu Phe Ala Gly Lys Phe Tyr His Cys
        1365            1370            1375 att aac acc aca act ggt gac agg ttt gac atc gaa gac gtg aat      4439
Ile Asn Thr Thr Thr Gly Asp Arg Phe Asp Ile Glu Asp Val Asn
        1380            1385            1390 aat cat act gat tgc cta aaa cta ata gaa aga aat gag act gct      4484
Asn His Thr Asp Cys Leu Lys Leu Ile Glu Arg Asn Glu Thr Ala
        1395            1400            1405 cga tgg aaa aat gtg aaa gta aac ttt gat aat gta gga ttt ggg      4529
Arg Trp Lys Asn Val Lys Val Asn Phe Asp Asn Val Gly Phe Gly
        1410            1415            1420 tat ctc tct ttg ctt caa gtt gcc aca ttc aaa gga tgg atg gat      4574
Tyr Leu Ser Leu Leu Gln Val Ala Thr Phe Lys Gly Trp Met Asp
        1425            1430            1435 ata atg tat gca gca gtt gat tcc aga aat gtg gaa ctc cag cct      4619
Ile Met Tyr Ala Ala Val Asp Ser Arg Asn Val Glu Leu Gln Pro
        1440            1445            1450 aag tat gaa aaa agt ctg tac atg tat ctt tac ttt gtt att ttc      4664
Lys Tyr Glu Lys Ser Leu Tyr Met Tyr Leu Tyr Phe Val Ile Phe
        1455            1460            1465 atc atc ttt ggg tcc ttc ttc acc ttg aac ctg ttt att ggt gtc      4709
Ile Ile Phe Gly Ser Phe Phe Thr Leu Asn Leu Phe Ile Gly Val
        1470            1475            1480 atc ata gat aat ttc aac cag cag aaa aag aag ttt gga ggt caa      4754
Ile Ile Asp Asn Phe Asn Gln Gln Lys Lys Lys Phe Gly Gly Gln
        1485            1490            1495 gac atc ttt atg aca gaa gaa cag aag aaa tac tat aat gca atg      4799
Asp Ile Phe Met Thr Glu Glu Gln Lys Lys Tyr Tyr Asn Ala Met
        1500            1505            1510 aaa aaa tta gga tcg aaa aaa ccg caa aag cct ata cct cga cca      4844
Lys Lys Leu Gly Ser Lys Lys Pro Gln Lys Pro Ile Pro Arg Pro
        1515            1520            1525 gga aac aaa ttt caa gga atg gtc ttt gac ttc gta acc aga caa      4889
Gly Asn Lys Phe Gln Gly Met Val Phe Asp Phe Val Thr Arg Gln
        1530            1535            1540 gtt ttt gac ata agc atc atg att ctc atc tgt ctt aac atg gtc      4934
Val Phe Asp Ile Ser Ile Met Ile Leu Ile Cys Leu Asn Met Val
        1545            1550            1555 aca atg atg gtg gaa aca gat gac cag agt gaa tat gtg act acc      4979
Thr Met Met Val Glu Thr Asp Asp Gln Ser Glu Tyr Val Thr Thr
        1560            1565            1570
```

```
                                                                    -continued att ttg tca cgc atc aat ctg gtg ttc att gtg cta ttt act gga         5024
Ile Leu Ser Arg Ile Asn Leu Val Phe Ile Val Leu Phe Thr Gly
        1575                1580                1585 gag tgt gta ctg aaa ctc atc tct cta cgc cat tat tat ttt acc         5069
Glu Cys Val Leu Lys Leu Ile Ser Leu Arg His Tyr Tyr Phe Thr
        1590                1595                1600 att gga tgg aat att ttt gat ttt gtg gtt gtc att ctc tcc att         5114
Ile Gly Trp Asn Ile Phe Asp Phe Val Val Val Ile Leu Ser Ile
        1605                1610                1615 gta ggt atg ttt ctt gcc gag ctg ata gaa aag tat ttc gtg tcc         5159
Val Gly Met Phe Leu Ala Glu Leu Ile Glu Lys Tyr Phe Val Ser
        1620                1625                1630 cct acc ctg ttc cga gtg atc cgt ctt gct agg att ggc cga atc         5204
Pro Thr Leu Phe Arg Val Ile Arg Leu Ala Arg Ile Gly Arg Ile
        1635                1640                1645 cta cgt ctg atc aaa gga gca aag ggg atc cgc acg ctg ctc ttt         5249
Leu Arg Leu Ile Lys Gly Ala Lys Gly Ile Arg Thr Leu Leu Phe
        1650                1655                1660 gct ttg atg atg tcc ctt cct gcg ttg ttt aac atc ggc ctc cta         5294
Ala Leu Met Met Ser Leu Pro Ala Leu Phe Asn Ile Gly Leu Leu
        1665                1670                1675 ctc ttc cta gtc atg ttc atc tac gcc atc ttt ggg atg tcc aac         5339
Leu Phe Leu Val Met Phe Ile Tyr Ala Ile Phe Gly Met Ser Asn
        1680                1685                1690 ttt gcc tat gtt aag agg gaa gtt ggg atc gat gac atg ttc aac         5384
Phe Ala Tyr Val Lys Arg Glu Val Gly Ile Asp Asp Met Phe Asn
        1695                1700                1705 ttt gag acc ttt ggc aac agc atg atc tgc cta ttc caa att aca         5429
Phe Glu Thr Phe Gly Asn Ser Met Ile Cys Leu Phe Gln Ile Thr
        1710                1715                1720 acc tct gct ggc tgg gat gga ttg cta gca ccc att ctc aac agt         5474
Thr Ser Ala Gly Trp Asp Gly Leu Leu Ala Pro Ile Leu Asn Ser
        1725                1730                1735 aag cca ccc gac tgt gac cct aat aaa gtt aac cct gga agc tca         5519
Lys Pro Pro Asp Cys Asp Pro Asn Lys Val Asn Pro Gly Ser Ser
        1740                1745                1750 gtt aag gga gac tgt ggg aac cca tct gtt gga att ttc ttt ttt         5564
Val Lys Gly Asp Cys Gly Asn Pro Ser Val Gly Ile Phe Phe Phe
        1755                1760                1765 gtc agt tac atc atc ata tcc ttc ctg gtt gtg gtg aac atg tac         5609
Val Ser Tyr Ile Ile Ile Ser Phe Leu Val Val Val Asn Met Tyr
        1770                1775                1780 atc gcg gtc atc ctg gag aac ttc agt gtt gct act gaa gaa agt         5654
Ile Ala Val Ile Leu Glu Asn Phe Ser Val Ala Thr Glu Glu Ser
        1785                1790                1795 gca gag cct ctg agt gag gat gac ttt gag atg ttc tat gag gtt         5699
Ala Glu Pro Leu Ser Glu Asp Asp Phe Glu Met Phe Tyr Glu Val
        1800                1805                1810 tgg gag aag ttt gat ccc gat gca act cag ttc atg gaa ttt gaa         5744
Trp Glu Lys Phe Asp Pro Asp Ala Thr Gln Phe Met Glu Phe Glu
        1815                1820                1825 aaa tta tct cag ttt gca gct gcg ctt gaa ccg cct ctc aat ctg         5789
Lys Leu Ser Gln Phe Ala Ala Ala Leu Glu Pro Pro Leu Asn Leu
        1830                1835                1840 cca caa cca aac aaa ctc cag ctc att gcc atg gat ttg ccc atg         5834
Pro Gln Pro Asn Lys Leu Gln Leu Ile Ala Met Asp Leu Pro Met
        1845                1850                1855 gtg agt ggt gac cgg atc cac tgt ctt gat atc tta ttt gct ttt         5879
Val Ser Gly Asp Arg Ile His Cys Leu Asp Ile Leu Phe Ala Phe
        1860                1865                1870
```

```
aca aag cgg gtt cta gga gag agt gga gag atg gat gct cta cga              5924
Thr Lys Arg Val Leu Gly Glu Ser Gly Glu Met Asp Ala Leu Arg
            1875                1880                1885 ata cag atg gaa gag cga ttc atg gct tcc aat cct tcc aag gtc              5969
Ile Gln Met Glu Glu Arg Phe Met Ala Ser Asn Pro Ser Lys Val
        1890                1895                1900 tcc tat cag cca atc act act act tta aaa cga aaa caa gag gaa              6014
Ser Tyr Gln Pro Ile Thr Thr Thr Leu Lys Arg Lys Gln Glu Glu
        1905                1910                1915 gta tct gct gtc att att cag cgt gct tac aga ggc cac ctt tta              6059
Val Ser Ala Val Ile Ile Gln Arg Ala Tyr Arg Gly His Leu Leu
        1920                1925                1930 aag cga act gta aaa caa gct tcc ttt acg tac aat aaa aac aaa              6104
Lys Arg Thr Val Lys Gln Ala Ser Phe Thr Tyr Asn Lys Asn Lys
        1935                1940                1945 atc aaa ggt ggg gct aat ctt ctt ata aaa gaa gac atg ata att              6149
Ile Lys Gly Gly Ala Asn Leu Leu Ile Lys Glu Asp Met Ile Ile
        1950                1955                1960 gac aga ata aat gaa aac tct att aca gaa aaa act gat ctg acc              6194
Asp Arg Ile Asn Glu Asn Ser Ile Thr Glu Lys Thr Asp Leu Thr
        1965                1970                1975 atg tcc act gca gct tgt cca cct tcc tat gac cgg gtg aca aag              6239
Met Ser Thr Ala Ala Cys Pro Pro Ser Tyr Asp Arg Val Thr Lys
        1980                1985                1990 cca att gtg gaa aaa cat gag caa gaa ggc aaa gat gaa aaa gcc              6284
Pro Ile Val Glu Lys His Glu Gln Glu Gly Lys Asp Glu Lys Ala
        1995                2000                2005 aaa ggg aaa taa atgaaaataa ataaaaataa ttgggtgaca aattgtttac              6336
Lys Gly Lys agcctgtgaa ggtgatgtat ttttatcaac aggactcctt taggaggtca atgccaaact       6396
gactgttttt acacaaatct ccttaaggtc agtgcctaca ataagacagt gaccccttgt       6456
cagcaaactg tgactctgtg taaaggggag atgaccttga caggaggtta ctgttctcac       6516
taccagctga cactgctgaa gataagatgc acaatggcta gtcagactgt agggaccagt       6576
ttcaaggggt gcaaacctgt gattttgggg ttgtttaaca tgaaacactt tagtgtagta       6636
attgtatcca ctgtttgcat ttcaactgcc acatttgtca catttttatg gaatctgtta       6696
gtggattcat ctttttgtta atccatgtgt ttattatatg tgactatttt tgtaaacgaa       6756
gtttctgttg agaaataggc taaggacctc tataacaggt atgccacctg ggggtatgg        6816
caaccacatg gccctcccag ctacacaaag tcgtggtttg catgagggca tgctgcactt       6876
agagatcatg catgagaaaa agtcacaaga aaaacaaatt cttaaatttc accatatttc       6936
tgggaggggt aattgggtga taagtggagg tgctttgttg atcttgtttt gcgaaatcca       6996
gccctagac caagtagatt atttgtgggt aggccagtaa atcttagcag gtgcaaactt        7056
cattcaaatg tttggagtca taaatgttat gtttcttttt gttgtattaa aaaaaaacc        7116
tgaatagtga atattgcccc tcaccctcca ccgccagaag actgaattga ccaaaattac       7176
tctttataaa tttctgcttt ttcctgcact ttgtttagcc atctttgggc tctcagcaag       7236
gttgacactg tatatgttaa tgaaatgcta tttattatgt aaatagtcat tttaccctgt       7296
ggtgcacgtt tgagcaaaca aataatgacc taagcacagt atttattgca tcaaatatgt       7356
accacaagaa atgtagagtg caagctttac acaggtaata aatgtattc tgtaccattt        7416
atagatagtt tggatgctat caatgcatgt ttatattacc atgctgctgt atctggtttc       7476
tctcactgct cagaatctca tttatgagaa accatatgtc agtggtaaag tcaaggaaat       7536
```

-continued

```
tgttcaacag atctcattta tttaagtcat taagcaatag tttgcagcac tttaacagct    7596
ttttggttat ttttacatt  taagtggata acatatggta tatagccaga ctgtacagac    7656
atgtttaaaa aaacacactg cttaacctat taaatatgtg tttagaattt tataagcaaa    7716
tataaatact gtaaaaagtc actttatttt attttcagc attatgtaca taaatatgaa     7776
gaggaaatta tcttcaggtt gatatcacaa tcacttttct tactttctgt ccatagtact    7836
ttttcatgaa agaaatttgc taaataagac atgaaaacaa gactgggtag ttgtagattt    7896
ctgcttttta aattacattt gctaatttta gattatttca caatttttaag gagcaaaata   7956
ggttcacgat tcatatccaa attatgcttt gcaattggaa aagggtttaa aattttattt    8016
atatttctgg tagtacctgt actaactgaa ttgaaggtag tgcttatgtt attttttgttc   8076
ttttttttctg acttcggttt atgtttttcat ttctttggag taatgctgct ctagattgtt  8136
ctaaatagaa tgtgggcttc ataatttttt tttccacaaa aacagagtag tcaacttata   8196
tagtcaatta catcaggaca ttttgtgttt cttacagaag caaaccatag gctcctcttt    8256
tccttaaaac tacttagata aactgtattc gtgaactgca tgctggaaaa tgctactatt   8316
atgctaaata atgctaacca acatttaaaa tgtgcaaaac taataaagat tacattttt    8376
atttt                                                                8381
```

<210> SEQ ID NO 12
<211> LENGTH: 2009
<212> TYPE: PRT
<213> ORGANISM: Homo sapiens

<400> SEQUENCE: 12

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Leu
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220
```

-continued

```
Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
                260                 265                 270

Leu Arg Asn Lys Cys Ile Gln Trp Pro Pro Thr Asn Ala Ser Leu Glu
            275                 280                 285

Glu His Ser Ile Glu Lys Asn Ile Thr Val Asn Tyr Asn Gly Thr Leu
        290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
                340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
                420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Gln Ala Ala Thr Ala
450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
                580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
        610                 615                 620

Thr Ser Arg Ser Ser Arg Met Leu Ala Val Phe Pro Ala Asn Gly Lys
625                 630                 635                 640
```

-continued

Met His Ser Thr Val Asp Cys Asn Gly Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
                675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750

Tyr Trp Leu Lys Val Lys His Val Val Asn Leu Val Val Met Asp Pro
                755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
                835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
    995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

-continued

```
Leu Asn Asn Lys Lys Asp Ser Cys Met Ser Asn His Thr Thr Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440
```

```
Ser Arg Asn Val Glu Leu Gln Pro Lys Tyr Glu Lys Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
1625                1630                1635

Arg Leu Ala Arg Ile Gly Arg Ile Leu Arg Leu Ile Lys Gly Ala
1640                1645                1650

Lys Gly Ile Arg Thr Leu Leu Phe Ala Leu Met Met Ser Leu Pro
1655                1660                1665

Ala Leu Phe Asn Ile Gly Leu Leu Leu Phe Leu Val Met Phe Ile
1670                1675                1680

Tyr Ala Ile Phe Gly Met Ser Asn Phe Ala Tyr Val Lys Arg Glu
1685                1690                1695

Val Gly Ile Asp Asp Met Phe Asn Phe Glu Thr Phe Gly Asn Ser
1700                1705                1710

Met Ile Cys Leu Phe Gln Ile Thr Thr Ser Ala Gly Trp Asp Gly
1715                1720                1725

Leu Leu Ala Pro Ile Leu Asn Ser Lys Pro Pro Asp Cys Asp Pro
1730                1735                1740

Asn Lys Val Asn Pro Gly Ser Ser Val Lys Gly Asp Cys Gly Asn
1745                1750                1755

Pro Ser Val Gly Ile Phe Phe Phe Val Ser Tyr Ile Ile Ile Ser
1760                1765                1770

Phe Leu Val Val Val Asn Met Tyr Ile Ala Val Ile Leu Glu Asn
1775                1780                1785

Phe Ser Val Ala Thr Glu Glu Ser Ala Glu Pro Leu Ser Glu Asp
1790                1795                1800

Asp Phe Glu Met Phe Tyr Glu Val Trp Glu Lys Phe Asp Pro Asp
1805                1810                1815

Ala Thr Gln Phe Met Glu Phe Glu Lys Leu Ser Gln Phe Ala Ala
1820                1825                1830
```

```
Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Gly His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005
```

```
<210> SEQ ID NO 13
<211> LENGTH: 27
<212> TYPE: DNA
<213> ORGANISM: Homo sapiens

<400> SEQUENCE: 13
agatgaccag agtgaatatg tgactac                                          27

<210> SEQ ID NO 14
<211> LENGTH: 24
<212> TYPE: DNA
<213> ORGANISM: Homo sapiens

<400> SEQUENCE: 14
ccaatggtaa aataataatg gcgt                                             24

<210> SEQ ID NO 15
<211> LENGTH: 20
<212> TYPE: DNA
<213> ORGANISM: Homo sapiens

<400> SEQUENCE: 15
taccatagag tgaggcgagg                                                  20

<210> SEQ ID NO 16
<211> LENGTH: 20
<212> TYPE: DNA
<213> ORGANISM: Homo sapiens

<400> SEQUENCE: 16
atggacttcc tgctctgccc                                                  20
```

```
<210> SEQ ID NO 17
<211> LENGTH: 22
<212> TYPE: DNA
<213> ORGANISM: Homo sapiens

<400> SEQUENCE: 17
cctctagctc atgtttcatg ac                                          22

<210> SEQ ID NO 18
<211> LENGTH: 20
<212> TYPE: DNA
<213> ORGANISM: Homo sapiens

<400> SEQUENCE: 18
tgcagtaggc aattagcagc                                             20

<210> SEQ ID NO 19
<211> LENGTH: 26
<212> TYPE: DNA
<213> ORGANISM: Homo sapiens

<400> SEQUENCE: 19
ctaattaaga agagatccag tgacag                                      26

<210> SEQ ID NO 20
<211> LENGTH: 27
<212> TYPE: DNA
<213> ORGANISM: Homo sapiens

<400> SEQUENCE: 20
gctataaagt gcttacagat catgtac                                     27

<210> SEQ ID NO 21
<211> LENGTH: 24
<212> TYPE: DNA
<213> ORGANISM: Homo sapiens

<400> SEQUENCE: 21
ccctgaattt tggctaagct gcag                                        24

<210> SEQ ID NO 22
<211> LENGTH: 27
<212> TYPE: DNA
<213> ORGANISM: Homo sapiens

<400> SEQUENCE: 22
ctacattaag acacagtttc aaaatcc                                     27

<210> SEQ ID NO 23
<211> LENGTH: 21
<212> TYPE: DNA
<213> ORGANISM: Homo sapiens

<400> SEQUENCE: 23
gggctacgtt tcatttgtat g                                           21

<210> SEQ ID NO 24
<211> LENGTH: 27
<212> TYPE: DNA
<213> ORGANISM: Homo sapiens

<400> SEQUENCE: 24
gcaacctatt cttaaagcat aagactg                                     27
```

```
<210> SEQ ID NO 25
<211> LENGTH: 20
<212> TYPE: DNA
<213> ORGANISM: Homo sapiens

<400> SEQUENCE: 25
aggctctttg tacctacagc                                               20

<210> SEQ ID NO 26
<211> LENGTH: 20
<212> TYPE: DNA
<213> ORGANISM: Homo sapiens

<400> SEQUENCE: 26
catgtagggt ccgtctcatt                                               20

<210> SEQ ID NO 27
<211> LENGTH: 23
<212> TYPE: DNA
<213> ORGANISM: Homo sapiens

<400> SEQUENCE: 27
cacacgtgtt aagtcttcat agt                                           23

<210> SEQ ID NO 28
<211> LENGTH: 21
<212> TYPE: DNA
<213> ORGANISM: Homo sapiens

<400> SEQUENCE: 28 agccccctcaa gtatttatcc t                                            21

<210> SEQ ID NO 29
<211> LENGTH: 21
<212> TYPE: DNA
<213> ORGANISM: Homo sapiens

<400> SEQUENCE: 29
gaacctgacc ttcctgttct c                                             21

<210> SEQ ID NO 30
<211> LENGTH: 22
<212> TYPE: DNA
<213> ORGANISM: Homo sapiens

<400> SEQUENCE: 30
gttggctgtt atcttcagtt tc                                            22

<210> SEQ ID NO 31
<211> LENGTH: 23
<212> TYPE: DNA
<213> ORGANISM: Homo sapiens

<400> SEQUENCE: 31
gactaggcaa tatcatagca tag                                           23

<210> SEQ ID NO 32
<211> LENGTH: 23
<212> TYPE: DNA
<213> ORGANISM: Homo sapiens

<400> SEQUENCE: 32
ctttctacta tattatcatc cgg                                           23
```

```
<210> SEQ ID NO 33
<211> LENGTH: 20
<212> TYPE: DNA
<213> ORGANISM: Homo sapiens

<400> SEQUENCE: 33
ttgaaagttg aagccaccac                                              20

<210> SEQ ID NO 34
<211> LENGTH: 20
<212> TYPE: DNA
<213> ORGANISM: Homo sapiens

<400> SEQUENCE: 34
ccacctgctc ttaggtactc                                              20

<210> SEQ ID NO 35
<211> LENGTH: 21
<212> TYPE: DNA
<213> ORGANISM: Homo sapiens

<400> SEQUENCE: 35
gccatgcaaa tacttcagcc c                                            21

<210> SEQ ID NO 36
<211> LENGTH: 23
<212> TYPE: DNA
<213> ORGANISM: Homo sapiens

<400> SEQUENCE: 36
cacaacagtg gttgattcag ttg                                          23

<210> SEQ ID NO 37
<211> LENGTH: 23
<212> TYPE: DNA
<213> ORGANISM: Homo sapiens

<400> SEQUENCE: 37
tgaatgctga aatctccttc tac                                          23

<210> SEQ ID NO 38
<211> LENGTH: 21
<212> TYPE: DNA
<213> ORGANISM: Homo sapiens

<400> SEQUENCE: 38
ctcaggttgc tgttgcgtct c                                            21

<210> SEQ ID NO 39
<211> LENGTH: 21
<212> TYPE: DNA
<213> ORGANISM: Homo sapiens

<400> SEQUENCE: 39
gataacgaga gccgtagaga t                                            21

<210> SEQ ID NO 40
<211> LENGTH: 20
<212> TYPE: DNA
<213> ORGANISM: Homo sapiens

<400> SEQUENCE: 40
tctgtagaaa cactggctgg                                              20
```

<210> SEQ ID NO 41
<211> LENGTH: 21
<212> TYPE: DNA
<213> ORGANISM: Homo sapiens

<400> SEQUENCE: 41
catgaaattc actgtgtcac c                                          21

<210> SEQ ID NO 42
<211> LENGTH: 21
<212> TYPE: DNA
<213> ORGANISM: Homo sapiens

<400> SEQUENCE: 42
cagctcttga attagactgt c                                          21

<210> SEQ ID NO 43
<211> LENGTH: 20
<212> TYPE: DNA
<213> ORGANISM: Homo sapiens

<400> SEQUENCE: 43
atccttggga ggtttagagt                                            20

<210> SEQ ID NO 44
<211> LENGTH: 21
<212> TYPE: DNA
<213> ORGANISM: Homo sapiens

<400> SEQUENCE: 44
catcacaacc aggttgacaa c                                          21

<210> SEQ ID NO 45
<211> LENGTH: 21
<212> TYPE: DNA
<213> ORGANISM: Homo sapiens

<400> SEQUENCE: 45
ctgggactgt tctccatatt g                                          21

<210> SEQ ID NO 46
<211> LENGTH: 20
<212> TYPE: DNA
<213> ORGANISM: Homo sapiens

<400> SEQUENCE: 46
gcatgaagga tggttgaaag                                            20

<210> SEQ ID NO 47
<211> LENGTH: 23
<212> TYPE: DNA
<213> ORGANISM: Homo sapiens

<400> SEQUENCE: 47
cattgtggga aaatagcata agc                                        23

<210> SEQ ID NO 48
<211> LENGTH: 20
<212> TYPE: DNA
<213> ORGANISM: Homo sapiens

<400> SEQUENCE: 48
gctatgcaga accctgattg                                            20

```
<210> SEQ ID NO 49
<211> LENGTH: 20
<212> TYPE: DNA
<213> ORGANISM: Homo sapiens

<400> SEQUENCE: 49
tgagacggtt agggcagatc                                               20

<210> SEQ ID NO 50
<211> LENGTH: 21
<212> TYPE: DNA
<213> ORGANISM: Homo sapiens

<400> SEQUENCE: 50
agaagtcatt catgtgccag c                                             21

<210> SEQ ID NO 51
<211> LENGTH: 21
<212> TYPE: DNA
<213> ORGANISM: Homo sapiens

<400> SEQUENCE: 51
ctgcaagatc gccagtgatt g                                             21

<210> SEQ ID NO 52
<211> LENGTH: 20
<212> TYPE: DNA
<213> ORGANISM: Homo sapiens

<400> SEQUENCE: 52
acatgtgcac aatgtgcagg                                               20

<210> SEQ ID NO 53
<211> LENGTH: 22
<212> TYPE: DNA
<213> ORGANISM: Homo sapiens

<400> SEQUENCE: 53
gtggtgtttc cttctcatca ag                                            22

<210> SEQ ID NO 54
<211> LENGTH: 22
<212> TYPE: DNA
<213> ORGANISM: Homo sapiens

<400> SEQUENCE: 54
tctgctgtat gattggacat ac                                            22

<210> SEQ ID NO 55
<211> LENGTH: 22
<212> TYPE: DNA
<213> ORGANISM: Homo sapiens

<400> SEQUENCE: 55
caacagtcct tcattaggaa ac                                            22

<210> SEQ ID NO 56
<211> LENGTH: 22
<212> TYPE: DNA
<213> ORGANISM: Homo sapiens

<400> SEQUENCE: 56
accttcccac acctatagaa tc                                            22
```

```
<210> SEQ ID NO 57
<211> LENGTH: 21
<212> TYPE: DNA
<213> ORGANISM: Homo sapiens

<400> SEQUENCE: 57
cttggcaggc aacttattac c                                     21

<210> SEQ ID NO 58
<211> LENGTH: 22
<212> TYPE: DNA
<213> ORGANISM: Homo sapiens

<400> SEQUENCE: 58
caagctgcac tccaaatgaa ag                                    22

<210> SEQ ID NO 59
<211> LENGTH: 24
<212> TYPE: DNA
<213> ORGANISM: Homo sapiens

<400> SEQUENCE: 59
tggaagcaga gacactttat ctac                                  24

<210> SEQ ID NO 60
<211> LENGTH: 24
<212> TYPE: DNA
<213> ORGANISM: Homo sapiens

<400> SEQUENCE: 60
gtgctgtatc acctttctt aatc                                   24

<210> SEQ ID NO 61
<211> LENGTH: 24
<212> TYPE: DNA
<213> ORGANISM: Homo sapiens

<400> SEQUENCE: 61
cctattccaa tgaaatgtca tatg                                  24

<210> SEQ ID NO 62
<211> LENGTH: 21
<212> TYPE: DNA
<213> ORGANISM: Homo sapiens

<400> SEQUENCE: 62
caagctacct tgaacagaga c                                     21

<210> SEQ ID NO 63
<211> LENGTH: 24
<212> TYPE: DNA
<213> ORGANISM: Homo sapiens

<400> SEQUENCE: 63
ctacacattg aatgatgatt ctgt                                  24

<210> SEQ ID NO 64
<211> LENGTH: 24
<212> TYPE: DNA
<213> ORGANISM: Homo sapiens

<400> SEQUENCE: 64
gctatataca atacttcagg ttct                                  24
```

```
<210> SEQ ID NO 65
<211> LENGTH: 21
<212> TYPE: DNA
<213> ORGANISM: Homo sapiens

<400> SEQUENCE: 65
accagagatt actagggaa t                                            21

<210> SEQ ID NO 66
<211> LENGTH: 21
<212> TYPE: DNA
<213> ORGANISM: Homo sapiens

<400> SEQUENCE: 66
ccatcgagca gtctcatttc t                                           21

<210> SEQ ID NO 67
<211> LENGTH: 21
<212> TYPE: DNA
<213> ORGANISM: Homo sapiens

<400> SEQUENCE: 67
acaactggtg acaggtttga c                                           21

<210> SEQ ID NO 68
<211> LENGTH: 24
<212> TYPE: DNA
<213> ORGANISM: Homo sapiens

<400> SEQUENCE: 68
ctgggctcat aaacttgtac taac                                        24

<210> SEQ ID NO 69
<211> LENGTH: 21
<212> TYPE: DNA
<213> ORGANISM: Homo sapiens

<400> SEQUENCE: 69
actgtcttgg tccaaaatct g                                           21

<210> SEQ ID NO 70
<211> LENGTH: 24
<212> TYPE: DNA
<213> ORGANISM: Homo sapiens

<400> SEQUENCE: 70
ttcgattaat tttaccacct gatc                                        24

<210> SEQ ID NO 71
<211> LENGTH: 21
<212> TYPE: DNA
<213> ORGANISM: Homo sapiens

<400> SEQUENCE: 71
agcaccagtg acatttccaa c                                           21

<210> SEQ ID NO 72
<211> LENGTH: 21
<212> TYPE: DNA
<213> ORGANISM: Homo sapiens

<400> SEQUENCE: 72
ggcagagaaa acactccaag g                                           21
```

<210> SEQ ID NO 73
<211> LENGTH: 21
<212> TYPE: DNA
<213> ORGANISM: Homo sapiens

<400> SEQUENCE: 73
gacacagttt taaccagttt g                                              21

<210> SEQ ID NO 74
<211> LENGTH: 21
<212> TYPE: DNA
<213> ORGANISM: Homo sapiens

<400> SEQUENCE: 74
tgtgagacaa gcatgcaagt t                                              21

<210> SEQ ID NO 75
<211> LENGTH: 21
<212> TYPE: DNA
<213> ORGANISM: Homo sapiens

<400> SEQUENCE: 75
cagggccaat gactactttg c                                              21

<210> SEQ ID NO 76
<211> LENGTH: 25
<212> TYPE: DNA
<213> ORGANISM: Homo sapiens

<400> SEQUENCE: 76
ctgattgctg ggatgatctt gaatc                                          25

<210> SEQ ID NO 77
<211> LENGTH: 23
<212> TYPE: DNA
<213> ORGANISM: Homo sapiens

<400> SEQUENCE: 77
cgcatgattt cttcactggt tgg                                            23

<210> SEQ ID NO 78
<211> LENGTH: 21
<212> TYPE: DNA
<213> ORGANISM: Homo sapiens

<400> SEQUENCE: 78
gcgtagatga acatgactag g                                              21

<210> SEQ ID NO 79
<211> LENGTH: 21
<212> TYPE: DNA
<213> ORGANISM: Homo sapiens

<400> SEQUENCE: 79
tcctgcgttg tttaacatcg g                                              21

<210> SEQ ID NO 80
<211> LENGTH: 21
<212> TYPE: DNA
<213> ORGANISM: Homo sapiens

<400> SEQUENCE: 80
attccaacag atgggttccc a                                              21

```
<210> SEQ ID NO 81
<211> LENGTH: 21
<212> TYPE: DNA
<213> ORGANISM: Homo sapiens

<400> SEQUENCE: 81
tggaagctca gttaagggag a                                    21

<210> SEQ ID NO 82
<211> LENGTH: 21
<212> TYPE: DNA
<213> ORGANISM: Homo sapiens

<400> SEQUENCE: 82
agcgcagctg caaactgaga t                                    21

<210> SEQ ID NO 83
<211> LENGTH: 22
<212> TYPE: DNA
<213> ORGANISM: Homo sapiens

<400> SEQUENCE: 83
ccgatgcaac tcagttcatg ga                                   22

<210> SEQ ID NO 84
<211> LENGTH: 21
<212> TYPE: DNA
<213> ORGANISM: Homo sapiens

<400> SEQUENCE: 84
gtagtgattg gctgatagga g                                    21

<210> SEQ ID NO 85
<211> LENGTH: 24
<212> TYPE: DNA
<213> ORGANISM: Homo sapiens

<400> SEQUENCE: 85
agagcgattc atggcttcca atcc                                 24

<210> SEQ ID NO 86
<211> LENGTH: 26
<212> TYPE: DNA
<213> ORGANISM: Homo sapiens

<400> SEQUENCE: 86
tgccttcttg ctcatgtttt tccaca                               26

<210> SEQ ID NO 87
<211> LENGTH: 22
<212> TYPE: DNA
<213> ORGANISM: Homo sapiens

<400> SEQUENCE: 87
cctatgaccg ggtgacaaag cc                                   22

<210> SEQ ID NO 88
<211> LENGTH: 22
<212> TYPE: DNA
<213> ORGANISM: Homo sapiens

<400> SEQUENCE: 88
tgctgacaag gggtcactgt ct                                   22
```

<210> SEQ ID NO 89
<211> LENGTH: 8381
<212> TYPE: DNA
<213> ORGANISM: Homo sapiens

<400> SEQUENCE: 89

| | | | | | |
|---|---|---|---|---|---|
| atactgcaga | ggtctctggt | gcatgtgtgt | atgtgtgcgt | ttgtgtgtgt | ttgtgtgtct | 60 |
| gtgtgttctg | ccccagtgag | actgcagccc | ttgtaaatac | tttgacacct | tttgcaagaa | 120 |
| ggaatctgaa | caattgcaac | tgaaggcaca | ttgttatcat | ctcgtctttg | ggtgatgctg | 180 |
| ttcctcactg | cagatggata | attttccttt | taatcaggaa | tttcatatgc | agaataaatg | 240 |
| gtaattaaaa | tgtgcaggat | gacaagatgg | agcaaacagt | gcttgtacca | ccaggacctg | 300 |
| acagcttcaa | cttcttcacc | agagaatctc | ttgcggctat | tgaaagacgc | attgcagaag | 360 |
| aaaaggcaaa | gaatcccaaa | ccagacaaaa | agatgacga | cgaaaatggc | ccaaagccaa | 420 |
| atagtgactt | ggaagctgga | aagaaccttc | catttattta | tggagacatt | cctccagaga | 480 |
| tggtgtcaga | gccctggag | gacctggacc | cctactatat | caataagaaa | acttttatag | 540 |
| tattgaataa | attgaaggcc | atcttccggt | tcagtgccac | ctctgccctg | tacatttaa | 600 |
| ctcccttcaa | tcctcttagg | aaaatagcta | ttaagatttt | ggtacattca | ttattcagca | 660 |
| tgctaattat | gtgcactatt | ttgacaaact | gtgtgtttat | gacaatgagt | aaccctcctg | 720 |
| attggacaaa | gaatgtagaa | tacaccttca | caggaatata | tactttttgaa | tcacttataa | 780 |
| aaattattgc | aagggggattc | tgtttagaag | attttacttt | ccttcgggat | ccatggaact | 840 |
| ggctcgattt | cactgtcatt | acatttgcgt | acgtcacaga | gtttgtggac | ctgggcaatg | 900 |
| tctcggcatt | gagaacattc | agagttctcc | gagcattgaa | gacgatttca | gtcattccag | 960 |
| gcctgaaaac | cattgtggga | gccctgatcc | agtctgtgaa | gaagctctca | gatgtaatga | 1020 |
| tcctgactgt | gttctgtctg | agcgtatttg | ctctaattgg | gctgcagctg | ttcatgggca | 1080 |
| acctgaggaa | taaatgtata | caatggcctc | caccaatgc | ttccttggag | gaacatagta | 1140 |
| tagaaaagaa | tataactgtg | aattataatg | gtacacttat | aaatgaaact | gtctttgagt | 1200 |
| ttgactggaa | gtcatatatt | caagattcaa | gatatcatta | tttcctggag | ggtttttag | 1260 |
| atgcactact | atgtggaaat | agctctgatg | caggccaatg | tccagaggga | tatatgtgtg | 1320 |
| tgaaagctgg | tagaaatccc | aattatggct | acacaagctt | tgataccttc | agttgggctt | 1380 |
| ttttgtcctt | gtttcgacta | atgactcagg | acttctggga | aaatctttat | caactgacat | 1440 |
| tacgtgctgc | tgggaaaacg | tacatgatat | tttttgtatt | ggtcattttc | ttgggctcat | 1500 |
| tctacctaat | aaatttgatc | ctggctgtgg | tggccatggc | ctacgaggaa | cagaatcagg | 1560 |
| ccaccttgga | agaagcagaa | cagaaagagg | ccgaatttca | gcagatgatt | gaacagctta | 1620 |
| aaaagcaaca | ggaggcagct | cagcaggcag | caacggcaac | tgcctcagaa | cattccagag | 1680 |
| agcccagtgc | agcaggcagg | ctctcagaca | gctcatctga | agcctctaag | ttgagttcca | 1740 |
| agagtgctaa | ggaaagaaga | aatcggagga | agaaaagaaa | acagaaagag | cagtctggtg | 1800 |
| gggaagagaa | agatgaggat | gaattccaaa | aatctgaatc | tgaggacagc | atcaggagga | 1860 |
| aaggttttcg | cttctccatt | gaagggaacc | gattgacata | tgaaaagagg | tactcctccc | 1920 |
| cacaccagtc | tttgttgagc | atccgtggct | ccctatttc | accaaggcga | aatagcagaa | 1980 |
| caagcctttt | cagctttaga | gggcgagcaa | aggatgtggg | atctgagaac | gacttcgcag | 2040 |
| atgatgagca | cagcaccttt | gaggataacg | agagccgtag | agattccttg | tttgtgcccc | 2100 |
| gacgacacgg | agagagacgc | aacagcaacc | tgagtcagac | cagtaggtca | tcccgggatgc | 2160 |

```
tggcagtgtt tccagcgaat gggaagatgc acagcactgt ggattgcaat ggtgtggttt    2220
ccttggttgg tggaccttca gttcctacat cgcctgttgg acagcttctg ccagaggtga    2280
taatagataa gccagctact gatgacaatg aacaaccac tgaaactgaa atgagaaaga     2340
gaaggtcaag ttctttccac gtttccatgg actttctaga agatccttcc caaaggcaac   2400
gagcaatgag tatagccagc attctaacaa atacagtaga agaacttgaa gaatccaggc   2460
agaaatgccc accctgttgg tataaatttt ccaacatatt cttaatctgg gactgttctc   2520
catattggtt aaaagtgaaa catgttgtca acctggttgt gatggaccca tttgttgacc   2580
tggccatcac catctgtatt gtcttaaata ctcttttcat ggccatggag cactatccaa   2640
tgacggacca tttcaataat gtgcttacag taggaaactt ggttttcact gggatctta   2700 cagcagaaat gtttctgaaa attattgcca tggatcctta ctattatttc caagaaggct   2760
ggaatatctt tgacggtttt attgtgacgc ttagcctggt agaacttgga ctcgccaatg   2820
tggaaggatt atctgttctc cgttcatttc gattgctgcg agttttcaag ttggcaaaat   2880
cttggccaac gttaaatatg ctaataaaga tcatcggcaa ttccgtgggg gctctgggaa   2940
atttaaccct cgtcttggcc atcatcgtct tcatttttgc cgtggtcggc atgcagctct   3000
ttggtaaaag ctacaaagat tgtgtctgca agatcgccag tgattgtcaa ctcccacgct   3060
ggcacatgaa tgacttcttc cactccttcc tgattgtgtt ccgcgtgctg tgtgggagt    3120 ggatagagac catgtgggac tgtatggagg ttgctggtca agccatgtgc cttactgtct   3180
tcatgatggt catggtgatt ggaaacctag tggtcctgaa tctcttttctg gccttgcttc   3240 tgagctcatt tagtgcagac aaccttgcag ccactgatga tgataatgaa atgaataatc   3300
tccaaattgc tgtggatagg atgcacaaag gagtagctta tgtgaaaaga aaaatatatg   3360
aatttattca acagtccttc attaggaaac aaaagatttt agatgaaatt aaaccacttg   3420
atgatctaaa caacaagaaa gacagttgta tgtccaatca tacaacgaaa attgggaaag   3480
atcttgacta tcttaaagat gtaaatggaa ctacaagtgg tataggaact ggcagcagtg   3540
ttgaaaaata cattattgat gaaagtgatt acatgtcatt cataaacaac cccagtctta   3600
ctgtgactgt accaattgct gtaggagaat ctgactttga aaatttaaac acggaagact   3660
ttagtagtga atcggatctg gaagaaagca aagagaaact gaatgaaagc agtagctcat   3720
cagaaggtag cactgtggac atcggcgcac ctgtagaaga acagcccgta gtggaacctg   3780
aagaaactct tgaaccagaa gcttgtttca ctgaaggctg tgtacaaaga ttcaagtgtt   3840
gtcaaatcaa tgtggaagaa ggcagaggaa acaatggtg gaacctgaga aggacgtgtt    3900
tccgaatagt tgaacataac tggtttgaga ccttcattgt tttcatgatt ctccttagta   3960
gtggtgctct ggcatttgaa gatatatata ttgatcagcg aaagacgatt aagacgatgt   4020
tggaatatgc tgacaaggtt ttcacttaca ttttcattct ggaaatgctt ctaaaatggg   4080
tggcatatgg ctatcaaaca tatttcacca atgcctggtg ttggctggac ttcttaattg   4140
ttgatgtttc attggtcagt ttaacagcaa atgccttggg ttactcagaa cttggagcca   4200
tcaaatctct caggacacta agagctctga gacctctaag agcctatctc cgatttgaag   4260
ggatgagggt ggttgtgaat gccctttag gagcaattcc atccatcatg aatgtgcttc    4320
tggtttgtct tatattctgg ctaattttca gcatcatggg cgtaaatttg tttgctggca   4380
aattctacca ctgtattaac accacaactg gtgacaggtt tgacatcgaa gacgtgaata   4440
atcatactga ttgcctaaaa ctaatagaaa gaaatgagac tgctcgatgg aaaaatgtga   4500
aagtaaactt tgataatgta ggatttgggt atctctcttt gcttcaagtt gccacattca   4560
```

```
aaggatggat ggatataatg tatgcagcag ttgattccag aaatgtgaaa ctccagccta    4620
agtatgaaaa aagtctgtac atgtatcttt actttgttat tttcatcatc tttgggtcct    4680
tcttcacctt gaacctgttt attggtgtca tcatagataa tttcaaccag cagaaaaaga    4740
agtttggagg tcaagacatc tttatgacag aagaacagaa gaaatactat aatgcaatga    4800
aaaaattagg atcgaaaaaa ccgcaaaagc ctatacctcg accaggaaac aaatttcaag    4860
gaatggtctt tgacttcgta accagacaag ttttttgacat aagcatcatg attctcatct    4920
gtcttaacat ggtcacaatg atggtggaaa cagatgacca gagtgaatat gtgactacca    4980
ttttgtcacg catcaatctg gtgttcattg tgctatttac tggagagtgt gtactgaaac    5040
tcatctctct acgccattat tattttacca ttggatggaa tatttttgat tttgtggttg    5100
tcattctctc cattgtaggt atgtttcttg ccgagctgat agaaaagtat ttcgtgtccc    5160
ctaccctgtt ccgagtgatc cgtcttgcta ggattggccg aatcctacgt ctgatcaaag    5220
gagcaaaggg gatccgcacg ctgctctttg ctttgatgat gtcccttcct gcgttgttta    5280
acatcggcct cctactcttc ctagtcatgt tcatctacgc catctttggg atgtccaact    5340
ttgcctatgt taagagggaa gttgggatcg atgacatgtt caactttgag acctttggca    5400
acagcatgat ctgcctattc caaattacaa cctctgctgg ctgggatgga ttgctagcac    5460
ccattctcaa cagtaagcca cccgactgtg accctaataa agttaaccct ggaagctcag    5520
ttaagggaga ctgtgggaac ccatctgttg gaattttctt ttttgtcagt tacatcatca    5580
tatccttcct ggttgtggtg aacatgtaca tcgcggtcat cctggagaac ttcagtgttg    5640
ctactgaaga aagtgcagag cctctgagtg aggatgactt tgagatgttc tatgaggttt    5700
gggagaagtt tgatcccgat gcaactcagt tcatggaatt tgaaaaatta tctcagtttg    5760
cagctgcgct tgaaccgcct ctcaatctgc cacaaccaaa caaactccag ctcattgcca    5820
tggatttgcc catggtgagt ggtgaccgga tccactgtct tgatatctta tttgctttta    5880
caaagcgggt tctaggagag agtggagaga tggatgctct acgaatacag atggaagagc    5940
gattcatggc ttccaatcct tccaaggtct cctatcagcc aatcactact actttaaaac    6000
gaaaacaaga ggaagtatct gctgtcatta ttcagcgtgc ttacagacgc caccttttaa    6060
agcgaactgt aaaacaagct tcctttacgt acaataaaaa caaatcaaa ggtgggcta    6120 atcttcttat aaaagaagac atgataattg acagaataaa tgaaaactct attacagaaa    6180
aaactgatct gaccatgtcc actgcagctt gtccaccttc ctatgaccgg gtgacaaagc    6240
caattgtgga aaaacatgag caagaaggca agatgaaaa agccaaaggg aaataaatga    6300
aaataaataa aaataattgg gtgacaaatt gtttacagcc tgtgaaggtg atgtatttt    6360 atcaacagga ctccttttagg aggtcaatgc caaactgact gtttttacac aaatctcctt    6420
aaggtcagtg cctacaataa gacagtgacc ccttgtcagc aaactgtgac tctgtgtaaa    6480
ggggagatga ccttgacagg aggttactgt tctcactacc agctgacact gctgaagata    6540
agatgcacaa tggctagtca gactgtaggg accagtttca aggggtgcaa acctgtgatt    6600
ttggggttgt ttaacatgaa acactttagt gtagtaattg tatccactgt ttgcatttca    6660
actgccacat ttgtcacatt tttatggaat ctgttagtgg attcatcttt ttgttaatcc    6720
atgtgtttat tatatgtgac tattttttgta aacgaagttt ctgttgagaa ataggctaag    6780
gacctctata acaggtatgc cacctggggg gtatggcaac cacatggccc tcccagctac    6840
acaaagtcgt ggtttgcatg agggcatgct gcacttagag atcatgcatg agaaaaagtc    6900
acaagaaaaa caaattctta aatttcacca tatttctggg aggggtaatt gggtgataag    6960
```

-continued

```
tggaggtgct ttgttgatct tgttttgcga aatccagccc ctagaccaag tagattattt   7020
gtgggtaggc cagtaaatct tagcaggtgc aaacttcatt caaatgtttg gagtcataaa   7080
tgttatgttt cttttgttg tattaaaaaa aaaacctgaa tagtgaatat tgcccctcac    7140
cctccaccgc cagaagactg aattgaccaa aattactctt tataaatttc tgcttttcc    7200
tgcactttgt ttagccatct ttgggctctc agcaaggttg acactgtata tgttaatgaa   7260
atgctattta ttatgtaaat agtcatttta ccctgtggtg cacgtttgag caaacaaata   7320
atgacctaag cacagtattt attgcatcaa atatgtacca caagaaatgt agagtgcaag   7380
ctttacacag gtaataaaat gtattctgta ccatttatag atagtttgga tgctatcaat   7440
gcatgtttat attaccatgc tgctgtatct ggtttctctc actgctcaga atctcattta   7500
tgagaaacca tatgtcagtg gtaaagtcaa ggaaattgtt caacagatct catttattta   7560
agtcattaag caatagtttg cagcacttta acagcttttt ggttattttt acattttaag   7620
tggataacat atggtatata gccagactgt acagacatgt ttaaaaaaac acactgctta   7680
acctattaaa tatgtgttta gaattttata agcaaatata aatactgtaa aaagtcactt   7740
tatttattt ttcagcatta tgtacataaa tatgaagagg aaattatctt caggttgata    7800
tcacaatcac ttttcttact ttctgtccat agtacttttt catgaaagaa atttgctaaa   7860
taagacatga aaacaagact gggtagttgt agatttctgc tttttaaatt acatttgcta   7920
atttagatt atttcacaat tttaaggagc aaaataggtt cacgattcat atccaaatta    7980
tgctttgcaa ttggaaaagg gtttaaaatt ttatttatat ttctggtagt acctgtacta   8040
actgaattga aggtagtgct tatgttattt ttgttctttt tttctgactt cggtttatgt   8100
tttcatttct ttggagtaat gctgctctag attgttctaa atagaatgtg ggcttcataa   8160
ttttttttc cacaaaaaca gagtagtcaa cttatatagt caattacatc aggacatttt    8220
gtgtttctta cagaagcaaa ccataggctc ctcttttcct taaaactact tagataaact   8280
gtattcgtga actgcatgct ggaaaatgct actattatgc taaataatgc taaccaacat   8340
ttaaaatgtg caaaactaat aaagattaca tttttatt t                        8381
```

SODIUM-CHANNEL ALPHA1-SUBUNIT AND THEIR POLYPEPTIDES AND THEIR TREATMENT OF GENERALIZED EPILEPSY WITH FEBRILE SEIZURES PLUS

TECHNICAL FIELD

The present invention relates to mutations in the alpha subunit of mammalian voltage-gated sodium channels which are associated with idiopathic epilepsies and other disorders such as malignant hyperthermia, myasthenia, episodic ataxia, neuropathic and inflammatory pain, Alzheimer's disease, Parkinson's disease, schizophrenia, hyperekplexia, myotonias and cardiac arrhythmias, and to polymorphisms in the gene encoding the alpha subunit.

BACKGROUND ART

Generalised epilepsy with febrile seizures plus (GEFS+; MIM 604236) was first described by Scheffer and Berkovic (1997) and is now recognised as a common epilepsy syndrome (Singh et al. 1999; Baulac et al. 1999; Moulard et al. 1999; Peiffer et al. 1999; Scheffer et al. 2000). Although GEFS+ is familial, it was initially difficult to recognise it as a distinct syndrome, because of clinical heterogeneity within each family. The common phenotypes are typical febrile seizures (FS) and febrile seizures plus (FS+); FS+ differs from FS in that the attacks with fever continue beyond age 6 years and/or include afebrile tonic-clonic seizures. Less common phenotypes include FS+ associated with absences, myoclonic or atonic seizures, and even more-severe syndromes such as myoclonic-astatic epilepsy. That such phenotypic diversity could be associated with the segregation of a mutation in a single gene was established with the identification of a mutation in the voltage gated sodium channel beta-1 subunit gene (SCN1B) (Wallace et al. 1998). This mutation (C121W) changes a conserved cysteine residue, disrupting a putative disulfide bridge, which results in in vitro loss of function of the beta-1 subunit. Without a functional beta-1 subunit the rate of inactivation of sodium channel alpha subunits decreases, which may cause increased sodium influx, resulting in a more depolarised membrane potential and hyperexcitability. Modifier genes or the environment may interact with the SCN1B gene to account for clinical heterogeneity, but the rarity of SCN1B mutations (Wallace et al. 1998) strongly suggested additional genes of large effect underlie GEFS+ in other families (Singh et al. 1999).

GEFS+ in four families has been mapped to chromosome 2q (Baulac et al. 1999; Moulard et al. 1999; Peiffer et al. 1999; Lopes-Cendes et al. 2000). Recently, mutations in the neuronal voltage gated sodium channel alpha-1 (SCN1A) subunit were described in two GEFS+ families (Escayg et al. 2000). The mutations (T875M and R1648H) are located in highly conserved S4 transmembrane segments of the channel which are known to have a role in channel gating. It was suggested that these mutations may reduce the rate of inactivation of SCN1A and therefore have a similar effect as the beta-1 subunit mutation.

GEFS+ is clearly a common complex disorder, with a strong genetic basis, incomplete penetrance and genetic and phenotypic heterogeneity. Febrile seizures occur in 3% of the population, and thus this phenotype may occur sporadically in GEFS+ families, in addition to occurring as a result of an inherited mutation in the GEFS+ gene (Wallace et al 1998). Also, although some families segregate an autosomal dominant gene of major effect, in many cases clinical genetic evidence, such as bilineality, suggests that for some small families the disorder is multifactorial (Singh et al 1999). Despite this, large families continue to be ascertained and with critical phenotypic analysis, they provide opportunities to localise and ultimately identify the genes involved.

DISCLOSURE OF THE INVENTION

The present inventors have identified three new mutations in the alpha-1 subunit (SCN1A) of the voltage-gated sodium channel that are associated with epilepsy, in particular generalized epilepsy with febrile seizures plus (GEFS+), and also determined the nucleotide sequence in that gene.

According to one aspect of the present invention there is provided an isolated DNA molecule encoding a mutant alpha subunit of a mammalian voltage-gated sodium channel, wherein a mutation event selected from the group consisting of point mutations, deletions, insertions and rearrangements has occurred and said mutation event disrupts the functioning of an assembled sodium channel so as to produce an epilepsy phenotype, with the proviso that the mutation event is not a C2624T transition or a G4943A transition in an alpha-1 subunit.

Preferably said mutation event is a point mutation.

Typically the mutation event occurs in an intracellular loop, preferably in the intracellular loop between transmembrane segments 2 and 3 of domain I, in the S4 segment of domain IV at amino acid position 1656, or in an S5 segment of a transmembrane domain. Preferably the mutation creates a phenotype of generalised epilepsy with febrile seizures plus.

In one form of the invention the mutation is in exon 4 of SCN1A and results in replacement of a highly conserved aspartic acid residue with a valine residue at amino acid position 188. The D188V mutation lies in the intracellular loop just outside the S3 segment of domain I of SCN1A and occurs as a result of an A to T nucleotide substitution at position 563 of the SCN1A coding sequence as shown in SEQ ID NO:1.

In a further form of the invention the mutation is in exon 21 of SCN1A and results in the replacement of a highly conserved valine residue with a leucine residue at amino acid position 1353. The V1353L mutation is located in the S5 segment of domain III of SCN1A and occurs as a result of a G to C nucleotide substitution at position 4057 of the SCN1A coding sequence as shown in SEQ ID NO:3.

In a still further form of the invention the mutation is in exon 26 of SCN1A and results in the replacement of a highly conserved isoleucine residue with a methionine residue at amino acid position 1656. The I1656M mutation is located in the S4 segment of domain IV of SCN1A and occurs as a result of a C to G nucleotide substitution at position 4968 of the SCN1A coding sequence as shown in SEQ ID NO:5.

The nucleotide sequence of the gene set forth in SEQ ID NO:89 also forms a part of the invention. In addition, the polymorphisms identified in Table 3 form part of the invention (SEQ ID Numbers:7–9 and 11).

The present invention also encompasses DNA molecules in which one or more additional mutation events selected from the group consisting of point mutations, deletions, insertions and rearrangements have occurred. Any such DNA molecule will have the mutation associated with epilepsy described above and will be functional, but otherwise may vary significantly from the DNA molecules set forth in SEQ ID NO:1, 3 and 5.

The nucleotide sequences of the present invention can be engineered using methods accepted in the art for a variety of purposes. These include, but are not limited to, modification of the cloning, processing, and/or expression of the gene product. PCR reassembly of gene fragments and the use of synthetic oligonucleotides allow the engineering of the nucleotide sequences of the present invention. For example, oligonucleotide-mediated site-directed mutagenesis can introduce further mutations that create new restriction sites, alter expression patterns and produce splice variants etc.

As a result of the degeneracy of the genetic code, a number of polynucleotide sequences, some that may have minimal similarity to the polynucleotide sequences of any known and naturally occurring gene, may be produced. Thus, the invention includes each and every possible variation of a polynucleotide sequence that could be made by selecting combinations based on possible codon choices. These combinations are made in accordance with the standard triplet genetic code as applied to the polynucleotide sequences of the present invention, and all such variations are to be considered as being specifically disclosed.

The DNA molecules of this invention include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences possessing a substantially different codon usage than that of the polynucleotide sequences of the present invention. For example, codons may be selected to increase the rate of expression of the peptide in a particular prokaryotic or eukaryotic host corresponding with the frequency that particular codons are utilized by the host. Other reasons to alter the nucleotide sequence without altering the encoded amino acid sequences include the production of RNA transcripts having more desirable properties, such as a greater half-life, than transcripts produced from the naturally occurring mutated sequence.

The invention also encompasses production of DNA sequences of the present invention entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of sequences encoding the polypeptides of the present invention. In cases where the complete coding sequence, including the initiation codon and upstream regulatory sequences, are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

According to still another aspect of the present invention there is provided an isolated DNA molecule consisting of the nucleotide sequence set forth in any one of SEQ ID NOS:1, 3, 5, 7, 8, 9, 11 and 89.

The present invention allows for the preparation of purified polypeptides or proteins from the polynucleotides of the present invention, or variants thereof. In order to do this, host cells may be transformed with a DNA molecule as described above. Typically said host cells are transfected with an expression vector comprising a DNA molecule according to the invention. A variety of expression vector/host systems may be utilized to contain and express sequences encoding polypeptides of the invention. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can be used to express a protein using various expression vectors including plasmid, cosmid and viral systems such as a vaccinia virus expression system. The invention is not limited by the host cell employed.

The polynucleotide sequences, or variants thereof, of the present invention can be stably expressed in cell lines to allow long term production of recombinant proteins in mammalian systems. Sequences encoding the polypeptides of the present invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode a protein may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of the gene are needed, such as for antibody production, vectors which direct high levels of expression of this protein may be used, such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate polynucleotide sequences of the present invention are inserted into a vector which contains a nucleotide sequence encoding another peptide (for example, glutathionine-s-transferase). The fusion protein is expressed and recovered from prokaryotic or eukaryotic cells. The fusion protein can then be purified by affinity chromatography based upon the fusion vector sequence. The desired protein is then obtained by enzymatic cleavage of the fusion protein.

Fragments of polypeptides of the present invention may also be produced by direct peptide synthesis using solid-phase techniques. Automated synthesis may be achieved by using the ABI 431A Peptide Synthesizer (Perkin-Elmer). Various fragments of this protein may be synthesized separately and then combined to produce the full length molecule.

According to still another aspect of the present invention there is provided an isolated polypeptide, said polypeptide being a mutant alpha subunit of a mammalian voltage-gated sodium channel, wherein a mutation event selected from the group consisting of point mutations, deletions, insertions and rearrangements has occurred and said mutation event disrupts the functioning of an assembled sodium channel so as to produce an epilepsy phenotype, with the proviso that said mutation event is not a T875M transition or a R1648H transition in an alpha-1 subunit.

Preferably said mutation event occurs in an intracellular loop, preferably in the intracellular loop between transmembrane segments 2 and 3 in domain I, in the S4 segment of domain IV at amino acid position 1656, or in an S5 segment of a transmembrane domain of SCN1A. Preferably the mutation creates a phenotype of generalised epilepsy with febrile seizures plus.

In one form of the invention the mutation event is a substitution in which a highly conserved aspartic acid residue is replaced with a valine residue located in the intracellular domain located just outside the S3 segment of domain I of SCN1A. Preferably the substitution is a D188V transition as illustrated in SEQ ID NO:2.

In a further form of the invention the mutation event is a substitution in which a highly conserved valine residue is replaced with a leucine residue located in the S5 segment of domain III of SCN1A. Preferably the substitution is a V1353L transition as illustrated in SEQ ID NO:4.

In a still further form of the invention the mutation event is a substitution in which a highly conserved isoleucine residue is replaced with a methionine residue located in the S4 segment of domain IV of SCN1A. Preferably the substitution is a I1656M transition as illustrated in SEQ ID NO:6.

In addition, the polymorphisms identified in Table 3 form part of the invention (SEQ ID Numbers:10 and 12). These polymorphisms may reflect changes in SCN1A which result in subtle changes of function of the sodium channel. These subtle changes may predispose individuals to epilepsy and when expressed in combination with other ion channel changes may lead to specific sub-types of the disease (see PCT/AU01/00872).

The isolated polypeptides of the present invention may have been subjected to one or more mutation events selected from the group consisting of substitutions, deletions, insertions and rearrangements in addition to the mutation associated with epilepsy. Typically these mutation events are conservative substitutions.

According to still another aspect of the present invention there is provided an isolated polypeptide comprising the sequence set forth in any one of SEQ ID NO:2, 4, 6, 10 and 12.

According to still another aspect of the present invention there is provided a polypeptide consisting of the amino acid sequence set forth in any one of SEQ ID NO:2, 4, 6, 10 and 12.

According to still another aspect of the present invention there is provided an isolated polypeptide complex, said polypeptide complex being an assembled mammalian voltage-gated sodium channel, wherein a mutation event selected from the group consisting of substitutions, deletions, insertions and rearrangements has occurred in the alpha subunit of the complex. Mutations include those in the intracellular loop between transmembrane segments 2 and 3, the S4 segment of domain IV at amino acid position 1656, or in an S5 segment of a transmembrane domain of the alpha subunit. In a particular aspect an assembled mammalian voltage-gated sodium channel bearing any such mutation in the alpha subunit will produce a phenotype of epilepsy, in particular generalised epilepsy with febrile seizures plus, or other disorders associated with sodium channel dysfunction including, but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome.

In a particular aspect there is provided a complex, being an assembled mammalian voltage-gated sodium channel, bearing a mutation in the intracellular loop between transmembrane segments 2 and 3, the S4 segment of domain IV at amino acid position 1656, or in an S5 segment of a transmembrane domain of the SCN1A subunit of the channel.

According to still another aspect of the present invention there is provided a method of preparing a polypeptide, said polypeptide being a mutant alpha subunit of a mammalian voltage-gated sodium channel, comprising the steps of:

(1) culturing host cells transfected with an expression vector comprising a nucleic acid molecule as described above under conditions effective for polypeptide production; and (2) harvesting the mutant alpha subunit.

The mutant alpha subunit may also be allowed to assemble with other subunits of the sodium channel, whereby the assembled mutant sodium channel is harvested.

According to still another aspect of the invention there is provided a polypeptide which is the product of the process described above.

Substantially purified protein or fragments thereof can then be used in further biochemical analyses to establish secondary and tertiary structure for example by X-ray crystallography of crystals of the proteins or by nuclear magnetic resonance (NMR). Determination of structure allows for the rational design of pharmaceuticals to interact with the mutated sodium channel, alter the overall sodium channel protein charge configuration or charge interaction with other proteins, or to alter its function in the cell.

It will be appreciated that, having identified mutations involved in epilepsy in these proteins, the mutant sodium channel alpha subunits will be useful in further applications which include a variety of hybridisation and immunological assays to screen for and detect the presence of either a normal or mutated gene or gene product. The invention also enables therapeutic methods for the treatment of epilepsy and enables methods for the diagnosis of epilepsy with both wild-type and mutant nucleic acid molecules. In particular the invention enables treatment and diagnosis of generalised epilepsy with febrile seizures plus, as well as other disorders associated with sodium channel dysfunction, as mentioned above.

Therapeutic Applications

According to one aspect of the invention there is provided a method of treating epilepsy, in particular generalised epilepsy with febrile seizures plus, as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome, comprising administering a selective antagonist, agonist or modulator of the sodium channel when a mutation event as described above has occurred, in particular, when it contains a mutation in the intracellular loop between transmembrane segments 2 and 3, in the S4 segment of domain IV at amino acid position 1656, or in an S5 segment of a transmembrane domain of an alpha subunit.

In still another aspect of the invention there is provided the use of a selective antagonist, agonist or modulator of the sodium channel when a mutation event as described above has occurred, in particular, to a sodium channel when it contains a mutation in the intracellular loop between transmembrane segments 2 and 3, in the S4 segment of domain IV at amino acid position 1656, or in an S5 segment of a transmembrane domain of an alpha subunit, said mutation being causative of a disorder including epilepsy, in particular generalised epilepsy with febrile seizures plus as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome, in the manufacture of a medicament for the treatment of the disorder.

In one aspect of the invention a suitable antagonist or modulator will restore wild-type function to the sodium channels that contain a mutation in an alpha subunit including those that form part of this invention.

Using methods well known in the art, a mutant sodium channel may be used to produce antibodies specific for the mutant channel that is causative of the disease or to screen libraries of pharmaceutical agents to identify those that specifically bind the mutant sodium channel.

In one aspect, an antibody, which specifically binds to a mutant sodium channel, may be used directly as an antagonist or modulator, or indirectly as a targeting or delivery mechanism for bringing a pharmaceutical agent to cells or tissues that express the mutant sodium channel.

In a still further aspect of the invention there is provided an antibody which is immunologically reactive with a polypeptide as described above, but not with a wild-type sodium channel or subunit thereof.

In particular, there is provided an antibody to an assembled sodium channel containing a mutation causative of a disorder as described above, in a subunit comprising the receptor. Such antibodies may include, but are not limited to, polyclonal, monoclonal, chimeric, and single chain antibodies as would be understood by the person skilled in the art.

For the production of antibodies, various hosts including rabbits, rats, goats, mice, humans, and others may be immunized by injection with a polypeptide as described or with any fragment or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum.*

It is preferred that the oligopeptides, peptides, or fragments used to induce antibodies to the mutant sodium channel have an amino acid sequence consisting of at least 5 amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of sodium channel amino acids may be fused with those of another protein, such as KLH, and antibodies to the chimeric molecule may be produced.

Monoclonal antibodies to a mutant sodium channel may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Antibodies may also be produced by inducing in vivo production in the lymphocyte population or by screening immunoglobulin libraries or panels of highly specific binding reagents as disclosed in the literature. (For example, see Orlandi et al., 1989; Winter et al., 1991).

Antibody fragments which contain specific binding sites for a mutant sodium channel may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such imunoassays typically involve the measurement of complex formation between a sodium channel and its specific antibody. A two-site, monoclonal-based immunoassay utilizing antibodies reactive to two non-interfering sodium channel epitopes is preferred, but a competitive binding assay may also be employed.

In a further aspect of the invention there is provided a method of treating epilepsy, in particular generalised epilepsy with febrile seizures plus, as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome, comprising administering an isolated DNA molecule which is the complement (antisense) of any one of the DNA molecules described above and which encodes an RNA molecule that hybridizes with the mRNA encoding a mutant sodium channel alpha subunit, to a subject in need of such treatment.

Typically, a vector expressing the complement of the polynucleotides of the invention may be administered to a subject in need of such treatment. Antisense strategies may use a variety of approaches including the use of antisense oligonucleotides, injection of antisense RNA, ribozymes, DNAzymes and transfection of antisense RNA expression vectors. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

In a still further aspect of the invention there is provided the use of an isolated DNA molecule which is the complement of a DNA molecule of the invention and which encodes an RNA molecule that hybridizes with the mRNA encoding a mutant sodium channel alpha subunit, in the manufacture of a medicament for the treatment of epilepsy, in particular generalised epilepsy with febrile seizures plus, as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome.

In a further aspect, a suitable agonist or modulator may include a small molecule that can restore wild-type activity of the sodium channel containing mutations in the alpha subunit as described above, or may include an antibody to a mutant sodium channel that is able to restore channel function to a normal level.

Small molecules suitable for therapeutic applications may be identified using nucleic acids and peptides of the invention in drug screening applications as described below.

In further embodiments, any of the agonists, antagonists, modulators, antibodies, complementary sequences or vectors of the invention may be administered alone or in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

Drug Screening

According to still another aspect of the invention, peptides of the invention, particularly purified mutant sodium channel alpha subunit polypeptide and cells expressing these, are useful for the screening of candidate pharmaceutical agents in a variety of techniques. It will be appreciated that therapeutic agents useful in the treatment of epilepsy, in particular generalised epilepsy with febrile seizures plus, as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome, are likely to show binding affinity to the polypeptides of the invention.

Such techniques include, but are not limited to, utilising eukaryotic or prokaryotic host cells that are stably transformed with recombinant molecules expressing the polypeptide or fragment, preferably in competitive binding assays. Binding assays will measure the formation of complexes between a mutated sodium channel alpha subunit polypeptide or fragment and the agent being tested, or will measure the degree to which an agent being tested will interfere with the formation of a complex between a mutated sodium channel alpha subunit polypeptide or fragment and a known ligand.

Another technique for drug screening provides high-throughput screening for compounds having suitable binding affinity to the mutant sodium channel alpha subunit polypeptides or sodium channels containing these (see PCT published application WO84/03564). In this stated technique, large numbers of small peptide test compounds can be synthesised on a solid substrate and can be assayed through mutant sodium channel or mutant sodium channel alpha subunit polypeptide binding and washing. Bound mutant sodium channel or mutant sodium channel alpha subunit polypeptide is then detected by methods well known in the art. In a variation of this technique, purified polypeptides of the invention can be coated directly onto plates to identify interacting test compounds.

The invention also contemplates the use of competition drug screening assays in which neutralizing antibodies capable of specifically binding the mutant sodium channel compete with a test compound for binding thereto. In this manner, the antibodies can be used to detect the presence of any peptide that shares one or more antigenic determinants of the mutant sodium channel.

The invention is particularly useful for screening compounds by using the polypeptides of the invention in transformed cells, transfected or injected oocytes, or animal models bearing mutated sodium channel alpha subunits (particularly those of the invention) such as transgenic animals or gene targeted (knock-in) animals (see below). A particular drug is added to the cells in culture or administered to an animal model containing a mutant sodium channel alpha subunit and the effect on the current of the channel is compared to the current of a cell or animal containing the wild-type sodium channel. Drug candidates that alter the current to a more normal level are useful for treating or preventing epilepsy, in particular generalised epilepsy with febrile seizures plus as well as other disorders associated with sodium channel dysfunction, as described above.

The polypeptides of the present invention may also be used for screening compounds developed as a result of combinatorial library technology. This provides a way to test a large number of different substances for their ability to modulate activity of a polypeptide. The use of peptide libraries is preferred (see WO 97/02048) with such libraries and their use known in the art.

A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to isolate peptides from chemically or biologically produced peptide banks.

Any of the therapeutic methods described above may be applied to any subject in need of such therapy, including, for example, mammals such as dogs, cats, cows, horses, rabbits, monkeys, and most preferably, humans.

Diagnostic Applications

Polynucleotide sequences of the invention may be used for the diagnosis of epilepsy, in particular generalised epilepsy with febrile seizures plus, as well as other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome, and the use of the DNA molecules of the invention in diagnosis of these disorders, is therefore contemplated.

In another embodiment of the invention, the polynucleotides that may be used for diagnostic purposes include oligonucleotide sequences, genomic DNA and complementary RNA and DNA molecules. The polynucleotides may be used to detect and quantitate gene expression in biological samples. Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, hybridisation using specific oligonucleotides, restriction enzyme digest and mapping, PCR mapping, RNAse protection, and various other methods may be employed. For instance direct nucleotide sequencing of amplification products from the sodium channel subunits can be employed. Sequence of the sample amplicon is compared to that of the wild-type amplicon to determine the presence (or absence) of nucleotide differences.

According to a further aspect of the invention there is provided the use of a polypeptide as described above in the diagnosis of epilepsy, in particular generalised epilepsy with febrile seizures plus, as well as other disorders associated with sodium channel dysfunction, as described above.

When a diagnostic assay is to be based upon mutant proteins constituting a sodium channel, a variety of approaches are possible. For example, diagnosis can be achieved by monitoring differences in the electrophoretic mobility of normal and mutant alpha subunit proteins that form part of the sodium channel. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In another aspect, antibodies that specifically bind mutant sodium channels may be used for the diagnosis of epilepsy, or in assays to monitor patients being treated with agonists, antagonists, modulators or inhibitors of the mutant sodium channel. Antibodies useful for diagnostic purposes may be prepared in the same manner as described above for therapeutics. Diagnostic assays to detect mutant sodium channels include methods that utilize the antibody and a label to detect a mutant sodium channel in human body fluids or in extracts of cells or tissues. The antibodies may be used with or without modification, and may be labelled by covalent or non-covalent attachment of a reporter molecule.

A variety of protocols for measuring the presence of mutant sodium channels, including ELISAs, RIAs, and FACS, are known in the art and provide a basis for diagnosing epilepsy, in particular generalised epilepsy with febrile seizures plus, as well as other disorders associated with sodium channel dysfunction, as described above. The expression of a mutant channel is established by combining body fluids or cell extracts taken from test mammalian subjects, preferably human, with antibody to the channel under conditions suitable for complex formation. The amount of complex formation may be quantitated by various methods, preferably by photometric means. Antibodies specific for the mutant channel will only bind to individuals expressing the said mutant channel and not to individuals expressing only wild-type channels (ie normal individuals). This establishes the basis for diagnosing the disease.

Once an individual has been diagnosed with the disorder, effective treatments can be initiated. These may include administering a selective modulator of the mutant channel or an antagonist to the mutant channel such as an antibody or mutant complement as described above. Alternative treatments include the administering of a selective agonist or modulator to the mutant channel so as to restore channel function to a normal level.

Microarray

In further embodiments, complete cDNAs, oligonucleotides or longer fragments derived from any of the polynucleotide sequences described here in may be used as probes in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents. Microarrays may be prepared, used, and analyzed using methods known in the art. (For example, see Schena et al., 1996; Heller et al., 1997).

According to a further aspect of the present invention, neurological material obtained from animal models generated as a result of the identification of specific sodium channel alpha subunit human mutations, particularly those disclosed in the present invention, can be used in microarray experiments. These experiments can be conducted to identify the level of expression of specific sodium channel alpha subunits, or any cDNA clones from whole-brain libraries, in epileptic brain tissue as opposed to normal control brain tissue. Variations in the expression level of genes, including sodium channel alpha subunits, between the two tissues indicates their involvement in the epileptic process either as a cause or consequence of the original sodium channel mutation present in the animal model. Microarrays may be prepared, as described above.

Transformed Hosts

The present invention also provides for the production of genetically modified (knock-out, knock-in and transgenic), non-human animal models transformed with the DNA molecules of the invention. These animals are useful for the study of the function of a sodium channel, to study the mechanisms of disease as related to a sodium channel, for the screening of candidate pharmaceutical compounds, for the creation of explanted mammalian cell cultures which express a mutant sodium channel and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired due to their similarity with humans.

To create an animal model for a mutated sodium channel several methods can be employed. These include but are not limited to generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create a transgenic or gene targeted (knock-in) mouse, which is preferred, a mutant version of a sodium channel alpha subunit can be inserted into a mouse germ line using standard techniques of oocyte microinjection, or transfected into embryonic stem cells, respectively. Alternatively, if it is desired to inactivate or replace an endogenous sodium channel alpha subunit gene, homologous recombination using embryonic stem cells may be applied.

For oocyte injection, one or more copies of the mutant sodium channel alpha subunit gene can be inserted into the pronucleus of a just-fertilized mouse oocyte. This oocyte is then reimplanted into a pseudo-pregnant foster mother. The liveborn mice can then be screened for integrants using analysis of tail DNA or DNA from other tissues for the presence of the particular human subunit gene sequence. The transgene can be either a complete genomic sequence injected as a YAC, BAC, PAC or other chromosome DNA fragment, a complete cDNA with either the natural promoter or a heterologous promoter, or a minigene containing all of the coding region and other elements found to be necessary for optimum expression.

According to still another aspect of the invention there is provided the use of genetically modified non-human animals as described above for the screening of candidate pharmaceutical compounds.

It will be clearly understood that, although a number of prior art publications are referred to herein, this reference does not constitute an admission that any of these documents forms part of the common general knowledge in the art, in Australia or in any other country.

Throughout this specification and the claims, the words "comprise", "comprises" and "comprising" are used in a non-exclusive sense, except where the context requires otherwise.

BRIEF DESCRIPTION OF THE DRAWINGS

Preferred forms of the invention are described, by way of example only, with reference to the following examples and the accompanying drawings, in which:

FIG. 3. Sodium channel amino acid alignments. Alignment of sodium channel amino acids surrounding the three SCN1A mutations.

MODES FOR PERFORMING THE INVENTION

EXAMPLE 1

Clinical Diagnosis of Affected Family Members

A group of 53 unrelated probands with GEFS+ phenotypes were studied. These subjects were ascertained on the basis of twin and family studies and on the basis of routine clinical practice. Phenotypes in probands and family members were classified as described elsewhere (Scheffer & Berkovic 1997; Singh et al 1999). Familial cases (n=36) were those in which at least one first-degree relative of the proband had a phenotype within the GEFS+ spectrum. Informed consent was obtained from all subjects.

Figure 1A:
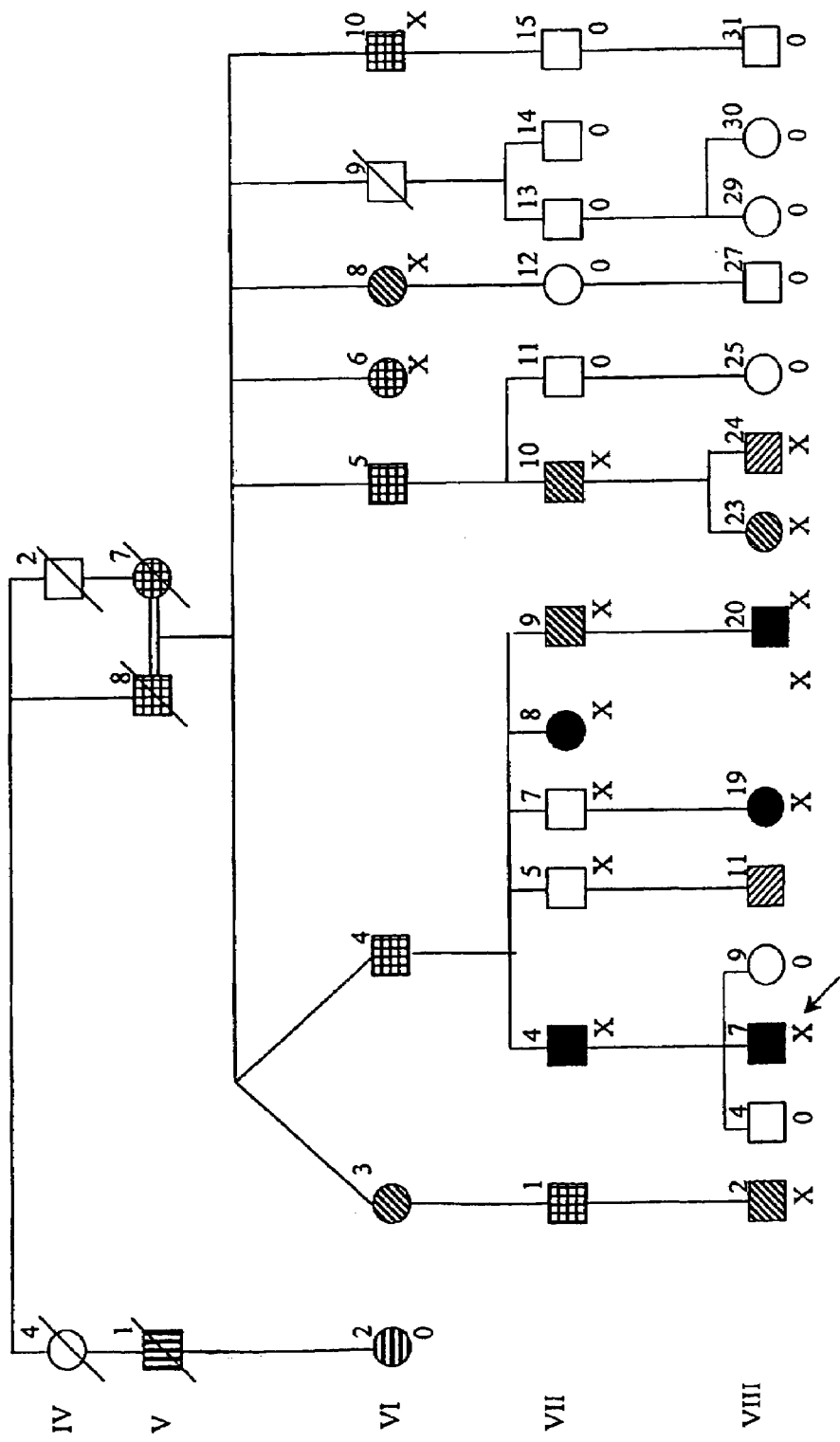
FIG. 1. Generalised epilepsy with febrile seizures plus (GEFS+) pedigrees are shown for the three families. DNA was not available from those individuals not assigned a letter (X, Y, or Z) or a 0. A: Pedigree of an Australian family with individual numbering for this family based on FIG. 1 in Scheffer & Berkovic (1997). B: Pedigree of an Ashkenazi family. C: Pedigree of a Druze family.

The Australian family in FIG. 1A, which has been described extensively elsewhere (Scheffer & Berkovic, 1997; Lopes-Cendes et al, 2000), is the original pedigree leading to the initial delineation and description of the GEFS+ syndrome.

Figure 1B:
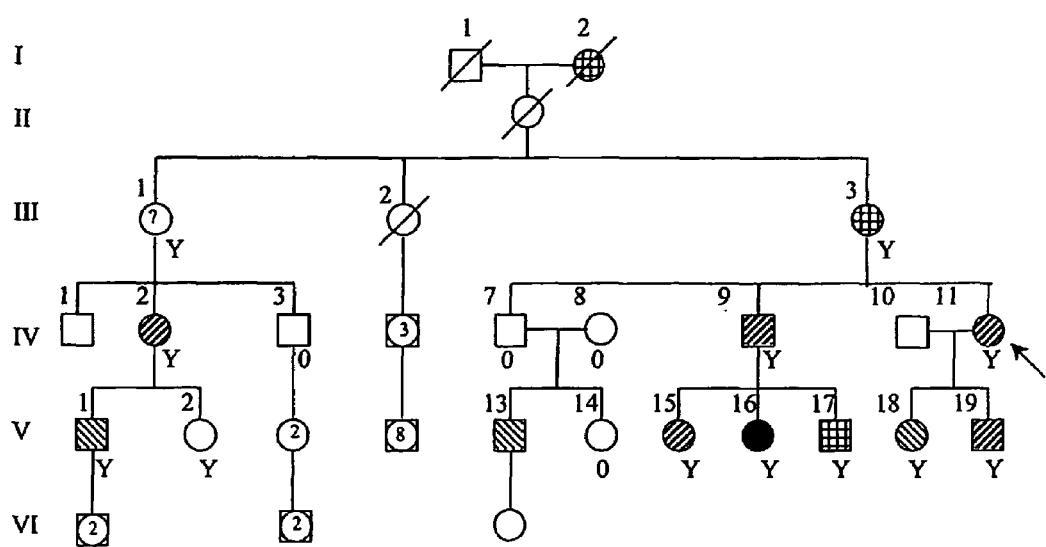

The Israeli family in FIG. 1B is of Ashkenazi origin and spans six generations. Twelve family members had seizures. In the two oldest members (I-2, III-3) seizures had occurred in childhood but the data were insufficient to allow classification of the phenotype. Of the 10 other family members who had seizures, 3 had febrile seizures with onset at age 9–13 months. All attacks occurred with fever and offset occurred between 1 and 4 years with 1 to 7 attacks each. Five had febrile seizures plus with onset at age 9–24 months, offset between 5 and 41 years and 2 to 15 attacks each. Seizures during childhood were a mixture of febrile seizures and afebrile tonic-clonic seizures, whereas the rarely occurring seizures during teenage and adult years were all afebrile. Subject V-16 had a more severe phenotype with approximately 20 febrile seizures at age 6 months to 5 years, 10 afebrile tonic-clonic seizures at age 5 to 15 years and occasional complex partial seizures associated with mild learning difficulties. She was classified as having febrile seizures plus and complex partial seizures. Her older sister (V-15) had typical febrile seizures plus, but their younger brother (V-17), aged 14 years, had no febrile seizures but had two afebrile tonic-clonic seizures at ages 12 years 6 months and 14 years. For purposes of linkage analysis, he was regarded as affected, although he had only afebrile tonic-clonic seizures. All affected subjects were of normal or superior intellect, except V-16 (see above) and all had a normal neurological examination. Electroencephalography (EEG) studies had been performed infrequently during the active phase of the epilepsy, and the results usually either were normal or were reported to show generalized discharges.

Figure 1C:
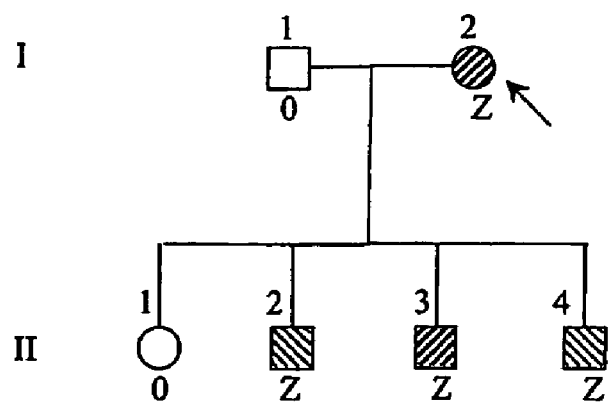

The second Israeli family was of Druze origin; the parents were from different but proximate villages and were not known to be related. This family spans two generations, and four family members had seizures (FIG. 1C). The proband aged 41 years (I-2) had had hundreds of tonic-clonic seizures, sometimes with fever. These began at age 4 years and continued, at a rate of approximately one per month, until the time of the study. The proband was mildly intellectually impaired. EEG showed generalized irregular spike-wave and polyspike-wave discharges, and febrile seizures plus was diagnosed. Of her four children, the oldest was unaffected (II-1), two had febrile seizures (II-2, II-4) and one had febrile seizures plus (II-3).

EXAMPLE 2

Isolation and Sequencing of SCN1A Genomic Clones

At the commencement of this study the full-length sequence of the human SCN1A gene was not known. To determine this sequence a human BAC library obtained from Gename Systems was initially screened to identify human genomic sequence clones containing the SCN1A gene. The BAC filters were screened with a PCR product amplified with the primer pair 5' AGATGACCAGAGTGAATATGT-GACTAC 3' (SEQ ID NO:13) and 5' CCAATGG-TAAAATAATAATGGCGT 3' (SEQ ID NO:14) designed from the partial cDNA sequence of human SCN1A (Genbank Accession Number X65362).

The BAC filters were hybridised and washed according to manufacturers recommendations. Initially, membranes were individually pre-hybridised in large glass bottles for at least 2 hours in 20 ml of 6×SSC; 0.5% SDS; 5× Denhardt's; 100 ug/ml denatured salmon sperm DNA at 65° C. Overnight hybridisations with [$\alpha$-$^{32}$P]dCTP labelled probes were performed at 65° C. in 20 ml of a solution containing 6×SSC; 0.5% SDS; 100 ug/ml denatured salmon sperm DNA. Filters were washed sequentially in solutions of 2×SSC; 0.5% SDS (room temperature 5 minutes), 2×SSC; 0.1% SDS (room temperature 15 minutes) and 0.1×SSC; 0.5% SDS (37° C. 1 hour if needed).

A number of BAC clones were identified from this hybridisation and BAC129e04 was selected for subcloning and sequencing. DNA from this BAC clone was sheared by nebulisation (10 psi for 45 seconds). Sheared DNA was then blunt ended using standard methodologies (Sambrook et al., 1989) and run on an agarose gel in order to isolate DNA in the 2–4 Kb size range. These fragments were cleaned from the agarose using QIAquick columns (Qiagen), ligated into puc18 and used to transform competent XL-1 Blue *E. coli* cells. DNA was isolated from transformed clones and was sequenced using vector specific primers on an ABI377 sequencer to generate 1× coverage of the BAC clone. Sequence data were assembled in contigs using the Phred, Phrap and Gap4 high throughput sequencing software. Exon-intron boundaries were predicted based on the rat Scn1a cDNA sequence (Genbank Accession Number M22253) due to the full length human cDNA sequence of SCN1A not being known.

The human SCN1A gene was determined to be 8,381 base pair in length and is organised into 27 exons spanning over 100 Kb of genomic DNA. To facilitate a comparison with related sodium channels SCN4A, SCN5A and SCN8A, the first untranslated exon of SCN1A is designated exon 1A and the second exon, containing the start codon, remains exon 1 (Table 1). The SCN1A gene shows high homology to SCN2A and SCN3A at both the DNA and protein level. The close proximity of these genes to each other on chromosome 2 indicates likely duplication events during the evolution of the sodium channel gene family. Compared to SCN4A and SCN8A, additional sequence is present in the 3'UTR of SCN1A, giving the final exon an overall length of ~3.3 Kb.

Inspection of the splice junctions of SCN1A shows that there is close agreement with consensus splice motifs, with all introns bounded by GT-AG, except for two (introns 2 and 23). These introns exhibit deviation from the consensus splice pattern and are bounded by AT-AC terminal dinucleotides. These rare splice site variations are conserved in other characterised sodium channel subunits (SCN4A, SCN8A and the more distantly related SCN5A), indicating their ancient origin.

The intron positions are also highly conserved between sodium channel subunits, with most variation seen in the region that codes for the cytoplasmic loop between domains I and II of the gene (Table 1). Within this region, alternative splicing of exon 11 of SCN1A was found that was comparable to the alternative splicing of exon 10B in SCN8A (Plummer et al. 1998). Cytoplasmic loop 1 varies in both length and composition and is the proposed site of functional diversity among different sodium channels (Plummer & Meisler, 1999).

EXAMPLE 3

Analysis of SCN1A for Mutations in Epilepsy

The determination of the genomic structure of SCN1A allowed the design of intronic primers (Table 2 and SEQ ID Numbers:15–88) to amplify each of the 27 exons of SCN1A in order to test for mutations in patients with generalised epilepsy with febrile seizures plus (GEFS+). A total of 53 unrelated patients (as described above) were screened by fluorescent single stranded conformation polymorphism (SSCP) analysis.

HEX-labelled primers were designed to amplify all exons of SCN1A (Table 2). A 30 ng sample of patient DNA was amplified in a total volume of 10 ul. Products were separated on non-denaturing 4% polyacrylamide gels containing 2% glycerol using the GelScan 2000 (Corbett Research). PCR products showing a conformational change were reamplified from 100 ng of genomic DNA with unlabelled primers and sequenced using the BigDye Terminator ready reaction kit (Perkin Elmer) according to manufacturers instructions.

Figure 2:
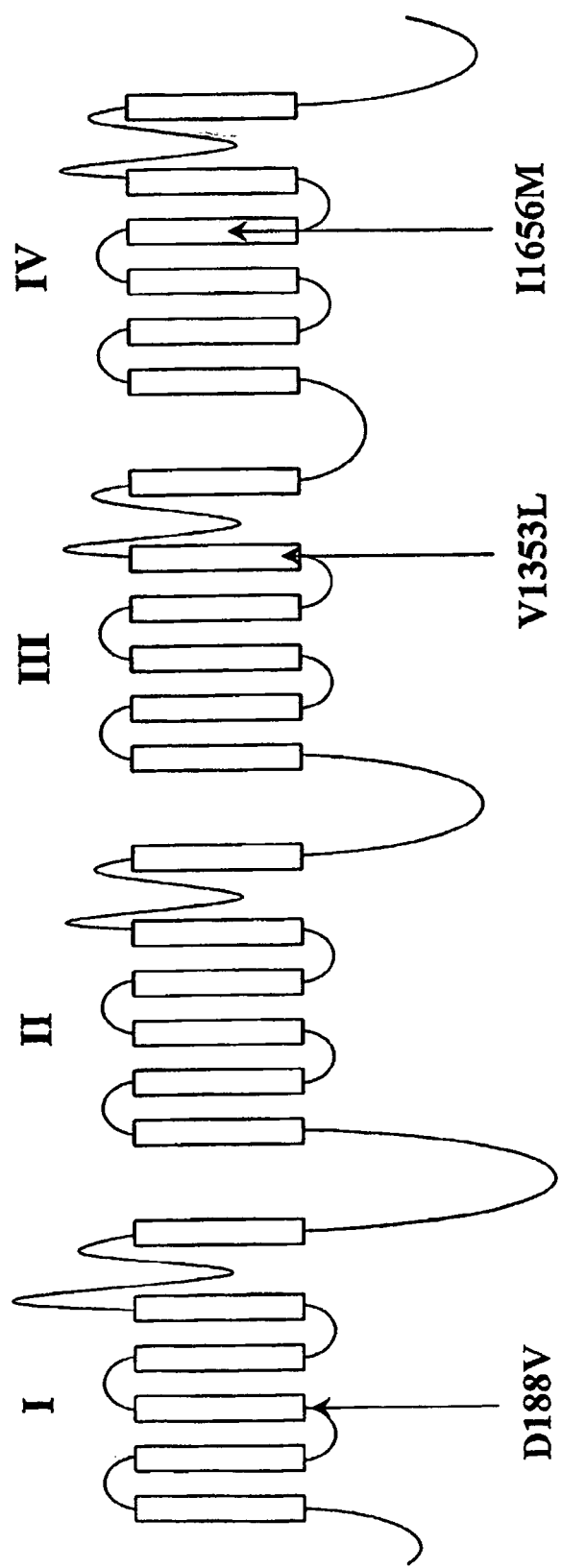
FIG. 2. Schematic of the alpha subunit of the sodium channel (SCN1A), showing the position of the three mutations identified in this study.

A total of 53 unrelated patients with GEFS+ were screened by fluorescent SSCP, including two families consistent with mapping to the same location as SCN1A on chromosome 2 (FIGS. 1A and 1B). No mutations were found in 17 sporadic cases of GEFS+ that were tested. Of the 36 families tested, 3 were found to have point mutations in SCN1A, which alter the amino acid sequence and are not present in the control population (n=60). The phenotype in the family in FIG. 1A previously had been mapped to chromosome 2 (Lopes-Cendes et al. 2000) and carries an A to T mutation at position 563 of the SCN1A coding sequence. This mutation segregates with affected family members. This mutation in exon 4 of SCN1A results in a D188V amino acid substitution that lies just outside the S3 segment of domain I (FIG. 2). The aspartic acid residue is conserved in all identified sodium channels in humans as well as in many different animal species, except the jellyfish which has an arginine at this residue and the flatworm which has a serine (FIG. 3). The published rat Scn2a sequence (Genbank Accession Number NM_012647) also has an arginine in place of the aspartic acid at residue 188.

A mutation in exon 21 (G to C nucleotide change at position 4057 of the SCN1A coding sequence) was found to segregate with GEFS+ in the Ashkenazi family (FIG. 1B). This mutation changes a highly conserved amino acid (V1353L) located in the S5 segment of domain III (FIG. 2). One family member (V-13) did not carry the mutation (FIG. 1B). This was determined by testing the DNA of a parent of this family member, since the subjects DNA was unavailable. This individual, who had typical febrile seizures that terminated at an early age, is likely to be a phenocopy. Mutations in the S5 segment of SCN4A that cause hyperkalemic periodic paralysis have been shown also to affect the rate of channel inactivation (Bendahhou et al., 1999)

A third mutation (C to G nucleotide change at position 4968 of the SCN1A coding sequence) discovered in the Druze family (FIG. 1C), changes an amino acid (I1656M) in the S4 segment of domain IV (FIG. 2). The S4 segment has a role in channel gating and mutations in this region of SCN1A reduce the rate of inactivation (Kuhn and Greef, 1996).

During the mutation screen of SCN1A several single nucleotide polymorphisms (SNPs) were identified (Table 3). The R1928G variant was found at low frequency in both GEFS+ and control populations. The T1067A variant was common in both populations and the remaining SNPs identified did not alter the amino acid sequence of SCN1A (Table 3).

EXAMPLE 4

Analysis of a Mutated Sodium Channels and Sodium Channel Alpha Subunits

The following methods are used to determine the structure and function of mutated sodium channel or sodium channel alpha subunits.

Molecular Biological Studies

The ability of the mutated sodium channel as a whole or through individual alpha subunits to bind known and unknown proteins can be examined. Procedures such as the yeast two-hybrid system are used to discover and identify any functional partners. The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media). The second reporter is used for confirmation and while being expressed in response to interacting proteins it is usually not required for growth.

The nature of the genes and proteins interacting with the mutant sodium channels can also be studied such that these partners can also be targets for drug discovery.

Structural Studies

Recombinant proteins corresponding to mutated sodium channel alpha subunits can be produced in bacterial, yeast, insect and/or mammalian cells and used in crystallographical and NMR studies. Together with molecular modeling of the protein, structure-driven drug design can be facilitated.

EXAMPLE 5

Generation of Polyclonal Antibodies Against a Mutant Sodium Channel or Sodium Channel Alpha Subunit Following the identification of new mutations in the alpha subunit of the sodium channel in individuals with generalised epilepsy with febrile seizures plus, antibodies can be made to the mutant channel which can selectively bind and distinguish mutant from normal protein. Antibodies specific for mutagenised epitopes are especially useful in cell culture assays to screen for cells which have been treated with pharmaceutical agents to evaluate the therapeutic potential of the agent.

To prepare polyclonal antibodies, short peptides can be designed homologous to a sodium channel subunit amino acid sequence. Such peptides are typically 10 to 15 amino acids in length. These peptides should be designed in regions of least homology to other receptor subunits and should also have poor homology to the mouse orthologue to avoid cross species interactions in further down-stream experiments such as monoclonal antibody production. Synthetic peptides can then be conjugated to biotin (Sulfo-NHS-LC Biotin) using standard protocols supplied with commercially available kits such as the PIERCE™ kit (PIERCE). Biotinylated peptides are subsequently complexed with avidin in solution and for each peptide complex, 2 rabbits are immunized with 4 doses of antigen (200 ug per dose) in intervals of three weeks between roses. The initial dose is mixed with Freund's Complete adjuvant while subsequent doses are combined with Freund's Immuno-adjuvant. After completion of the immunization, rabbits are test bled and reactivity of sera is assayed by dot blot with serial dilutions of the original peptides. If rabbits show significant reactivity compared with pre-immune sera, they are then sacrificed and the blood collected such that immune sera can be separated for further experiments.

This procedure is repeated to generate antibodies against wild-type forms of receptor subunits. The antibodies specific for mutant sodium channels can subsequently be used to detect the presence and the relative level of the mutant forms in various tissues.

EXAMPLE 6

Generation of Monoclonal Antibodies Against a Mutant Sodium Channel or Sodium Channel Alpha Subunit Monoclonal antibodies can be prepared in the following manner. Immunogen, comprising intact mutated sodium channel or sodium channel alpha subunit peptides, is injected in Freund's adjuvant into mice with each mouse receiving four injections of 10 ug to 100 ug of immunogen. After the fourth injection blood samples taken from the mice are examined for the presence of antibody to the immunogen. Immune mice are sacrificed, their spleens removed and single cell suspensions are prepared (Harlow and Lane, 1988). The spleen cells serve as a source of lymphocytes, which are then fused with a permanently growing myeloma partner cell (Kohler and Milstein, 1975). Cells are plated at a density of $2 \times 10^5$ cells/well in 96 well plates and individual wells are examined for growth. These wells are then tested for the presence of sodium channel specific antibodies by ELISA or RIA using wild type or mutant subunit target protein. Cells in positive wells are expanded and subcloned to establish and confirm monoclonality. Clones with the desired specificity are expanded and grown as ascites in mice followed by purification using affinity chromatography using Protein A Sepharose, ion-exchange chromatography or variations and combinations of these techniques.

INDUSTRIAL APPLICABILITY

The present invention allows for the diagnosis and treatment of epilepsy or other disorders associated with sodium channel dysfunction, including but not restricted to, malignant hyperthermia, myasthenia, episodic ataxia, neuropathic and inflammatory pain, Alzheimer's disease, Parkinson's disease, schizophrenia, hyperekplexia, myotonias such as hypo- and hyperkalaemic periodic paralysis, paramyotonia congenita and potassium aggravated myotonia as well as cardiac arrhythmias such as long QT syndrome. In particular, the present invention allows for the diagnosis and treatment of generalised epilepsy with febrile seizures plus.

In one embodiment, disclosed is an isolated nucleic acid molecule encoding a mutant alpha subunit of a mammalian voltage-gated sodium channel, wherein a mutation event selected from the group consisting of point mutations, deletions, insertions and rearrangements has occurred in an intracellular loop, in the S4 segment of domain IV at nucleotide position 4968 of the alpha-1 subunit coding sequence or homologous nucleotide position in the coding sequence of other alpha subunits, or in an S5 segment of a transmembrane domain so as to produce an epilepsy phenotype.

Also disclosed herein is an isolated polypeptide, the polypeptide being a mutant alpha subunit of a mammalian voltage-gated sodium channel, wherein a mutation event selected from the group consisting of substitutions, deletions, insertions and rearrangements has occurred and the mutation event disrupts the functioning of an assembled sodium channel so as to produce an epilepsy phenotype, with the proviso that the mutation event is not a T875M transition or a R1648H transition in an alpha-1 subunit.

Optionally, the mutation event occurs in an intracellular loop, in one embodiment, the mutation event occurs in an intracellular loop between transmembrane segments 2 and 3 of domain I. Optionally, the mutation event is a substitution. The substitution can involve replacement of an aspartic acid residue at position 188 of the alpha-1 subunit of a sodium channel. The aspartic acid residue can be replaced with a valine residue. An isolated polypeptide can comprise the amino acid sequence set forth in SEQ ID NO:2. An isolated polypeptide having the amino acid sequence set forth in SEQ ID NO:2 is also disclosed.

The mutation event can occur in an S5 segment of a transmembrane domain, such as in the S5 segment of domain III. Optionally, the mutation event is a substitution. The substitution can involve replacement of a valine residue at position 1353 of the alpha-1 subunit of a sodium channel. The valine residue can be replaced with a leucine residue. An isolated polypeptide can comprise the amino acid sequence set forth in SEQ ID NO:4. An isolated polypeptide having the amino acid sequence set forth in SEQ ID NO:4 is also disclosed.

The mutation event can occur in an S4 segment of a transmembrane domain. Optionally, the mutation avant occurs in the S4 segment of domain IV. An isoleucine residue at position 1656 of the alpha-1 subunit of a sodium channel can be replaced. The isoleucine residue can be replaced with a methionine residue. An isolated polypeptide can comprise the amino acid sequence set forth in SEQ ID NO:6. An isolated polypeptide having the amino acid sequence set forth in SEQ ID NO:6 is also disclosed.

Also disclosed is an isolated polypeptide, the polypeptide being a mutant α-subunit of a mammalian voltage-gated sodium channel, wherein a mutation event selected from the group of substitutions, deletions, insertions and rearrangements has occurred in an intracellular loop, in the S4 segment of domain IV at amino acid position 1656 of the alpha-1 subunit or homologous amino acid position of other alpha subunits, or in an S5 segment of a transmembrane domain. Also disclosed is an isolated polypeptide, the polypeptide being an assembled mammalian voltage-gated sodium channel comprising an alpha subunits as defined herein. An isolated polypeptide selected from the group consisting of polypeptides with the amino acid sequence set forth in SEQ ID NO:10 or SEQ ID NO:12 is also disclosed.

The use of a polypeptide as disclosed herein for the screening of candidate pharmaceutical agents is also provided. Optionally, high throughput screening techniques are employed. The use of a polypeptide as defined herein in the diagnosis of epilepsy, in particular generalised epilepsy with febrile seizures plus, as well as other disorders associated with sodium channel dysfunction is also provided.

Also disclosed is an antibody which is immunologically reactive with a mutant polypeptide as defined herein, but not with a wild-type mammalian voltage-gated sodium channel. The antibody can be selected from the group consisting of a monoclonal antibody, a humanised antibody, a chimaeric antibody or an antibody fragment including a Fab fragment, (Fab')2 fragment, Fv fragment, single chain antibodies and single domain antibodies. Also disclosed is the use of an antibody as defined herein in the diagnosis of epilepsy, in particular generalised epilepsy with febrile seizures plus, as well as other disorders associated with sodium channel dysfunction.

In another embodiment a method of treating disorders associated with sodium channel dysfunction is disclosed. The method can comprise administering a selective agonist, antagonist or modulator of the sodium channel when it has undergone a mutation event as defined herein to a patient in need of such treatment. The use of a selective agonist, antagonist or modulator of the sodium channel when it has undergone a mutation event as defined herein in the manufacture of a medicament for the treatment of a disorder associated with sodium channel dysfunction is also disclosed.

Also disclosed is a method of treating disorders associated with sodium channel dysfunction, comprising administering an isolated DNA molecule which is the complement (antisense) of a nucleic acid molecule as defined herein and which encodes an RNA molecule that hybridizes with the mRNA encoding a mutant sodium channel alpha subunit to a subject in need of such treatment. Also disclosed is the use of an isolated DNA molecule which is the complement of a nucleic acid molecule as herein and which encodes an RNA molecule that hybridizes with the mRNA encoding a mutant sodium channel alpha subunit, in the manufacture of a medicament for the treatment of disorders associated with sodium channel dysfunction.

TABLE 1

Comparison of Exon Sizes of SCN1A with Other Human SCNA Subunits

| SCN1A | | SCN4A | | SCN8A | | SCN5A | |
|---|---|---|---|---|---|---|---|
| Exon No. | Exon Size | Exon No. | Exon Size | Exon No. | Exon Size | Exon No. | Exon Size |
| 1A | 217 | — | — | — | — | 1 | 98 |
| 1 | 313 | 1 | 661 | 1 | 276 | 2 | 324 |
| 2 | 119 | 2 | 119 | 2 | 121 | 3 | 119 |
| 3 | 90 | 3 | 90 | 3 | 88 | 4 | 90 |
| 4 | 129 | 4 | 129 | 4 | 129 | 5 | 129 |
| 5 | 92 | 5 | 92 | 5 | 92 | 6 | 92 |
| 6 | 270 | 6 | 333 | 6 | 222 | 7 | 231 |
| 7 | 64 | 7 | 64 | 7 | 64 | 8 | 64 |
| 8 | 142 | 8 | 142 | 8 | 142 | 9 | 142 |
| 9 | 207 | 9 | 210 | 9 | 207 | 10 | 198 |
| 10 | 285 | 10 | 154 | 10A | 294 | 11 | 180 |
| 11 | 381 | — | — | 10B | 396 | 12 | 372 |
| 12 | 133 | — | — | 10C | 133 | 13 | 133 |
| 13 | 239 | 11 | 239 | 11 | 239 | 14 | 239 |
| 14 | 174 | 12 | 174 | 12 | 174 | 15 | 174 |
| 15 | 357 | 13 | 357 | 13 | 357 | 16 | 351 |
| 16 | 483 | 14 | 477 | 14 | 471 | 17 | 441 |
| | | | | | | 18 | 162 |
| 17 | 121 | 15 | 136 | 15 | 118 | 19 | 121 |
| 18 | 155 | 16 | 155 | 16 | 155 | 20 | 155 |
| 19 | 174 | 17 | 174 | 17 | 174 | 21 | 174 |
| 20 | 123 | 18 | 123 | 18A | 123 | 22 | 123 |
| 21 | 282 | 19 | 279 | 19 | 285 | 23 | 282 |
| 22 | 54 | 20 | 54 | 20 | 54 | 24 | 54 |
| 23 | 138 | 21 | 138 | 21 | 138 | 25 | 138 |
| 24 | 105 | 22 | 105 | 22 | 105 | 26 | 105 |
| 25 | 271 | 23 | 271 | 23 | 271 | 27 | 271 |
| 26 | 3263 | 24 | >2242 | 24 | >1158 | 28 | 3257 |

Note:
D: Transmembrane domain;
C: Cytoplasmic loop.

TABLE 2

Primer Sequences Used for Mutation Analysis of SCN1A

| Exon | Forward Primer | Reverse Primer | Size (bp) |
|---|---|---|---|
| 1A | TACCATAGAGTGAGGCGAGG | ATGGACTTCCTGCTCTGCCC | 356 |
| 1 | CCTCTAGCTCATGTTTCATGAC | TGCAGTAGGCAATTAGCAGC | 448 |
| 2 | CTAATTAAGAAGAGATCCAGTGACAG | GCTATAAAGTGCTTACAGATCATGTAC | 356 |
| 3 | CCCTGAATTTTGGCTAAGCTGCAG | CTACATTAAGACACAGTTTCAAAATCC | 263 |
| 4 | GGGCTACGTTTCATTTGTATG | GCAACCTATTCTTAAAGCATAAGACTG | 355 |
| 5 | AGGCTCTTTGTACCTACAGC | CATGTAGGGTCCGTCTCATT | 199 |
| 6 | CACACGTGTTAAGTCTTCATAGT | AGCCCCTCAAGTATTTATCCT | 394 |
| 7 | GAACCTGACCTTCCTGTTCTC | GTTGGCTGTTATCTTCAGTTTC | 241 |
| 8 | GACTAGGCAATATCATAGCATAG | CTTTCTACTATATTATCATCCGG | 320 |
| 9 | TTGAAAGTTGAAGCCACCAC | CCACCTGCTCTTAGGTACTC | 363 |
| 10 | GCCATGCAAATACTTCAGCCC | CACAACAGTGGTTGATTCAGTTG | 480 |
| 11a | TGAATGCTGAAATCTCCTTCTAC | CTCAGGTTGCTGTTGCGTCTC | 306 |
| 11b | GATAACGAGAGCCGTAGAGAT | TCTGTAGAAACACTGGCTGG | 315 |
| 12 | CATGAAATTCACTGTGTCACC | CAGCTCTTGAATTAGACTGTC | 347 |
| 13a | ATCCTTGGGAGGTTTAGAGT | CATCACAACCAGGTTGACAAC | 292 |

TABLE 2-continued

Primer Sequences Used for Mutation Analysis of SCN1A

| Exon | Forward Primer | Reverse Primer | Size (bp) |
|---|---|---|---|
| 13b | CTGGGACTGTTCTCCATATTG | GCATGAAGGATGGTTGAAAG | 277 |
| 14 | CATTGTGGGAAAATAGCATAAGC | GCTATGCAGAACCCTGATTG | 338 |
| 15a | TGAGACGGTTAGGGCAGATC | AGAAGTCATTCATGTGCCAGC | 348 |
| 15b | CTGCAAGATCGCCAGTGATTG | ACATGTGCACAATGTGCAGG | 276 |
| 16a | GTGGTGTTTCCTTCTCATCAAG | TCTGCTGTATGATTGGACATAC | 387 |
| 16b | CAACAGTCCTTCATTAGGAAAC | ACCTTCCCACACCTATAGAATC | 353 |
| 17 | CTTGGCAGGCAACTTATTACC | CAAGCTGCACTCCAAATGAAAG | 232 |
| 18 | TGGAAGCAGAGACACTTTATCTAC | GTGCTGTATCACCTTTTCTTAATC | 234 |
| 19 | CCTATTCCAATGAAATGTCATATG | CAAGCTACCTTGAACAGAGAC | 318 |
| 20 | CTACACATTGAATGATGATTCTGT | GCTATATACAATACTTCAGGTTCT | 216 |
| 21a | ACCAGAGATTACTAGGGGAAT | CCATCGAGCAGTCTCATTTCT | 303 |
| 21b | ACAACTGGTGACAGGTTTGAC | CTGGGCTCATAAACTTGTACTAAC | 297 |
| 22 | ACTGTCTTGGTCCAAAATCTG | TTCGATTAATTTTACCACCTGATC | 267 |
| 23 | AGCACCAGTGACATTTCCAAC | GGCAGAGAAAACACTCCAAGG | 272 |
| 24 | GACACAGTTTTAACCAGTTTG | TGTGAGACAAGCATGCAAGTT | 207 |
| 25 | CAGGGCCAATGACTACTTTGC | CTGATTGCTGGGATGATCTTGAATC | 477 |
| 26a | CGCATGATTTCTTCACTGGTTGG | GCGTAGATGAACATGACTAGG | 247 |
| 26b | TCCTGCGTTGTTTAACATCGG | ATTCCAACAGATGGGTTCCCA | 288 |
| 26c | TGGAAGCTCAGTTAAGGGAGA | AGCGCAGCTGCAAACTGAGAT | 261 |
| 26d | CCGATGCAACTCAGTTCATGGA | GTAGTGATTGGCTGATAGGAG | 274 |
| 26e | AGAGCGATTCATGGCTTCCAATCC | TGCCTTCTTGCTCATGTTTTTCCACA | 335 |
| 26f | CCTATGACCGGGTGACAAAGCC | TGCTGACAAGGGGTCACTGTCT | 242 |

Note:
Primer sequences are listed 5' to 3'. Due to the large size of exons 11, 13, 15, 16, 21 and 26, the exons were split into two or more overlapping amplicons.

TABLE 3

SCN1A Polymorphisms Identified

| | | Amino Acid | Frequency (%) | |
|---|---|---|---|---|
| Position | Mutation | Change | GEFS+ | Normal |
| Intron 13 | IVS13-37C>A | — | 2.4 | 8.6 |
| Exon 14 | c.2522C>G | — | 2.4 | 8.6 |
| Inron 15 | IVS15+54A>G | — | 36.3 | 23.6 |
| Exon 15 | c.2889T>C | — | 1.2 | 0.0 |
| Exon 16 | c.3199G>A | T1067A | 29.5 | 30.8 |
| Exon 26 | c.5782C>G | R1928G | 1.2 | 1.7 |

Note:
Total GEFS+ samples = 53; Total normal samples = 60.

REFERENCES

References cited herein are listed on the following pages, and are incorporated herein by this reference.

Baulac S. et al. (1999). *Am. J. Hum. Genet.* 65: 1078–1085.
Bendahhou S. et al. (1999). *J. Neurosci.* 19: 4762–4771.
Cole, S P. et al. (1984). *Mol. Cell Biol.* 62: 109–120.
Cote, R J. et al. (1983). *Proc. Natl. Acad. Sci. USA* 80: 2026–2030.
Escayg A. et al. (2000). *Nature Genet.* 24: 343–345.
Goldman, C K. et al. (1997). *Nature Biotechnology* 15: 462–466.
Harlow, E. and Lane, D. (1988). *Antibodies: A Laboratory Manual* (Cold Spring Harbor Laboratory, Cold Spring Harbor, N.Y.).
Heller, R A. et al. (1997). *Proc. Natl. Acad. Sci. USA* 94: 2150–2155.
Huse, W D. et al. (1989). *Science* 246: 1275–1281.
Kohler, G. and Milstein, C. (1975). *Nature* 256: 495–497.
Kozbor, D. et al. (1985). *J. Immunol. Methods* 81:31–42.

Kuhn, F J P. and Greeff, N G. (1996) *J. Gen. Physiol.* 114: 167–183.
Lopes-Cendes I. et al. (2000). *Am. J. Hum. Genet.* 66: 698–701.
Moulard B. et al. (1999). *Am. J. Hum. Genet.* 65: 1396–1400.
Orlandi, R. et al. (1989). *Proc. Natl. Acad. Sci. USA* 86: 3833–3837.
Peiffer A. et al. (1999). *Ann. Neurol.* 46: 671–678.
Plummer N W. et al. (1998). *Genomics* 54: 287–296.
Plummer N W. and Meisler N H. (1999). *Genomics* 57: 323–331.
Sambrook, J. et al. (1989). *Molecular cloning: a laboratory manual.* Second Edition. (Cold Spring Harbour Laboratory Press, New York).
Scharf, D. et al. (1994). *Results Probl. Cell Differ.* 20: 125–162.
Scheffer I E. and Berkovic S F. (1997). *Brain* 120: 479–490.
Scheffer I E. et al. (2000). *Ann. Neurol.* 47: 840–841.
Schena, M. et al. (1996). *Proc. Natl. Acad. Sci. USA* 93: 10614–10619.
Singh R. et al. (1999). *Ann Neurol.* 45: 75–81.
Wallace R H. et al. (1998). *Nature Genet.* 19: 366–370.
Winter, G. et al. (1991). *Nature* 349: 293–299.

The invention claimed is:

1. An isolated nucleic acid molecule comprising the nucleotide sequence set forth in SEQ ID NO:3.

2. An isolated nucleic acid molecule comprising the nucleotide sequence set forth in SEQ ID NO:5.

3. An isolated nucleic acid molecule selected from the group consisting of the nucleotide sequence set forth in SEQ ID NO:3 and SEQ ID NO:5.

4. An isolated cell transformed with an isolated nucleic acid molecule as claimed in claim 1.

5. A method of preparing a polypeptide encoded by SEQ ID NO:3 comprising the steps of:
   (1) culturing the cell as claimed in claim 4 under conditions effective for polypeptide production; and
   (2) harvesting said polypeptide.

6. An isolated polypeptide encoded by SEQ ID NO:3 prepared by the method of claim 5.

7. An expression vector comprising an isolated nucleic acid molecule as claimed in claim 1.

8. An isolated cell transformed with an isolated nucleic acid molecule as claimed in claim 2.

9. A cell as recited in claim 8, wherein the cell is a eukaryotic or bacterial cell.

10. A method of preparing a polypeptide encoded by SEQ ID NO:5 comprising the steps of:
    (1) culturing the cell as claimed in claim 8 under conditions effective for polypeptide production; and
    (2) harvesting said polypeptide.

11. An isolated polypeptide encoded by SEQ ID NO:5 prepared by the method of claim 10.

12. An isolated polypeptide encoded by an isolated nucleic acid molecule as claimed in claim 2.

13. An expression vector comprising an isolated nucleic acid molecule as claimed in claim 2.

14. An isolated cell transformed with an isolated nucleic acid molecule as claimed in claim 3.

15. A cell as recited in claim 14, wherein the cell is a eukaryotic or bacterial cell.

16. A method of preparing a polypeptide encoded by SEQ ID NO:3 or SEQ ID NO:5 comprising the steps of:
    (1) culturing the cell as claimed in claim 14 under conditions effective for polypeptide production; and
    (2) harvesting said polypeptide.

17. An isolated polypeptide encoded by SEQ ID NO:3 or SEQ ID NO:5 prepared by the method of claim 16.

18. An isolated polypeptide encoded by an isolated nucleic acid molecule as claimed in claim 3.

19. An expression vector comprising an isolated nucleic acid molecule as claimed in claim 3.

20. A cell as recited in claim 4, wherein the cell is a eukaryotic or bacterial cell.

* * * * *